(12) United States Patent
Chen et al.

(10) Patent No.: US 9,309,259 B2
(45) Date of Patent: Apr. 12, 2016

(54) PROCESS FOR IXABEPILONE, AND INTERMEDIATES THEREOF

(71) Applicant: ScinoPharm Taiwan, Ltd., Tainan (TW)

(72) Inventors: Yue Chen, Tianjin (CN); Tsung Yu Hsiao, Kaohsiung (TW); Julian P. Henschke, Summertown (AU)

(73) Assignee: SCINOPHARM TAIWAN, LTD., Tainan (TW)

( * ) Notice: Subject to any disclaimer, the term of this patent is extended or adjusted under 35 U.S.C. 154(b) by 0 days.

(21) Appl. No.: 14/201,113

(22) Filed: Mar. 7, 2014

(65) Prior Publication Data

US 2014/0256952 A1    Sep. 11, 2014

Related U.S. Application Data

(60) Provisional application No. 61/775,461, filed on Mar. 8, 2013.

(30) Foreign Application Priority Data

Mar. 4, 2014   (CN) .......................... 2014 1 0077611

(51) Int. Cl.
    *C07D 491/044* (2006.01)
(52) U.S. Cl.
    CPC .................................. *C07D 491/044* (2013.01)
(58) Field of Classification Search
    USPC ........................................................ 540/462
    See application file for complete search history.

(56) References Cited

U.S. PATENT DOCUMENTS

| 6,365,749 B1 | 4/2002 | Kim et al. |
| 6,518,421 B1 | 2/2003 | Li et al. |
| 6,605,599 B1 | 8/2003 | Vite et al. |
| 6,867,305 B2 | 3/2005 | Danishefsky et al. |

FOREIGN PATENT DOCUMENTS

| WO | 99/02514 A2 | 1/1999 |
| WO | 01/64650 A2 | 9/2001 |
| WO | 2008/141130 A1 | 11/2008 |

OTHER PUBLICATIONS

Schinzer et al., "Synthesis and Biological Evaluation of Aza-Epothilones," ChemBioChem, 2000, vol. 1(1), pp. 67-70.
PCT Application No. PCT/IB2014/059543; International Search Report and Written Opinion, Jun. 3, 2014, 12 pages.
Altmann, Karl-Heinz et al., "The Total Synthesis and Biological Assessment of *trans*-Epothilone A," *Helvetica Chimica Acta* (2002) 85:4086-4110.
Borzilleri, Robert M. et al., "A Novel Application of a Pd(0)-Catalyzed Nucleophilic Substitution Reaction to the Regio- and Stereoselective Synthesis of Lactam Analogues of the Epothilone Natural Products," *J. Am. Chem. Soc.* (2000) 122:8890-8897.
Cao et al., "Short Synthesis of the C1-C14 Stretch of Discodermolide from Building Blocks Prepared by Asymmetric Catalysis," *Org. Lett.* (2008) 10(7):1353-1356.
Harris, Christina R. et al., "New Chemical Synthesis of the Promising Cancer Chemotherapeutic Agent 12,13-Desoxyepothilone B: Discovery of a Surprising Long-Range Effect on the Diastereoselectivity of an Aldol Condensation," *J. Am. Chem. Soc.* (1999) 121:7050-7062.
Jung, Jae-Chul et al., "Total Syntheses of Epothilones B and D.," *J. Org. Chem.* (2004) 69:9269-9284.
Lentsch, Christoph et al., "General Synthesis of Highly Functionalized Cyclopentane Segments for the Preparation of Jatrophane Diterpenes," *Org. Lett.* (2009) 11(22):5326-5328.
Koch, Guido et al., "Diastereoselective Titanium Enolate Aldol Reaction for the Total Synthesis of Epothilones," *Org. Lett.* (2002) 4(22):3811-3814.
Miyaura, Norio et al., "Palladium-Catalyzed Inter- and Intramolecular Cross-Coupling Reactions of B-Alkyl-9-borabicyclo[3.3.1]nonane Derivatives with 1-Halo-1-alkenes or Haloarenes. Syntheses of Functionalized Alkenes, Arenes, and Cycloalkenes via a Hydroboration-Coupling Sequencen," *J. Am. Chem. Soc.* (1989) 111:314-321.
Miyaura, Norio et al., "Palladium-Catalyzed Cross-Coupling Reactions of Organoboron Compounds," *Chem. Rev.* (1995) 95:2457-2483.
Sawada, Daisuke et al., "Enantioselective Total Synthesis of Epothilones A and B Using Multifunctional Asymmetric Catalysis," *J. Am. Chem. Soc.* (2000) 122:10521-10532.
Stachel, Shawn J. et al., "On the Total Synthesis and Preliminary Biological Evaluations of 15(R) and 15(S) Aza-dEpoB: A Mitsunobu Inversion at C15 in Pre-Epothilone Fragments," *Org. Lett.* (2000) 2(11):1637-1639.
Stachel, Shawn J. et al., "On the Interactivity of Complex Synthesis and Tumor Pharmacology in the Drug Discovery Process: Total Synthesis and Comparative in ivo Evaluations of the 15-Aza Epothilones," *J. Org. Chem.* (2001) 66:4369-4378.

*Primary Examiner* — Laura L. Stockton

(74) *Attorney, Agent, or Firm* — Kilpatrick Townsend & Stockton LLP

(57) ABSTRACT

The present invention relates to a novel process of making ixabepilone, ixabepilone derivatives and analogues, and intermediates thereof.

19 Claims, 20 Drawing Sheets

Scheme 1 – Synthesis of amine derivative 20 as per U.S. Patent No. 6,605,599

Scheme 2 - Synthesis of azaepothilones from epothilones approach

Scheme 3 - Ring opening of epothilone derivatives as per U.S. Patent No. 6,365,749

Scheme 4 - Conversion of epothilones to azaepothilones as per U.S. Patent No. 6,518,421

Scheme 5 - Synthesis of ixabepilone as per *J. Org. Chem.* 2001, *66*, 4369–4378

Scheme 6 – Synthetic strategy as described herein

Scheme 7 - Synthesis of Unit A

Scheme 8 - Synthesis of Unit AB (II)

Scheme 9 – The two major diastereomers of XXII or XXII' formed in the titanium-enolate aldol reaction of XIX or XIX' and XX Scheme 10 - Synthesis of Unit C (III)

Scheme 11 - Synthesis of IIIa-e

Scheme 12 – Conversion of XII to IIIa–e

Scheme 13 - Synthesis of acyclic precursor ABC

Scheme 14 - Synthesis of intermediates IVax and IVax' for synthesis of azaepothilones including ixabepilone Scheme 15 - Synthesis of azaepothilones from acyclic precursor ABC Scheme 16 - Synthesis of ixabepilone using preferred methods of the invention Scheme 17 - Synthesis of Ia from XXVIax, via IXa, using preferred methods of the invention Scheme 18 – Synthesis of Ia from partially protected intermediates XXII or XXIIa', using preferred methods of the invention Schemes from Example 1

Schemes from Example 2

Schemes from Example 3

Schemes from Example 4

Schemes from Example 5

Schemes from Example 6

Schemes from Example 7

Schemes from Example 8

Schemes from Example 9

Schemes from Example 10

Schemes from Example 10

Schemes from Example 10

Schemes from Example 11

PROCESS FOR IXABEPILONE, AND INTERMEDIATES THEREOF

CROSS-REFERENCES TO RELATED APPLICATIONS

This application claims the benefit of priority to U.S. Provisional Patent Application No. 61/775,461, filed Mar. 8, 2013, and Chinese Patent Application No. 201410077611.6, filed Mar. 4, 2014, each of which is incorporated by reference in its entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Ixempra® (International non-propriety name (INN): ixabepilone) is an injectable antineoplastic agent belonging to the epothilone class. It is a synthetic derivative of the natural product epothilone B (a.k.a., EpoB), with the macrolide ring oxygen atom replaced with a nitrogen atom to give the corresponding macrolactam. The chemical name of ixabepilone (a.k.a., aza-EpoB, azaepothilone B and BMS-247550) is ((1S,3S,7S,10R,11S,12S,16R)-7,11-dihydroxy-8,8,10,12,16-pentamethyl-3-[(1E)-1-methyl-2-(2-methyl-4-thiazolyl)ethenyl]-17-oxa-4-azabicyclo[14.1.0]heptadecane-5,9-dione.

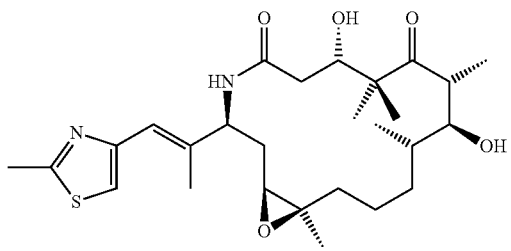

Ixabepilone is a white to off-white powder with a molecular formula of $C_{27}H_{42}N_2O_5S$ and a molecular weight of 506.70. Ixabepilone was developed by Bristol-Myers Squibb and was approved by the U.S. Food and Drug Administration (FDA) for the treatment of metastatic breast cancer on Oct. 16, 2007. It is a cytotoxic microtubule stabilizer and the first member of the epothilone family of anticancer agents to be approved.

Analogues E-Epo C-lactam, Epo A-lactam, Epo F-lactam, Z-Epo C-lactam, Z-Epo D-lactam, E-Epo D-lactam of ixabepilone have also been reported (see *J. Am. Chem. Soc.* 2000, 122, 8890-8897). The C15 epimer (a.k.a., 15-epi-aza-dEpoB, 15-epi-12,13-desoxy-15-azaepothilone B and 15-epi-15-azaepothilone D) of Z-Epo D-lactam has also been reported (*Org. Lett.* 2000, 2, 1637-1639).

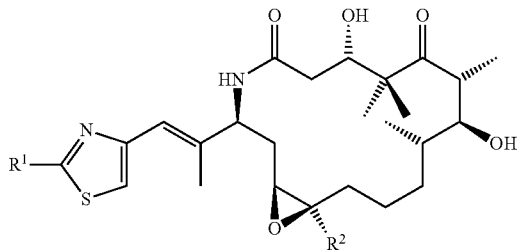

Epo A-lactam: $R^1$ = Me, $R^2$ = H
Epo F-lactam: $R^1$ = $CH_2OH$, $R^2$ = Me

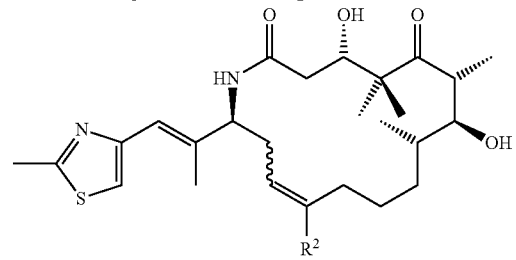

Z-Epo C-lactam: $R^2$ = H, Z-alkene (C12,C13)
Z-Epo D-lactam: $R^2$ = Me, Z-alkene (C12,C13)
E-Epo C-lactam: $R^2$ = H, E-alkene (C12,C13)
E-Epo D-lactam: $R^2$ = Me, E-alkene (C12,C13)

U.S. Pat. No. 6,605,599 (the '599 patent) describes two approaches for synthesizing azaepothilones such as ixabepilone. One synthetic strategy to prepare the azaepothilone is based on a ring-closing olefin metathesis (RCM) reaction to cyclise a linear amide compound into a macrocyclic lactam (a.k.a., a macrolactam).

The '599 patent also discloses the preparation of amine derivatives 20 from aldehyde 18 (a commercially available compound) as shown in Scheme 1. Imine derivative 19 is treated with an allylating reagent such as allylmagnesium bromide. The '599 patent, however, does not describe the preparation of a homochiral form of amine derivative 20, nor does $R_{15}$ include any chiral auxiliary compounds.

The '599 patent also discloses a method for azaepothilone synthesis from epothilones as shown in Scheme 2. Compounds 103 can be prepared from compounds 5 by reaction with a palladium complex followed by treatment with sodium azide. Subsequent reduction of compounds 103 provides compounds 104. Finally, compounds 5 are obtained by macrolactamization of compounds 104. This procedure was used to prepare ixabepilone from the natural product epothilone B (a.k.a., EpoB, patupilone, EPO 906) in a step-wise approach in a 13-21% overall yield or a 23% overall yield in a one-pot, three-step protocol (*J. Am. Chem. Soc.* 2000, 122, 8890-8897).

U.S. Pat. No. 6,365,749 discloses a process to produce ring opened epothilone derivatives 1 from epothilones 3 as shown in Scheme 3. The epothilone derivatives 3 can be treated with a palladium catalyst and nitrogen-based nucleophile to provide ring opened epothilone derivatives 1. When X is $NH_2$, the derivatives can be macrolactamized to produce azaepothilones.

U.S. Pat. No. 6,518,421 discloses the conversion of epothilones into azaepothilones as shown in Scheme 4 comprising macrolactone ring opening of epothilones 3 to provide ammonium carboxylate salts and subsequent macrolactamization to afford azaepothilones 2. This can be stepwise or in a single reaction vessel without isolation of the salt intermediate, and can be used to convert epothilone B to ixabepilone.

A total synthesis method for the preparation of ixabepilone was disclosed in U.S. Pat. No. 6,867,305 and *J. Org. Chem.* 2001, 66, 4369-4378. This approach comprises B-alkyl Suzuki coupling of fragments D1 and a borane derivative of alkene D2 (Scheme 5). D1*b* was coupled with borane derivative of alkene D2*c* in 78% yield using a Suzuki coupling, then converted to ixabepilone in a process requiring an additional 8 synthetic steps, including macrolactamization. The Suzuki coupling of the N—BOC amine derivative IIIa' or the azide derivative D1*b* with D2a gave only 10% and 63% yields in the Suzuki reaction, respectively.

It was believed that the low yield in the coupling of IIIa' was due to the presence of the N—BOC (BOC is tert-butyloxycarbonyl; $CO_2$t-Bu; t-BuOCO) carbamate group. This was seemingly supported when an improved 63% yield was obtained by substituting the N—BOC carbamate group of vinyl iodide IIIa' with an azide, as in azido vinyl iodide D1*b*. However, in all cases the arsenic-based ligand $AsPh_3$ was used in the B-alkyl Suzuki reaction. Arsenic is toxic, and the use of arsenic-based reagents is to be highly avoided in API manufacturing processes due to strict requirements on the levels of arsenic that are allowed in drug substances ($\leq 2$ ppm) for human consumption. Accordingly, if arsenic-based reagents are used in the manufacture of an API, a significant (and costly) burden is placed on the manufacturer to control the level of arsenic to acceptable levels. It is therefore preferable to avoid the use of arsenic-based reagents in API manufacture.

In view of the above, there remains a need for a process for the manufacture of ixabepilone and its derivatives that does not reply upon the use of epothilones, which are natural products, as starting materials. There is also a need for a process for the manufacture of ixabepilone that requires fewer chemical steps following formation of the complete acyclic precursor of ixabepilone as compared to the relevant art.

BRIEF SUMMARY OF THE INVENTION

The present invention relates to a novel process of making ixabepilone, ixabepilone derivatives and analogues, and intermediates thereof.

In one aspect of the present invention, a process for preparing a compound of formula I from three building blocks, Unit A, Unit B, and Unit C, is provided. I itself might be useful as a drug substance, or alternatively can be derivatised to provide other substances with useful drug properties.

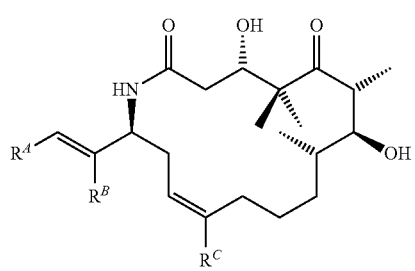

I

Unit A is ketone XIX or its diastereomer XIX'

Unit A

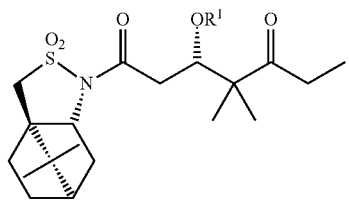

XIX

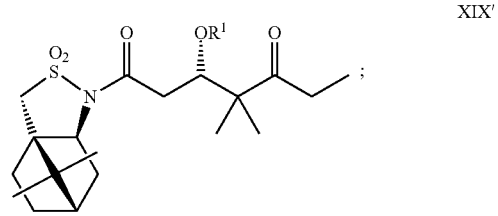

XIX'

Unit B is aldehyde XX

Unit B

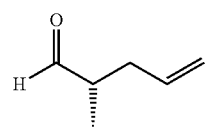

XX and
Unit C is amino vinyl iodide III (wherein X is I)

Unit C

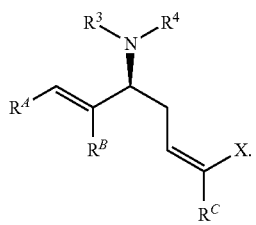

III

Unit A, Unit B and Unit C are sequentially coupled together to give a compound of formula IV.

IV

The compound of formula IV is converted to a compound of formula V.

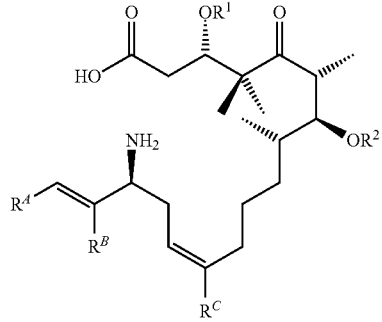

V

The compound of formula V is then cyclised to give a macrolactam VI or I.

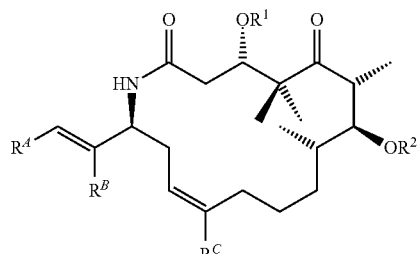

VI

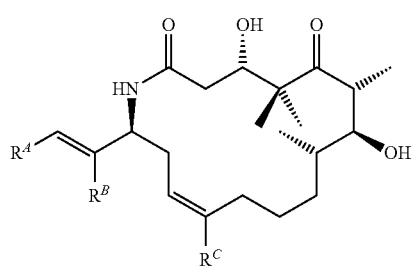

I

Compounds having formula I are optionally converted into ixabepilone, ixabepilone derivatives and analogues of ixabepilone represented by formula VII.

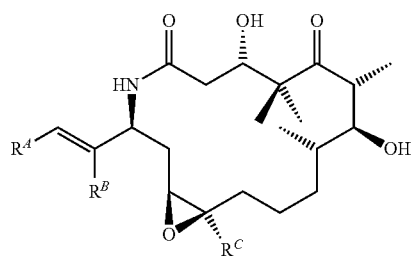

VII

In another aspect of the present invention, a process is provided for preparing a compound of formula III' which is a useful building block that can be used for the first aspect of the present invention.

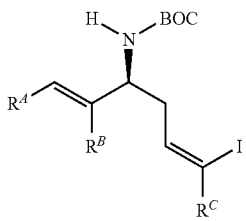

III'

The process comprises converting the aldehyde of formula X

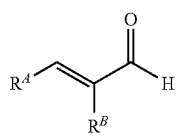

X into a chiral derivative of formula XI

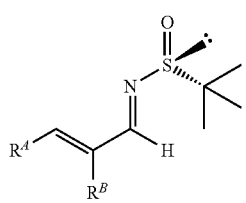

XI that is stereoselectively reacted with an allylating reagent to give a compound of formula XII.

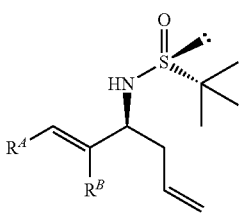

XII

The compound of formula XII is converted into a compound of formula III'.

DETAILED DESCRIPTION OF THE INVENTION

I. General

Figure 1:
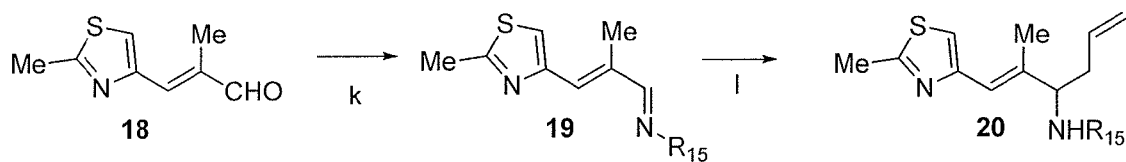
FIG. 1 provides Scheme 1 for the synthesis of amine derivative 20 as described in U.S. Pat. No. 6,605,599.
Figure 2:
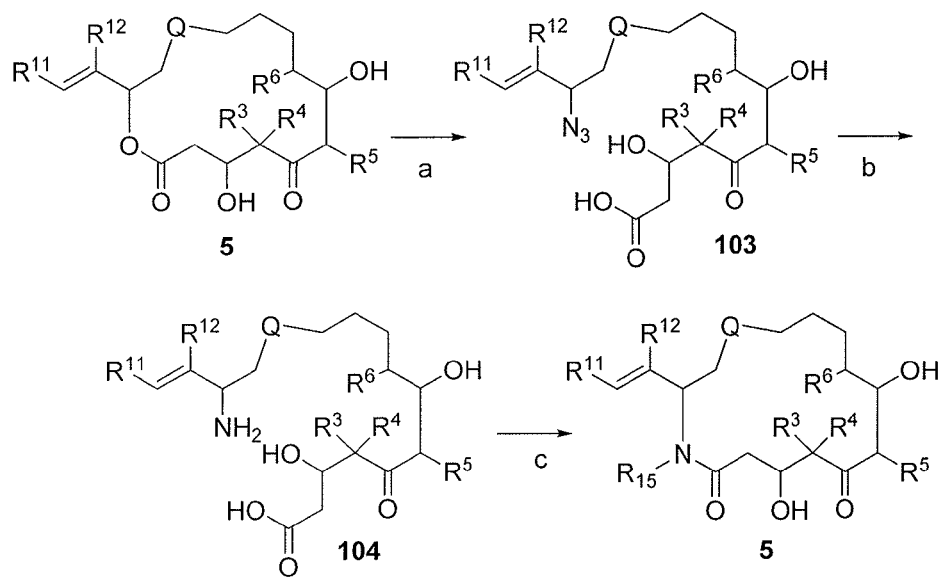
FIG. 2 provides Scheme 2, showing the synthesis of azaepothilones from epothilones.
Figure 3:
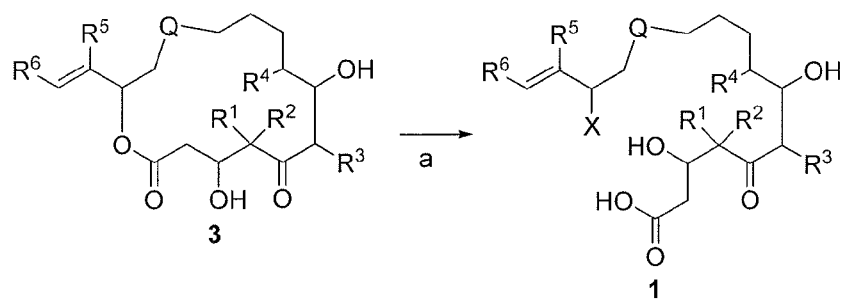
FIG. 3 provides Scheme 3, showing a ring opening of epothilone derivatives as provided in U.S. Pat. No. 6,365,749.
Figure 4:
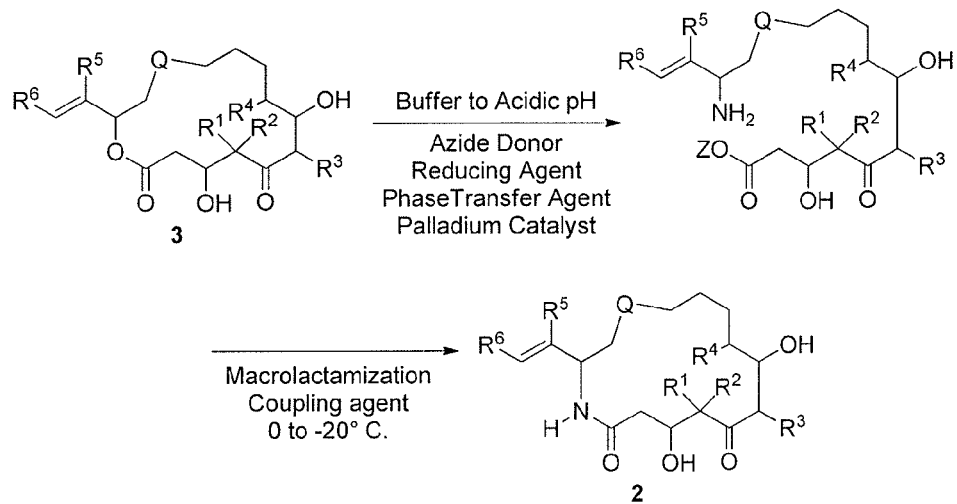
FIG. 4 provides Scheme 4, showing a conversion of epothilones to azaepothilones as described in U.S. Pat. No. 6,518,421.
Figure 5:
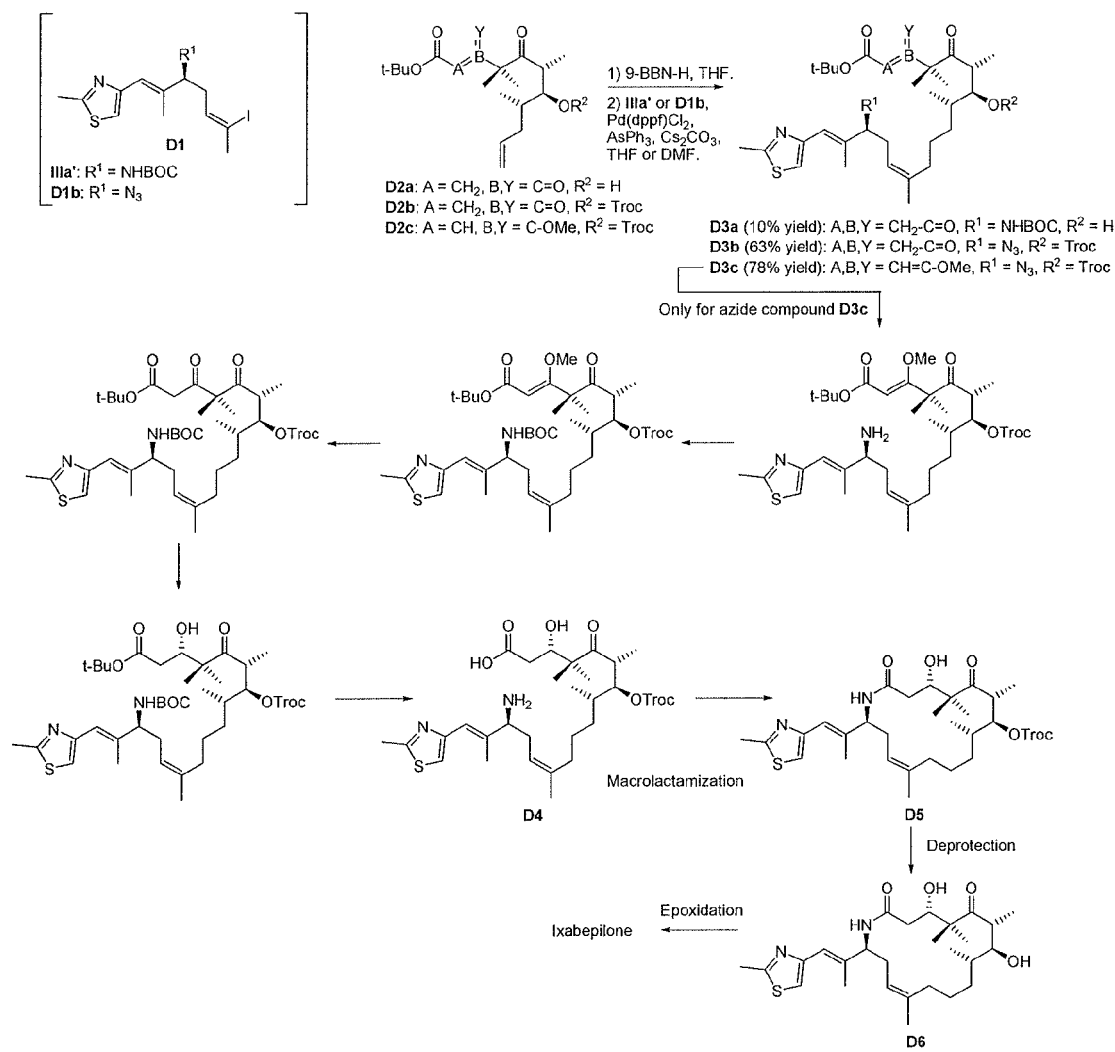
FIG. 5 provides Scheme 5, illustrating the synthesis of ixabepilone, described in *J. Org. Chem.* 2001, 66, 4369-4378.
Figure 6:
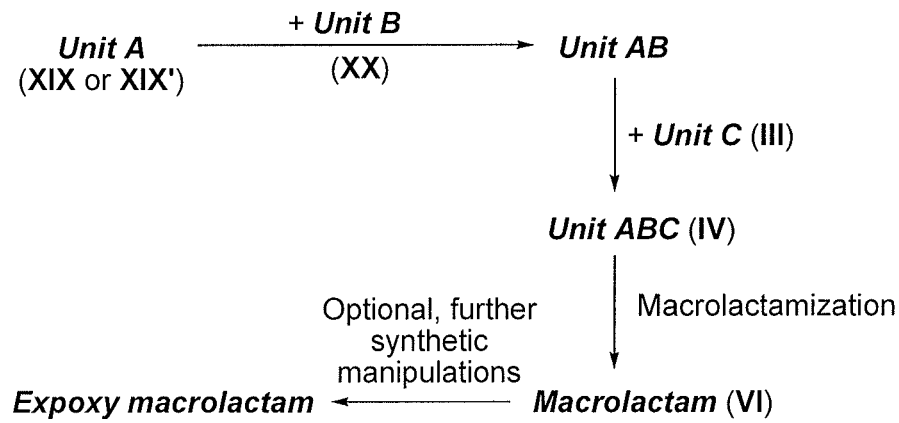
FIG. 6 provides Scheme 6, illustrating the synthetic strategy described herein.
Figure 7:
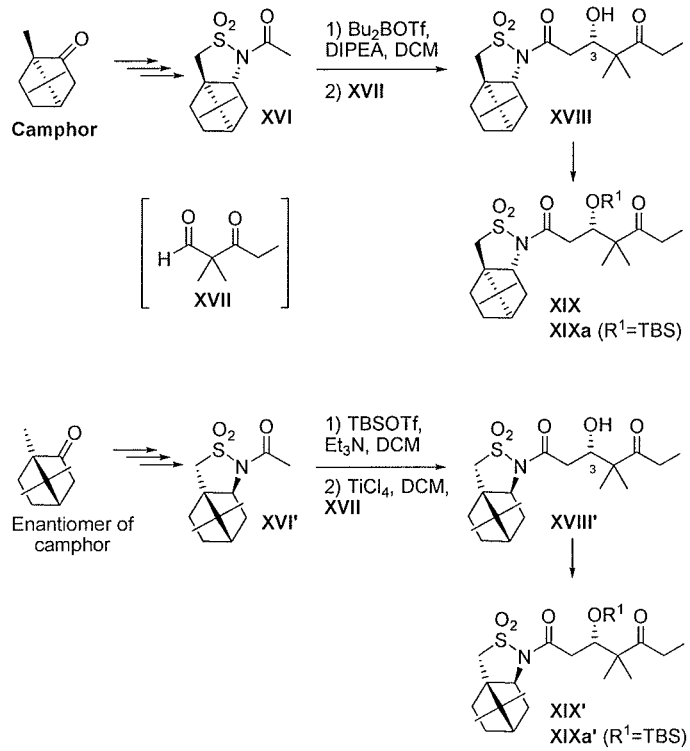
FIG. 7 provides Scheme 7, illustrating the synthesis of Unit A.
Figure 8:
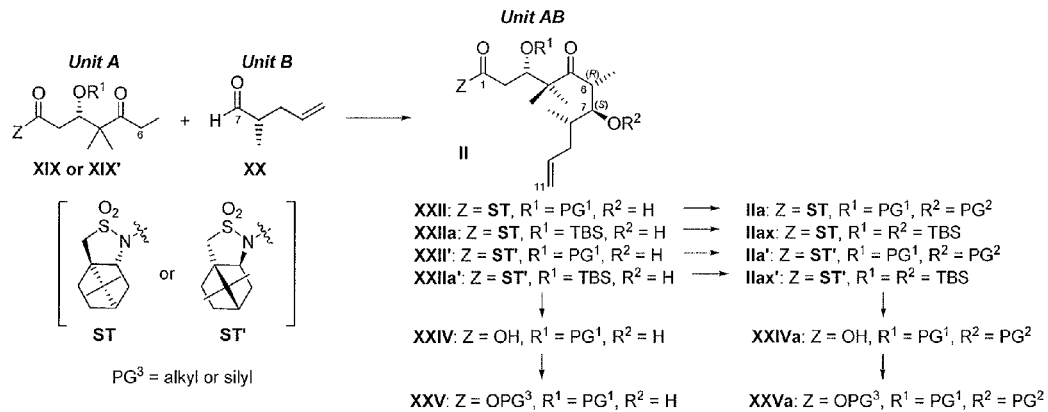
FIG. 8 provides Scheme 8, illustrating the synthesis of Unit AB (II).
Figure 9:
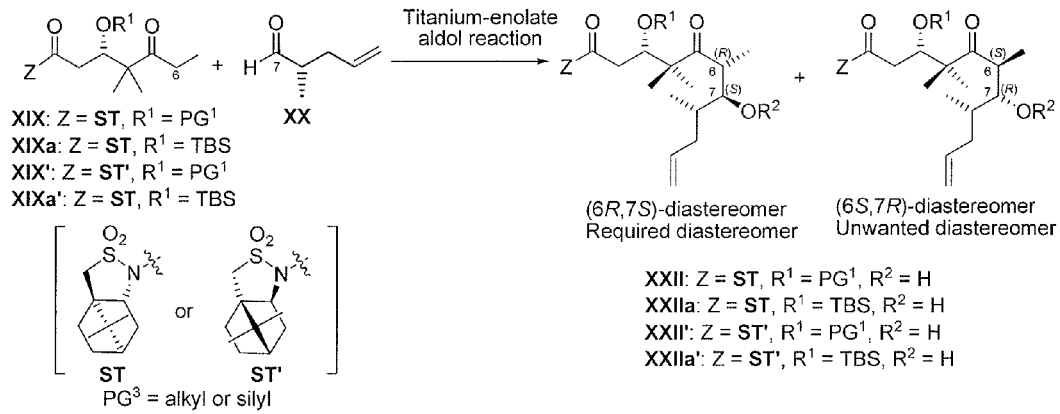
FIG. 9 provides Scheme 9, illustrating the preparation of two major diastereomers of XXII or XXII' formed in the titanium-enolate aldol reaction of XIX or XIX' and XX.
Figure 10:
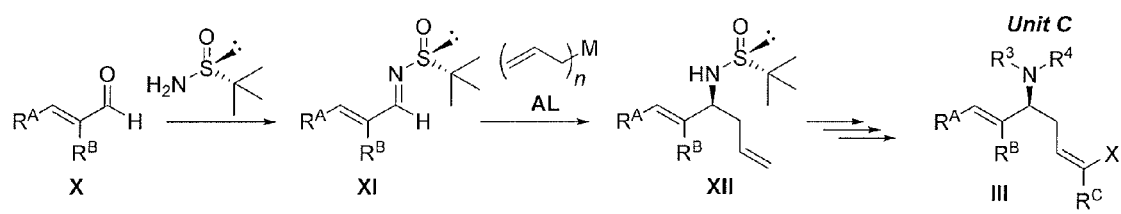
FIG. 10 provides Scheme 10, illustrating the synthesis of Unit C (III).
Figure 11:
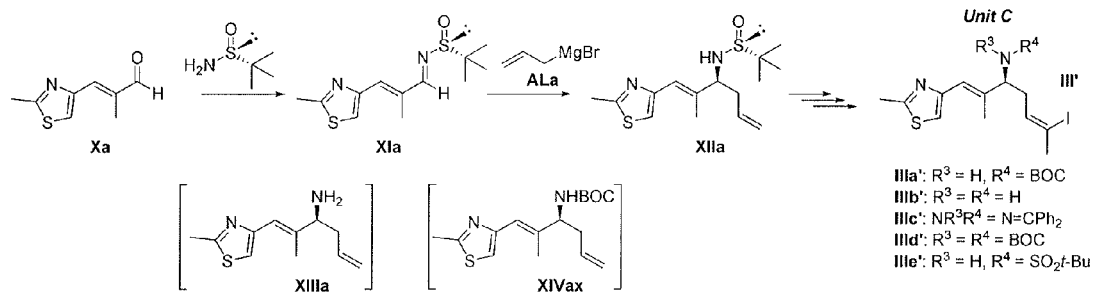
FIG. 11 provides Scheme 11, illustrating the synthesis of IIIa-e.
Figure 12:
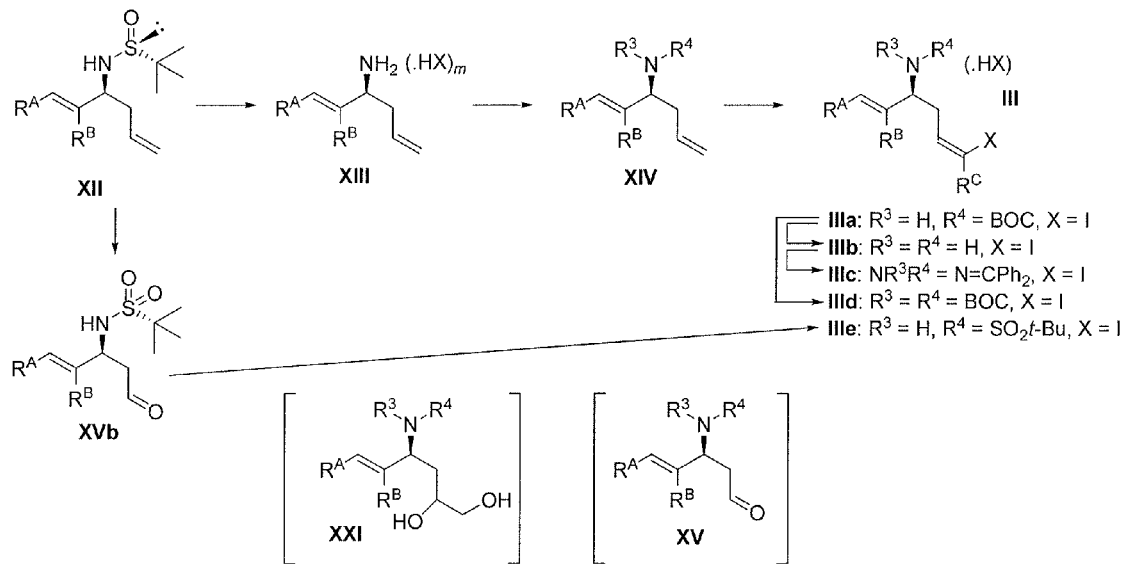
FIG. 12 provides Scheme 12, illustrating the conversion of XII to IIIa-e.
Figure 13:
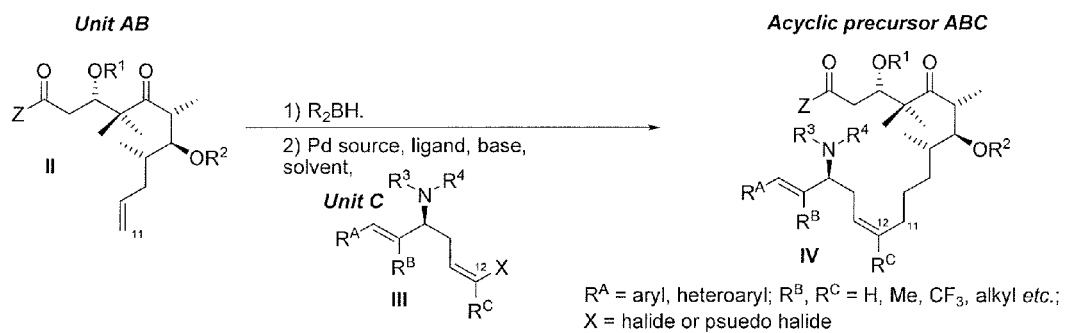
FIG. 13 provides Scheme 13, illustrating the synthesis of acyclic precursor ABC.
Figure 14:
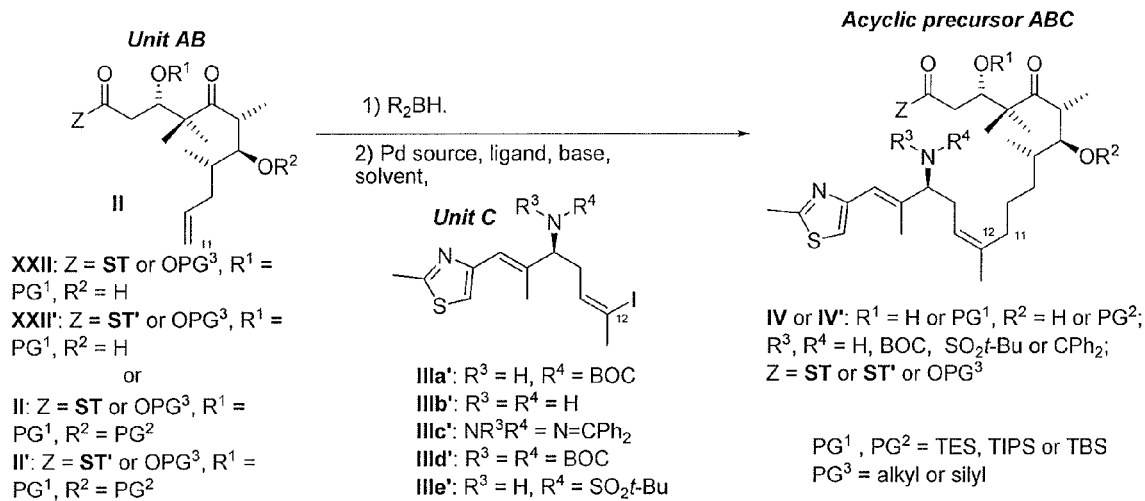
FIG. 14 provides Scheme 14, illustrating the synthesis of intermediates IVax and IVax' useful for the synthesis of aza-epothilones including ixabepilone.
Figure 15:
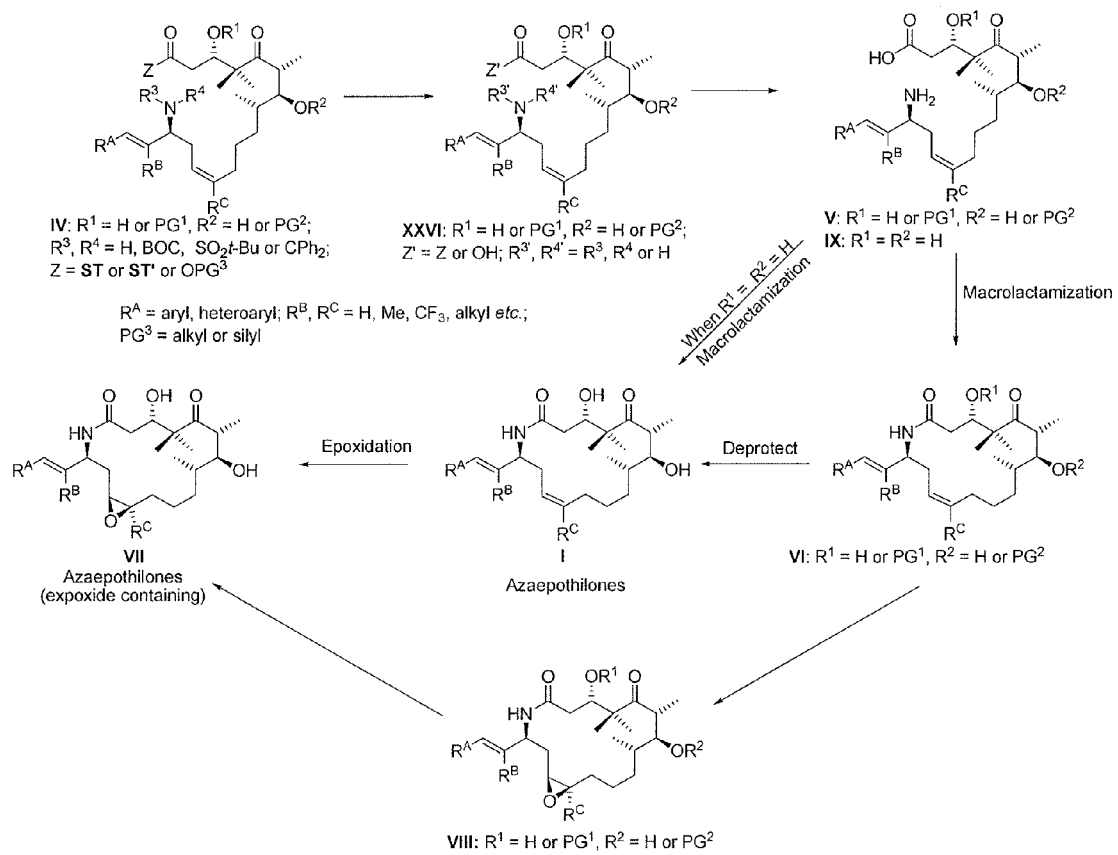
FIG. 15 provides Scheme 15, illustrating the synthesis of azaepothilones from acyclic precursor ABC.
Figure 16:
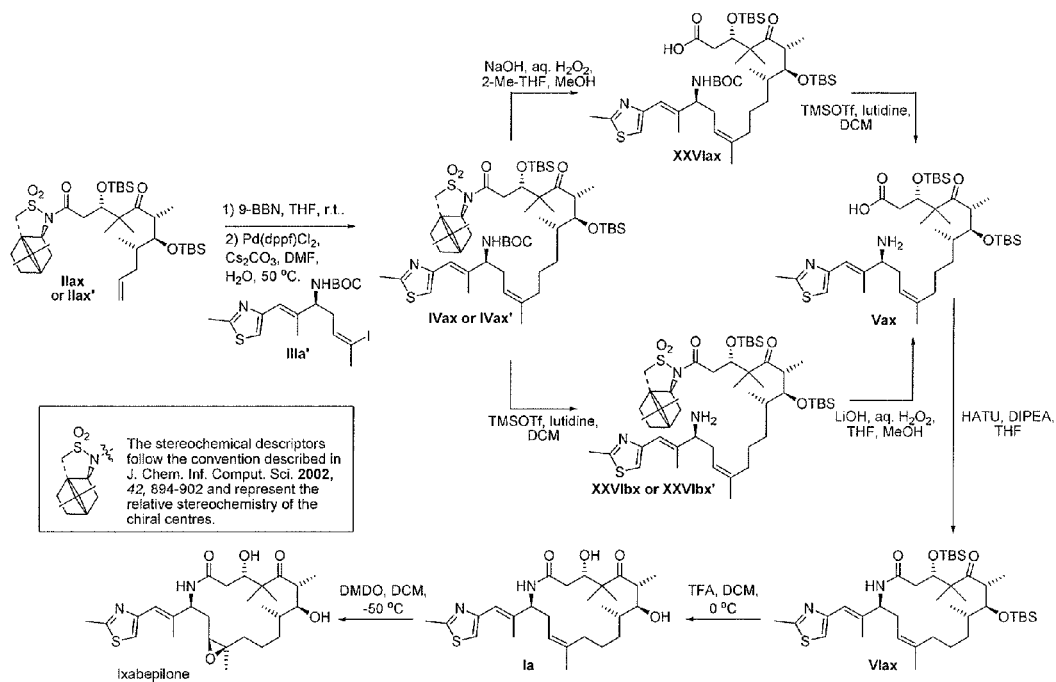
FIG. 16 provides Scheme 16, illustrating the synthesis of ixabepilone using methods described herein.
Figure 17:
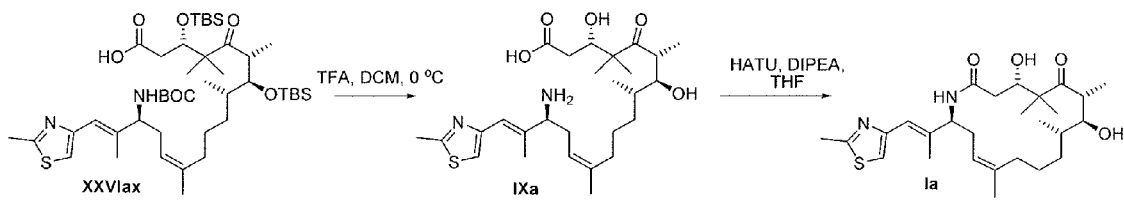
FIG. 17 provides Scheme 17, illustrating the synthesis of Ia from XXVIax, via IXa, using methods described herein.
Figure 18:
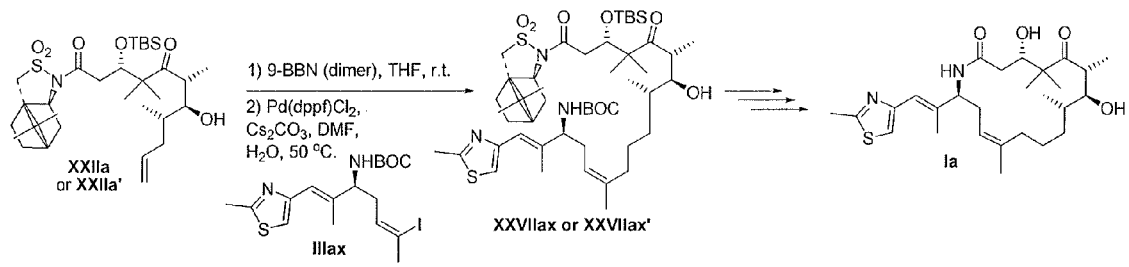
FIG. 18 provides Scheme 18, illustrating synthesis of Ia from partially protected intermediates XXII or XXIIa', using methods described herein.

The present invention provides novel processes for the industrial manufacture of ixabepilone, ixabepilone derivatives and analogues, and intermediates thereof. Salts and prodrugs of the compounds of this invention are also included. The ixabepilone, ixabepilone derivatives, and ixabepilone analogues of this invention are intended for the treatment of disease in humans.

II. Definitions

As used herein, the term "azaepothilone" refers to a 16-membered polyketide-type lactam belonging to the epothilone class.

As used herein, a macrolactam is a cyclic amide with 12 or more atoms comprising the ring.

As used herein, the terms "aryl" and "aromatic ring," by themselves or as part of another substituent, refer to a polyunsaturated, hydrocarbon group which can be a single ring or multiple rings (up to three rings) which are fused together or linked covalently. Non-limiting examples of aryl groups include phenyl, naphthyl and biphenyl. "Substituted aryl" groups can be substituted with one or more groups selected from halo, hydroxy, amino, alkylamino, amido, acyl, nitro, cyano, and alkoxy.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isooxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. "Substituted heteroaryl" groups can be substituted with one or more groups selected from halo, hydroxy, amino, alkylamino, amido, acyl, nitro, cyano, and alkoxy.

The term "alkyl," by itself or as part of another substituent, means, unless otherwise stated, a straight or branched chain hydrocarbon radical. Alkyl substituents, as well as other hydrocarbon substituents, may contain number designators indicating the number of carbon atoms in the substituent (i.e., $C_1$-$C_8$ means one to eight carbons), although such designators may be omitted. Unless otherwise specified, the alkyl groups of the present invention contain 1 to 10 carbon atoms. For example, an alkyl group can contain 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 or 5-6 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

As used herein, the term "fluoroalkyl" refers to alkyl group containing one or more fluorine substituents. In some embodiments, fluoroalkyl refers to an alkyl group wherein all hydrogen atoms have been replaced with fluorine atoms. Examples of fluoralkyl include trifluoromethyl, 2,2,2-trifluoroethyl, and the like.

As used herein, the term "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl.

As used herein, the term "contacting" refers to the process of bringing into contact at least two distinct species such that they can react. It should be appreciated, however, that the resulting reaction product can be produced directly from a reaction between the added reagents or from an intermediate from one or more of the added reagents that can be produced in the reaction mixture. As used herein, the term "treating" refers to contacting a substance with at least one other substance.

As used herein, the term "borane derivative" refers to a compound having at least one carbon-boron bond. Borane derivatives include, but are not limited to, boronic acids, alkyl boranes, alkenyl boranes, vinyl boranes. A borane derivative can be formed via reaction of a borane having a formula $R_2BH$ with a suitable parent molecule such as an alkene. A borane derivative can be isolated and purified before conversion to another compound, or it can be used in situ without isolation and purification.

As used herein, the term "borane" refers to a compounding containing a boron atom bound to three substituents. In some embodiments, the borane is an alkylborane containing one or more alkyl substituents. Examples of boranes include, but are not limited to, 9-borabicyclo-[3.3.1]nonane (9-BBN), 9-borabicyclo[3.3.1]nonane dimer (9-BBN dimer), disiamylborane, and dicyclohexylborane.

As used herein, the term "protecting group" refers to a moiety that is formed to render a functional moiety unreactive. Forming the moiety is referred to as "protecting" the functional moiety or the molecule that contains the functional moiety. The protecting group can be removed so as to restore the functional moiety to its original state. Removing the protecting group is referred to as "deprotecting." Various protecting groups and protecting reagents, including hydroxy protecting groups, are well known to one of ordinary skill in the art and include compounds that are disclosed in *Protective Groups in Organic Synthesis*, 4th edition, T. W. Greene and P. G. M. Wuts, John Wiley & Sons, New York, 2006, which is incorporated herein by reference in its entirety.

As used herein, the term "vinyl halide" refers to any alkene containing a halogen atom bound to one of the unsaturated carbon atoms in the alkene double bond.

As used herein, the term transition metal refers to an element characterized by atoms having an incomplete d subshell or giving rise to cations having an incomplete d subshell. Examples of transition metals include Sc, Ti, V, Cr, Mn, Fe, Co, Ni, Cu, Zn, Y, Zr, Nb, Mo, Tc, Ru, Rh, Pd, Ag, Cd, Hf, Ta, W, Re, Os, Ir Pt, Au, Hg, Rf, Db, Sg, Bh, Hs, Mt, Ds, Rg, Cn. Lanthanides and actinides can also serve as transition metals in the methods of the present invention.

As used herein, the term "transition metal catalyst" refers to a compound containing at least one transition metal that participates in a chemical reaction so as to change the rate of the reaction. In general, the transition metal catalyst increases the rate of the reaction and is itself not consumed during the course of the reaction. The transition metal catalyst can be in elemental form, such as palladium black, or the transition metal catalyst can be a coordination complex containing a transition metal bound to one or more ligands.

As used herein, the term "epoxide" refers to a three-membered ring containing one oxygen atom and two carbon atoms. In general, the epoxides of the present invention are formed by contacting a precursor such as an alkene with a suitable epoxidizing agent. Examples of epoxidizing agent include, but are not limited to, peroxyacids such as peracetic acid and 3-chloroperbenzoic acid.

As used herein, the term "solvent" refers to a substance that is liquid at ambient temperature and pressure. Examples of solvents include water, acetone, toluene, methylene chloride, ethyl acetate, acetonitrile, tetrahydrofuran, benzene, chloroform, diethyl ether, dimethyl formamide, dimethyl sulfoxide, and petroleum ether.

As used herein, the term "allyl" refers to moiety having a formula: —$CH_2$—CH=$CH_2$.

As used herein, the term "halogen" refers to fluorine, chlorine, bromine, and iodine. The term "halide" refers to a compound containing a halogen or an anion originating from a parent halogen.

As used herein, the term "benzophenone" refers to a ketone substituted with two benzene groups at the carbonyl carbon. "Benzophenone imine" refers to the imine that would result from the reaction of ammonia and benzophenone. "Benzophenone dialkyl acetal" refers to an acetal that would result from the reaction of benzophenone with two equivalents of an alkyl-alcohol. The benzophenone imines and benzophenone dialkyl acetals can also be obtained via other reactions.

As used herein, the term "activating" refers to increasing the reactivity of a functional group toward a desired reaction partner. Activating a functional group can include forming an intermediate that is more reactive toward the reaction partner than the parent functional group. In some embodiments, for example, activating a carbonyl-containing compound includes forming a silyl enol ether.

As used herein, the term "Lewis acid" refers to a compound that can accept an electron pair from a second compound, i.e., a Lewis base, to form an acid-base adduct. Examples of Lewis acids include, but are not limited to, metal halides such as titanium tetrachloride ($TiCl_4$), zinc dichloride ($ZnCl_2$), and tin di- and tetrachlorides ($SnCl_2$ and $SnCl_4$); boron trifluoride ($BF_3$); aluminum and alkylaluminum halides ($AlX_3$ and $R_nAlX_{3-n}$), and phosphorus and antimony pentafluorides ($PF_5$ and $SbF_5$).

As used herein, the term "base" refers to a molecule that is capable of accepting a proton (i.e., a hydrogen cation) to form a conjugate acid of the base. Examples of bases include, but are not limited to, Hunig's base (i.e., N,N-diisopropylethylamine), lutidines including 2,6-lutidine (i.e., 2,6-dimethylpyridine also sometimes referred to a lutidine), triethylamine, and pyridine.

As used herein, the term "diastereomers" refers to two or more stereoisomers of a compound that are not related to each other as mirror images (i.e., not enantiomers). The term "diastereomeric ratio" refers to the ratio of one diastereomer to one or more other diastereomers in a mixture of diastereomers.

The term sultam refers to a cyclic sulfonamide compound in which the S—N chemical bond forms part of the ring. As used herein, the term sultam refers to the cyclic sulfonamides (1R)-(+)-2,10-camphorsultam or (1S)-(−)-2,10-camphorsultam, or derivatives of these compounds, otherwise known as camphorsultam or Oppolzer's sultam, which are derived from camphor or the enantiomer of camphor. These sultam are used as chiral auxiliaries in the invention described herein.

III. Description of the Embodiments

The synthetic approach to the macrolactam compounds of the invention involves the sequential coupling together of three starting materials (referred herein as units). The building blocks are the ketone referred to as Unit A, such as XIX or its diastereomer XIX', the aldehyde referred to as Unit B, XX, and the amino vinyl iodide referred to as Unit C, such as III. These units are coupled to form linear, acyclic precursor molecules IV, referred to as Unit ABC. The linear, acyclic precursor compounds are chemically manipulated to remove protecting groups and then cyclised to give macrolactam compounds (i.e., VI and I) that themselves can be useful as therapeutic agents or can undergo further synthetic manipulations to produce other therapeutic agents, including the epoxide-containing macrolactam compound ixabepilone which is a known therapeutic agent, where necessary. This synthetic strategy is summarized in Scheme 6.

A. Process for Unit A

Unit A can be N-((3S)-3-oxy-5-oxo-heptanoyl)-bornane-10,2-sultam XVIII or XVIII', or C3 hydroxy protected derivatives XIX or XIX'. In preferred embodiments, Unit A is the ketone XIX or its diastereomer XIX', wherein $R^1$ is a silyl protecting group (such as triethylsilyl (TES), triisopropylsilyl (TIPS), tert-butyldimethylsilyl (TBS) and tert-butyldiphenylsilyl (TBDPS)). XIX can be prepared using methods known in the art (see for example *Helv. Chim. Acta* 2002, 85, 4086-4110). In more preferred embodiments, Unit A is the ketone XIX' wherein $R^1$ is a silyl protecting group (such as triethylsilyl (TES), triisopropylsilyl (TIPS), tert-butyldimethylsilyl (TBS) and tert-butyldiphenylsilyl (TBDPS)). Ketone XIX' can be prepared using methods disclosed herein (Scheme 7). When $R^1$ is the same protecting group in XIX and XIX', ketones XIX and XIX' are a diastereoisomeric pair of stereoisomers.

In the art it is known that XIX can be prepared from XVIII by blocking the hydroxyl group C3-OH. It is known in the art (see *Helv. Chim. Acta* 2002, 85, 4086-4110) that XVIII can be prepared by the treatment of commercially available sultam XVI with the Lewis acid diethylboron triflate, followed by treatment with diethylisopropylamine, followed by cooling to −75° C. and reaction with aldehyde XVII. Diethylboron triflate is an expensive reagent. As described herein, new intermediates XIX', where $R^1$ is a silyl protecting group, such as TES, TIPS, TBS or TBDPS, can be prepared using more cost efficient conditions. In this method, a mixture of aldehyde XVII and the Lewis acid $TiCl_4$ at −78° C. in an organic solvent, preferably dry dichloromethane (DCM), is reacted with the enantiomer of XVI, namely N-acetylcamphorsultam (N-acetylbornane-10,2-sultam) XVI', that had been activated in an organic solvent, preferably dry DCM, by pre-treatment with a silyl triflate, such as TBSOTf (tert-butyldimethylsilyl triflate), in the presence of an amine base such as $Et_3N$ (triethylamine) or 2,6-lutidine. Other Lewis acids (such as $BF_3$ etherate, lanthanide triflates (such as $Yb(OTf)_3$), transition metal triflates (such as $Sc(OTf)_3$), magnesium(II) salts, zinc (II) salts, other Ti(IV) salts or TMSOTf (trimethylsilyl trifluoromethanesulfonate)) are also known to be useful in similar Mukaiyama aldol reactions. When the Mukaiyama aldol reaction of activated XVI' with aldehyde XVII is complete an aqueous workup is conducted and then XVIII' can be isolated using methods known in the art. In contrast to that for other aldehydes, the reaction of aldehyde XVII with N-acetylcamphorsultam XVI provides the opposite stereochemistry of the chiral alcohol located at C3 of the heptanoyl chain. Therefore, to obtain the desired stereochemistry, the opposite enantiomer of the N-acetyl sultam XVI from that that would be anticipated must be used. That is, in the new method N-acetyl sultam XVI' is used.

Therefore, when using this alternative approach the product obtained, XVIII', is a diastereomer of compound XVIII, that would be obtained when applying the Lewis acid $Bu_2BOTf$ using known methods. The key chiral center at C3, which is present in the macrolactam products of this invention, is the same in both XVIII and XVIII'. XVIII' can be reacted with silylating agents such as triethylsilyl chloride (TESCl), triisopropylsilyl chloride (TIPSCl), tert-butyldimethylsilyl chloride (TBSCl), tert-butyldimethylsilyl triflate (TBSOTf) or tert-butyldiphenylsilyl triflate (TBDPSOTf) to provide XIX' where $R^1$=TES, TIPS, TBS or TBDPS, respectively. Both XIX and XIX' can be used as building blocks (i.e., Unit A) for the preparation of ixabepilone, ixabepilone analogues and intermediates thereof. As described herein, when synthesizing ixabepilone it is preferred that Unit A is the compound of formula XIXa' (N-((3S)-3-(tert-butyldimethyl) silyloxy-5-oxo-heptanoyl)-bornane-10,2-sultam).

B. Reaction of Unit B with Unit A

Unit AB, II, is a composite of Unit A and Unit B and comprises a N-((3S)-3,7-dioxy-5-oxo-undec-10-enoyl)-bornane-10,2-sultam moiety. II can be the partially hydroxy-protected compounds XXII or XXII' or the fully hydroxy-protected compounds IIa or IIa'. The partially protected and fully protected compounds can all be used in the preparation of ixabepilone, the ixabepilone analogues, and the intermediates of this invention. Also as provided herein, it is more preferable to use fully protected compounds IIa or IIa', such as where $R^1$=TBS and $R^2$=TBS, when preparing ixabepilone, and it is further preferred to use IIax' (where $R^1$=TBS and $R^2$=TBS) than to use IIax. The use of IIa' is more preferred than the use of IIa as the doubly TBS-protected compound IIax' can be more readily isolated as a crystalline solid, making its purification more convenient, more efficient and less costly, on a manufacturing scale.

Unit AB (II) can be prepared by the aldol reaction of ketone XIX or XIX' and aldehyde XX (Scheme 8). $R^1$ and $R^2$ are independently H (hydrogen) or a protecting group $PG^1$ and $PG^2$. The protecting groups are preferably silyl protecting groups, such as TES, TIPS, TBS or TBDPS for example. Examples of Unit AB are compounds of the formula XXII, XXII', IIa, or IIa'. IIa and IIa' are prepared by further protection of XXII and XXII'. In preferred embodiments $R^1$ is TBS and $R^2$ is H or TBS, and Z can be sultam ST or its antipode sultam ST' and therefore in these preferred embodiments compounds IIa and IIa' are IIax and IIax', respectively. More preferably Unit AB is the compound of formula IIax'.

In preferred embodiments a diastereoselective aldol reaction of Unit A and Unit B is used such that the major reaction Unit AB products, compounds of formula II (which is embodied as compounds of formula XXII and XXII'), possesses the requisite (6R,7S)-stereochemistry. More preferably the aldol reaction is the condensation reaction of ketone XIXa' and aldehyde XX and the major product is the compound of formula XXIIa'. Unit B is the aldehyde compound of formula XX. Aldehyde XX can be prepared using methods reported in the arts (see for example, *Org. Lett.* 2009, 11, 5326-5328). Good stereoselectivity in the titanium enolate aldol reaction of ketone XIX, where $R^1$ is TBS, with α-methyl aldehydes has been reported (for example, see *Org. Lett.* 2002, 4, 3811-3814; *J. Org. Chem.* 2004, 69, 9269-9284). Stereo selection (which are reported as diastereomeric ratios (d.r.)) for the (6R,7S)-diastereomer over the (6S,7R)-diastereomer with d.r. of as high as 10:1 to 20:1 have been reported (see *Org. Lett.* 2002, 4, 3811-3814; *J. Org. Chem.* 2004, 69, 9269-9284) for the titanium enolate aldol reaction of ketone XIX, where $R^1$ is TBS with α-methyl aldehyde XXIIIa and XXIIIb. α-Methyl aldehydes XXIIIa and XXIIIb have been proposed to be intermediates for the synthesis of epothilone B and D. The use of these titanium enolate aldol reaction, however, for the coupling of sultam-containing ketones XIX or XIX', with aldehyde XX has not been reported for the preparation of intermediates useful in azaepothilone synthesis.

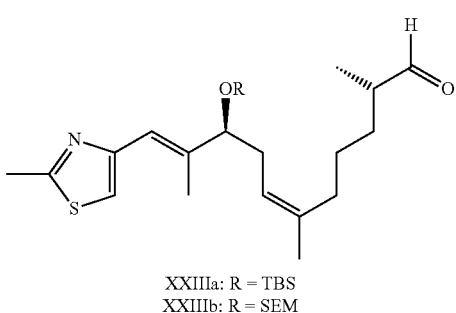

XXIIIa: R = TBS
XXIIIb: R = SEM

The diastereoselective titanium-enolate aldol reaction of ketones XIX or XIX' and aldehyde XX as described herein can be conducted using reaction conditions reported in the arts for titanium-enolate aldol reaction of ketones and aldehydes. The ketone XIX or XIX' is activated by treatment with a titanium-based Lewis acid such as $TiCl_4$ or $TiBr_4$, preferably $TiCl_4$, at a low temperature, preferably colder than $-50°$ C. more preferably colder than $-70°$ C. and most preferably between about $-70$ to $-78°$ C., in an organic solvent, preferably DCM, followed by addition of an amine base, such as DIPEA (N,N-diisopropylethylamine; Hünig's base), $Et_3N$, $Bu_3N$, preferably DIPEA. Following activation of the ketone, the aldehyde is added to the activated ketone mixture that is maintained at a low temperature, preferably colder than $-50°$ C., more preferably colder than $-70°$ C., and most preferably between about $-73$ to $-78°$ C. The aldehyde XX is added either neat (no solvent) or in an organic solvent such as DCM, pentane, hexanes, petroleum ether, or n-heptane, or in a mixture of organic solvents, such as DCM and n-heptane. Some solvents, including THF (tetrahydrofuran), when present at high enough levels can inhibit the aldol reaction of XIX or XIX' and XX in this invention and therefore should be avoided. The molar equivalents of aldehyde XX can be varied with respect to ketone XIX or XIX', however, it has now been found that at least 1.5 molar equivalents of aldehyde XX should be used, and more preferably more than 3 molar equivalents of aldehyde XX should be used to allow good conversion of the ketone XIX or XIX' to the product XXII and XXII'. Most preferably about 4 molar equivalents of aldehyde XX are used to ensure good chemical conversion of ketones XIX or XIX' to XXII or XXII', respectively. Following addition of the aldehyde, the reaction mixture can be held at a low temperature (between about $-70$ to $-78°$ C.) for a period of time, or allowed to warm up to about $0°$ C. before reaction workup to isolate the product XXII and XXII'.

The diastereoselective titanium-enolate aldol reaction of XIX or XIX' and XX in this invention provides different diastereomeric ratios (d.r.) of the products XXII or XXII', respectively (Scheme 9). For example, the aldol reaction of XIXa and XX provides XXIIa with a d.r. of the (6R,7S)-diastereomer/(6S,7R)-diastereomer of about 91:9, up to about 95:5, whereas the aldol reaction of XIXa' and XX provides XXIIa' with a d.r. of the (6R,7S)-diastereomer/(6S, 7R)-diastereomer of about 84:16, up to about 86:14.

In preferred embodiment, the isolated XXIIa' (which is the compound of formula XXII' where $R^1$ is TBS and $R^2$ is H) does not require purification and can be used in the next reaction step to provide IIax' (which is the compound of formula IIa' where $R^1$ is TBS and $R^2$ is TBS). The compound of formula IIa', where $R^2$ is a silyl protecting group, is prepared by silylation of XXIIa' under reaction conditions known in the arts for the silylation of secondary alcohols. In preferred embodiments the compound of formula XXIIa' is silylated by its reaction with TBSOTf (tert-butyldimethylsilyl triflate) in an organic solvent, preferably dry DCM, in the presence of a base, such as 2,6-lutidine or imidazole, more preferably 2,6-lutidine.

In embodiments where IIax is required, it is preferred that its precursor XXIIa is purified by crystallisation or by column chromatography prior to its silylation such that the unwanted (6S,7R)-diastereomer of XXIIa can be removed. Purification of XXIIa by crystallisation can be achieved using a mixture of MeOH (methanol) and water. Purification of XXIIa by column chromatography to remove the unwanted (6S,7R)-diastereomer of XXIIa (leaving the d.r. of the isolated XXIIa at about 99:1) insures that IIax of high chiral purity can be obtained. The compound of formula IIa, can be purified by methods known in the art such as column chromatography. IIax of this invention can be obtained with a d.r. of about 99:1 when its precursor XXIIa is purified by column chromatography as just described.

In some preferred embodiments the solid compound IIax', is purified by recrystallisation from organic solvents including MeOH. Recrystallisation of crude IIax' from MeOH provides IIax' with a high chemical and chiral purity. The d.r. of the (6R,7S)-diastereomer/(6S,7R)-diastereomer of recrystallised IIax' is greater than or equal to 99:1. Multiple recrystallisation can provide an even higher d.r. of the (6R,7S)-diastereomer/(6S,7R)-diastereomer of recrystallised IIax'. Thus although both IIax and IIax' can be used in this invention for the manufacture of ixabepilone or its analogues and derivatives, IIax' is preferred due to its high chiral purity, and its convenience in manufacturing.

Consideration of the d.r. values for XXII or XXII' produced by the titanium-enolate aldol reaction of XIX or XIX' and XX, respectively, would suggest that XIX is the better building block, as opposed to XIX', for the manufacture of ixabepilone. Two unexpected factors, however, reveal that XIX' is more suitable than XIX for the manufacture of ixabepilone using the methods described herein. Firstly, while the natural product (+)-camphor, used in the chiral intermediates is an oil, XXII' and IIax' are both solid compounds. That is, while the compound IIax derived from the natural product (+)-camphor is an oil, the two of compounds (i.e., XXII' and IIax') derived from the unnatural enantiomer of (+)-camphor, are solids. The consequence of this difference in physical property of the diastereomeric compounds is that the manufacture of IIax' is more efficient than that of IIax. In fact, in preferred embodiments IIax' can be prepared with a greater than or equal to 99:1 diastereomeric ratio of the (6R,7S)-diastereomer/(6S,7R)-diastereomer and high chemical purity in greater than 60% overall yield from the coupling of XIXa' and XX followed by silylation and crystallisation, without the need for chromatographic purification. High chemical purity and diastereomeric purity of IIax' is readily achieved by crystallisation of IIax' from methanol. By contrast, IIax is produced in an oily physical form and the unwanted (6S,7R)-diastereomers must be removed by column chromatography. Therefore, in the manufacture of ixabepilone as described herein it is preferred that XIX', XXII' and IIax' are used as intermediates rather than the corresponding diastereomers XIX, XXII and IIax. Still other advantages, described below, are that the hydrolysis of the sultam-containing intermediate IVax', derived from IIax', provides XXVIax in higher yield than does the hydrolysis of the corresponding sultam-containing intermediate IVax, which is a diastereomer of IVax', and which is derived from IIax.

The sultam group (Z is sultam ST or sultam ST') of the compounds of formula II (Unit AB) can be removed and changed to oxygen-based groups such as alkyl esters or silyl esters. This can be achieved by hydrolysis of the amide bond of the compound of formula IIa or IIa' using methods known in the art (such as hydrolysis using LiOH or NaOH and $H_2O_2$, for example) to provide carboxylic acid derivatives of II, such as XXIVa, which are then esterified to provide esters (Scheme 8), such as XXVa, using methods known in the art. These esters can be used to prepare ixabepilone and its derivatives and analogues.

C. Preparation of Unit C

Unit C is represented by the generic formula III (Scheme 10). $R^A$ is an unsubstituted or substituted aryl group or an unsubstituted or substituted heteroaryl group, and is preferably the radical 2-methyl-thiazol-4-yl. $R^B$ and $R^C$ are independently alkyl, fluoroalkyl, an unsubstituted or substituted aryl group or an unsubstituted or substituted heteroaryl group, and are both preferably methyl. X is a halogen selected from the group I, Br and Cl, or a non-halogen such as triflate ($OSO_2CF_3$) or phosphate ($OPO(OR)_2$), and is preferably I. $R^3$ and $R^4$ are independently hydrogen (H) or a protecting group. In preferred embodiments for the preparation of macrolactam compounds of this invention III is compounds of the formula III', and in the preferred embodiments useful for the synthesis of ixabepilone, III is IIIa'. III can also be IIIb', IIId', IIIe', and IIIc'.

Compound IIIa' (see Scheme 11) can be prepared by known methods. Unfortunately the reported methods (see two methods reported in *J. Org. Chem.* 2001, 66, 4369-4378) for the synthesis of IIIa require long synthetic pathways and are low yielding. There therefore exists a need for new and more efficient routes that can be conducted on manufacturing scales. In this invention, III, embodied as IIIb', IIIa', IIId', IIIe', and IIIc', is prepared using novel methods that include the 1,2-addition of an allylating reagent AL to the C—N double bond of chiral N-sulfinyl imines XI as a key reaction step to provide chiral N-sulfinyl amines XII (Scheme 10) with high stereo purity. N-Sulfinyl imines XI can be prepared from α,β-unsaturated aldehydes X by condensation with tert-butanesulfinamide using conditions such as those provided in *Chem. Rev.*, 2010, 110, 3600-3740 or using methods described herein. For example, Xa can be reacted with (R)-(+)-N-tert-butanesulfinamide in dry solvents, preferably in dry toluene, in the presence of activating agents such as Ti(Oi-Pr)$_4$, Ti(OEt)$_4$, MgSO$_4$, CsCO$_3$ or KHSO$_4$, most preferably in the presence of KHSO$_4$, at room temperature for several hours followed by aqueous workup and concentration under vacuum to provide XIa. In the subsequent reaction step, the atom M of the allylating reagent AL can be a metal or a metalloid useful in 1,2-additions to C—N double bonds including Mg, Zn, In, Li, Sn, Ce, Al, B, lanthanides or Si. Magnesium is more preferred due to high stereoselectivities (≥98% d.e. (diastereomeric excess)) that can be obtained in the 1,2-addition reaction. When M is a metal such as Zn, metal salts such as InCl$_3$ and In(OTf)$_3$ can be added to the reaction mixture. The value of n in the formula AL can be 1, 2, 3 or 4, but preferably is 1. For example, a solution in a dry organic solvent such as DCM, diethyl ether, THF or 2-Me-THF (2-methyltetrahydrofuran), more preferably a solution in dry DCM or dry 2-Me-THF, of XIa can be reacted with allyl magnesium bromide, ALa, in diethyl ether or in 2-Me-THF, more preferably in 2-Me-THF, at about <−40° C. Although allyl magnesium bromide in diethyl ether is commercially available, improved stereoselectivity in the conversion of XIa to XIIa can be achieved in this reaction when allyl magnesium bromide is prepared in 2-Me-THF. It is therefore preferred that allyl magnesium bromide in 2-Me-THF is used in this reaction. Once the 1,2-addition reaction of the allylating reagent and imine derivative XI is complete, the product mixture can be treated with a mild aqueous acid, such as saturated aqueous ammonium chloride, at about −20° C. followed by warming to room temperature. Following an aqueous workup, XIIa can be isolated, and optionally purified by methods known in the arts including precipitation or column chromatography. In the preferred embodiments of this invention, XIIa can be isolated with a high chemical purity and a high diastereomeric purity (d.e.), such as ≥99% d.e., as a solid compound by precipitating it from a solution of MTBE (methyl tert-butyl ether) and n-heptane. Additionally, allyl derivatives of metalloids, such as boron and silicon, might be useful on their own or in the presence of activating agents such as Lewis acids, such as TMSOTf, Ti(IV) and Al(III) salts, or TBAF (tetra-N-butylammonium fluoride) or MeLi, as replacements for the allylating reagent AL.

In one embodiment of the invention, the allylating reagent AL is allyl magnesium bromide (ALa), III is any of IIIb', IIIa', IIId', IIIe', or IIIc' (Scheme 11), and is preferably IIIb', IIIa', or IIId', more preferably IIIb' or IIIa', and most preferably IIIa'. All of these compounds can be prepared from the commercially available compound Xa, using methods disclosed herein. IIIa' is useful for the manufacture of ixabepilone and its derivatives and analogues using methods described herein.

The conversion of XII to compounds of the general formula III of this invention can be accomplished in several ways (Scheme 12). For example, removal of the sulfinyl chiral auxiliary of XII using a strong acid provides allyl amine XIII that can be obtained as a free base or as a salt (such as a HCl, p-toluenesulfonic acid, camphorsulfonic acid, citric acid or (L)-(+)- or (D)-(−)-tartaric acid salt). Protection of the nitrogen atom of the free base or salt forms of XIII provides XIV. XIV can then be homologated via a one-pot, two-step oxidation and Wittig reaction (see *J. Am. Chem. Soc.* 2000, 122, 10521-10532), to provide the vinyl halides III.

For example, treatment of XIIa in an organic solvent such as MeOH or 1,4-dioxane, preferably MeOH, with a solution of HCl in an ether solvent such as diethyl ether or 1,4-dioxane, preferably in diethyl ether, at room temperature, provides an organic solvent solution of the hydrochloride salt (HCl) of allyl amine XIIIa. Neutralization of the hydrochloride salt of allyl amine XIIIa can be conducted with a base, such as aqueous NaOH, to provide allyl amine XIIIa that can be used without further purification in the subsequent reaction step, or alternatively it can be purified such as by column chromatography. Alternatively, treatment of XIIa in MeOH with concentrated aqueous HCl at about room temperature provides the hydrochloride salt (HCl) of allyl amine XIIIa, which is then extracted into water, mixed with an organic solvent, such as MTBE, and treated with 10% aqueous NaOH until the pH increases to about 10-11. Washing of the organic phase with water and brine provides an organic solution which is then concentrated under reduced pressure to provide allyl amine XIIIa with good chemical purity. The allyl amine XIIIa can be converted to its N-tert-butoxycarbonyl (N—BOC) protected derivative XIVax by treatment with di-tert-butyl dicarbonate (also known as BOC anhydride or BOC$_2$O) in an organic solvent such as THF, 2-Me-THF or DCM, preferably DCM, optionally in the presence of a base, such as Et$_3$N. Preferably XIIIa in DCM is reacted with di-tert-butyl dicarbonate in the absence of a base and following completion of the reaction the product mixture is concentrated and XIVax is precipitated in high yield and high chemical purity by the addition of n-heptane.

In one embodiment, the olefin XIV can be converted to aldehyde XV by a one-pot/two-step dihydroxylation and oxidation reaction sequence without isolation of the dihydroxylated reaction intermediate XXI. This sequence involves the dihydroxylation of the double bond of XIV using a first oxidant to provide dihydroxy compound XXI. The first oxidation can be an oxidant such as $H_2O_2$, t-BuOOH, DMDO (dimethyldioxirane), m-CPBA (meta-chloroperoxybenzoic acid) or metallic conditions such as using catalytic or stoichiometric amount of Rh, Ru, Pt, Pd, Cu, Ce or Os salts in combination with other oxidants such as periodates or peroxides in the presence or in the absence of ligands in one step, and is preferably a combination of a catalytic amount of an osmate reagent and 4-methylmorpholine N-oxide using solvents such as water, ketones, alcohols, ethers, nitriles or ionic liquids or any combination of these but more preferably a mixture of acetone and water. When the reaction is deemed to have reached a satisfactory level of completion, as determined by analytical techniques such as HPLC analysis, an agent is added to the product mixture that retards or deactivates the oxidative ability of the osmium salt. This deactivating agent is preferably a Lewis base, such as pyridine or a pyridine derivative such as N,N-dimethyl-4-aminopyridine (DMAP). This deactivation is necessary to inhibit oxidation of the remaining double bond in the second reaction step (i.e., in the conversion of dihydroxy compound XXI to aldehyde XV). Following addition of the deactivating agent, a second oxidant is added to the mixture, without isolation of the dihydroxy compound XXI, to effect conversion of the dihydroxylated intermediate XXI to aldehyde XV. The second oxidant can be $NaIO_4$, $HIO_4$, $PbI(OAc)_2$ or $Pb(OAc)_4$, and is preferably $NaIO_4$ using solvents such as water, ethers, dioxane, nitriles, EtOAc (ethyl acetate) or chlorinated hydrocarbons but more preferably a mixture of acetone and water. This reaction sequence provides an advantage on manufacturing scale because the dihydroxy intermediate XXI does not require isolation, but instead can be directly converted into aldehyde XV in the same reaction vessel using the same solvents upon addition of the second oxidant.

In another embodiment of the conversion of olefin XIV to aldehyde XV, dihydroxylation of the double bond of XIV is accomplished using an oxidant to provide dihydroxy compound XXI. The oxidant can be an oxidant such as $H_2O_2$, t-BuOOH, DMDO, m-CPBA or metallic reagents such as a catalytic or stoichiometric amount of Rh, Ru, Pt, Pd, Cu, Ce or Os salts in combination with other oxidants such as periodates or peroxides in the presence or in the absence of ligands, and is preferably a combination of a catalytic amount of an osmate reagent and 4-methylmorpholine N-oxide in the presence of $(DHQ)_2PHAL$ using solvents such as a mixture of THF and water. The dihydroxy compound XXI is then isolated and purified using techniques known in the arts such as crystallisation or chromatography. The purified dihydroxy compound XXI is then oxidized to provide aldehyde XV using an oxidant. The oxidant can be $NaIO_4$, $HIO_4$, $PbI(OAc)_2$ or $Pb(OAc)_4$, and is preferably $NaIO_4$ using solvents such as water, ethers, dioxane, nitriles, EtOAc or chlorinated hydrocarbons but more preferably a mixture of THF and water.

The conversion of the compound of formula XV to the compound of formula III is achieved by a Wittig reaction using the ylide generated from (1-iodoethyl)triphenylphosphonium iodide. (1-Iodoethyl)triphenylphosphonium iodide can be prepared from (ethyl)triphenylphosphonium iodide as described in *J. Am. Chem. Soc.* 2000, 122, 10521-10532, however, on multigram scales or larger scales, it has now been found that it is best that (1-iodoethyl)triphenylphosphonium iodide is isolated and purified prior to its use (*Org. Lett.* 2008, 10, 1353-1356). This contrasts with methods known in the art (such as *J. Am. Chem. Soc.* 2000, 122, 10521-10532) where (1-iodoethyl)triphenylphosphonium iodide is generated in situ and used directly in the next reaction step without its isolation. Thus, in preferred embodiments dry (ethyl)triphenylphosphonium iodide is deprotonated with a strong base, such a n-BuLi, in an organic solvent, such as THF or 2-Me-THF, at a temperature lower than ambient temperature, preferably about 0 to 10° C. After warming up to ambient temperature the deprotonated intermediate is then cooled to about −50 to −60° C. and is iodinated with an iodinating agent such as iodine. After warming up to ambient temperature the thus formed crude (1-iodoethyl)triphenylphosphonium iodide is isolated from the reaction slurry by filtration. Purification of the crude (1-iodoethyl)triphenylphosphonium iodide is preferred because it provides better efficiency in the subsequent reaction step. Purification of the crude (1-iodoethyl)triphenylphosphonium iodide can be achieved by stirring a slurry of the crude (1-iodoethyl)triphenylphosphonium iodide in an organic solvent for a sufficient period of time and then filtering. The organic solvent is one that preferentially can dissolve the impurities whilst not substantially dissolving (1-iodoethyl)triphenylphosphonium iodide. Preferred solvents include DCM or MeCN (acetonitrile). This slurry process effects the removal of certain impurities, such as unreacted (ethyl)triphenylphosphonium iodide, that can otherwise lead to impurity formation in the next reaction step. It is more preferred that this slurry purification is conducted in DCM because it has a low boiling point and is readily removed from the purified (1-iodoethyl)triphenylphosphonium iodide upon drying of the isolated solid.

Purified (1-iodoethyl)triphenylphosphonium iodide is dried using techniques known in the art, preferably in a vacuum oven, to remove any inadvertently absorbed moisture. The dried reagent is then mixed with an organic solvent, such as THF, 2-Me-THF, MeCN or toluene or a combination of 2-Me-THF with TPPA (tripyrrolidinophosphoric acid triamide), DMSO (dimethyl sulfoxide), DME (1,2-dimethoxyethane), diglyme, NMP (N-methyl-2-pyrrolidone), TMEDA (N,N,N',N'-tetramethylethylenediamine) or DMAc (dimethylacetamide), and reacted with a strong base, such as LiHMDS (lithium bis(trimethylsilyl)amide), NaHMDS (sodium bis(trimethylsilyl)amide), KHMDS (potassium bis(trimethylsilyl)amide) or n-BuLi (n-butyl lithium), at a temperature less than ambient temperature, such as at or below about −20° C. Following deprotonation of the (1-iodoethyl)triphenylphosphonium iodide with the strong base, the reaction temperature is lowered further, such as to about −50° C. or below, and the aldehyde XV, preferably dissolved in an organic solvent such as THF or 2-Me-THF, is added. Following completion of the reaction, a workup is conducted and III is isolated and preferably purified. When III is a solid, it is preferably purified by crystallisation. When III is a non-solid compound, such as is IIIa, it is preferably purified by column chromatography.

When the protecting group $R^4$ is tert-butyloxycarbonyl (BOC; t-BOC; Boc), $R^3$ is H, $R^A$ is a 2-methyl-thiazol-4-yl group and $R^B$ and $R^C$ is methyl and X is I, the generic formula III (Unit C) is the compound of formula IIIa'. The compound of formula IIIa' is useful for the manufacture of ixabepilone. Deprotection of $R^4$ of IIIa', using methods disclosed herein, provides allyl amine IIIb' which can be isolated in its free base form or as a salt (where HX is a Brønsted acid, H is a proton and X is a conjugate base, such as HCl for example in the compound of formula IIIb.HCl). Allyl amine IIIb' can be used for the manufacture of ixabepilone. Alternatively, allyl amine IIIb' can be reacted with benzophenone in the presence of a catalyst to provide benzophenone imine Alternatively, further BOC protection of IIIa', using methods disclosed herein, including deprotonation of IIIa' with a base such as NaHMDS and reacting the deprotonated form of IIIa' with di-tert-butyl dicarbonate, provides bis-BOC protected vinyl halide IIId'. Bis-BOC protected vinyl halide IIId' can be used for the manufacture of ixabepilone. Alternatively, oxidation of both the sulfur atom and double bond of XII, using methods disclosed herein, provides aldehyde XVb' that can then be homologated via a two-step oxidation and Wittig reaction sequence, to provide the vinyl halide IIIe' when $R^4$ is H, $R^B$ is methyl (Me) and $R^A$ is a 2-methyl-thiazol-4-yl group.

D. Preparation of Acyclic Precursor ABC

The acyclic precursor of ixabepilone and ixabepilone analogues of this invention, IV, are prepared by coupling of borane derivatives of alkenes II (Unit AB) with vinyl halides III (Unit C) by use of a carbon-carbon coupling reaction, such as a B-alkyl Suzuki reaction (Scheme 13). The B-alkyl Suzuki reaction is a metal catalysed carbon-carbon bond forming reaction. The borane derivatives, also known as alkyl boranes, of the alkene II that are used in the B-alkyl Suzuki reaction can be prepared by the reaction of the alkene with a borane including 9-borabicyclo-[3.3.1]nonane (9-BBN), 9-borabicyclo[3.3.1]nonane dimer (9-BBN dimer), disiamylborane, dicyclohexylborane, or other borane derivatives, using methods in the known art. 9-BBN, or its dimer, is the most preferred borane for hydroboration of IIa or IIa' that is useful in the coupling of IIa or IIa' and IIIa. The alkyl boranes produced upon hydroboration of IIa or IIa' can be used directly in the Suzuki reaction without the isolation or purification. The B-alkyl Suzuki reaction is well known in the arts (for example, see *J. Am. Chem. Soc.* 1989, 111, 314-321 and *Chem. Rev.* 1995, 95, 2457-2483). When the Suzuki reaction or the B-alkyl Suzuki reaction of alkenes II are employed according to the methods of the invention, the alkenes are first converted to their borane derivatives prior to the palladium-catalysed coupling step.

In one embodiment of the invention, III is any of IIIb, IIIa, IIId, IIIe, or IIIc, and is preferably IIIb, IIIa, or IIId, more preferably IIIb or IIIa, and most preferably IIIa, and this is coupled in the Suzuki reaction with a borane derivative of the alkene compounds XXII, XXII', IIa or IIa', most preferably a 9-BBN derivative of IIa', to give IV (Scheme 14). Preferably, $R^3$ and $R^4$ are H or BOC, while more preferably $R^3$ is H and $R^4$ is BOC. $R^1$ and $R^2$ are H or protecting groups, preferably silyl protecting groups including TES, TIPS, TBS and TBDPS, most preferably TBS. For the manufacture of ixabepilone, IIa' is more preferred than IIa as the sultam group ST' of IIa' can be removed more efficiently to provide carboxylic acid XXVIa than the sultam group ST of IIa. Most preferably, for the manufacture of ixabepilone, IIax' is coupled with IIIa' giving IV where Z is sultam ST', $R^1$ and $R^2$ is TBS, $R^3$ is H and $R^4$ is BOC and $R^A$ is 2-methyl-thiazol-4-yl, $R^B$ and $R^C$ is methyl.

The Suzuki reaction of the N—BOC amine derivative IIIa with the borane derivative of the olefin D2a was previously reported (*J. Org. Chem.* 2001, 66, 4369-4378) to give a 10% yield of D3a (see Scheme 5). In that report a low yield in the coupling of IIIa was obtained and thought to be due to the presence of the N—BOC carbamate group. An improved 63% yield was obtained upon substituting the N—BOC carbamate group of the vinyl iodide with an azide group. Surprisingly, as provided herein, the N—BOC amine derivative IIIa could be very efficiently coupled with the 9-BBN hydroborated derivatives of IIa or IIa'. In fact, isolated yields of IVax and IVax' (i.e., IV where $R^1$ is $R^2$ is TBS, Z is sultam ST or sultam ST', $R^3$ is H, $R^4$ is BOC) of >90% can be obtained using the present methods. Moreover, an arsenic-based ligand, triphenylarsine ($AsPh_3$) (as reported for the Suzuki reaction examples in *J. Org. Chem.* 2001, 66, 4369-4378), was not required in the coupling of N—BOC amine derivative IIIa with the 9-BBN hydroborated derivatives of IIa or IIa' as described herein. In short, a process has now been found wherein 9-BBN hydroborated derivatives of IIa or IIa' can be coupled with N—BOC amine derivative IIIa giving a high yield (≥90-98%) of IV without the need of azide derivatives, and without the need for an arsenic-based ligand ($AsPh_3$). For example, coupling of 1.3 molar equivalents of the 9-BBN hydroborated derivative of IIax' with IIIa' in the presence of 5 mol % of [1,1'-bis(diphenylphosphino)ferrocene]dichloropalladium(II) ($Pd(dppf)Cl_2$) without any additional phosphorous or arsenic-based ligands, and 3 molar equivalents of $Cs_2CO_3$ in N,N-dimethylformamide (DMF) at 50° C. provided up to a 98% isolated yield (following column chromatography) of IVax or IVax' after only 1 hour of reaction.

In addition to the Suzuki reaction of 9-BBN hydroborated derivatives of IIa and with IIa', it has also been found that the partially protected analogues XXII and XXII' could be coupled with N—BOC amine derivative IIIa. Although the use of partially protected analogues provide the advantage of not requiring an additionally protection step, the lack of protection of C7-hydroxyl group allows a retro-aldol reaction to occur that produces impurities and lowers the conversion yield. Therefore it is most preferred that both hydroxyl groups (i.e., C3- and C7-hydroxyl groups) are protected (that is, the use of IIa or IIa' in the Suzuki coupling step is preferred to the use of XXII or XXII'). Fully unprotected analogues (i.e., where both the C3- and C7-hydroxyl groups are not protected) are not preferred due to considerable levels of retro-aldol reaction occurring in the B-alkyl Suzuki reaction leading to low yields and impurity formation.

In addition to using the N—BOC amine derivative IIIa in the Suzuki reaction, other protected and unprotected amine analogues can be used. The unprotected free amine IIIb or its salt IIIb.HCl can be coupled with II (such as IIa or IIa') to provide IV where $R^3$ is $R^4$ and $R^4$ is H, but preferably the coupling is conducted in the presence of di-tert-butyl dicarbonate (($BOC)_2O$) which provides the N—BOC derivative of the product (i.e., IV where $R^3$ is H and $R^4$ is BOC) or a mixture of this and IV where $R^{3'}$ is $R^{4'}$ is H. IIId, IIIe, and IIIc can all be coupled with II using the Suzuki reaction to provide IV.

The acyclic precursor with the formula IV is then converted to the acyclic precursor amino acid compound of formula V by removal of the Z group and the nitrogen protecting groups $R^3$ and $R^4$ (when $R^3$ is not H) (Scheme 15). The removal of the Z group and protecting groups $R^3$ and $R^4$ (when $R^3$ is not H) can be conducted in either order (i.e., the Z group can be removed prior to $R^3$ and $R^4$ (when $R^3$ is not H) or vice versa) to provide intermediate XXVI. In embodiments where the Z group is an alkyl ester such as a tert-butyl ester or a silyl ester such as 2-(trimethylsilyl)ethoxymethyl (SEM), and $R^4$ (and $R^3$ if it is not H) is a Brønsted and/or Lewis acid sensitive protecting group such as BOC, the Z group is optionally removed simultaneously with the removal of $R^4$ (and $R^3$ if it is not H) using Brønsted acids such as trifluoroacetic acid (TFA) or Lewis acids such as trimethylsilyl trifluoromethanesulfonate (TMSOTf). Optionally, where the Z group is an alkyl ester such as a tert-butyl ester or a silyl ester such as SEM, it can be simultaneously removed during deprotection of $R^1$ and $R^2$ when $R^1$ and $R^2$ are silyl protecting groups such as TES, TIPS, TBS or TBDPS. In another embodiment, proceeding removal of the Z group, protecting groups $R^1$ and $R^2$ can be removed at the same time as $R^4$ (and $R^3$ if it is not H) such that the amino acid IX wherein $R^1$ and $R^2$ are H is obtained, which is a fully unprotected intermediate useful for the synthesis of azaepothilones such as ixabepilone.

The linear amino acids V are then cyclised by macrolactamization reactions to provide macrolactams VI using methods known in the art. A macrolactamization reaction is the formation of a large cyclic amide from a linear amino acid or an amino acid derivative such as an amino ester. Deprotection of the protecting groups $R^1$ and $R^2$ of macrolactams VI then provides azaepothilones I. In the embodiment where $R^1$ and $R^2$ are H in IX, macrolactamization of IX directly provides azaepothilones I. Optionally, macrolactams I are then converted into the epoxide containing azaepothilones by epoxidation using known methods.

In some embodiments, $R^1$ and $R^2$ are TBS, $R^4$ and $R^{4'}$ are BOC, $R^3$ and $R^{3'}$ are H, and Z is sultam ST or sultam ST', or SEM. In some embodiments, $R^A$ is 2-methyl-thiazol-4-yl, $R^B$ and $R^C$ are methyl. Thus, in these embodiments of the invention, the acyclic precursor IV is a compound of formula IVax or IVax', acyclic precursor XXVI is a compound of formula XXVIax or XXVIbx or XXVIbx', acyclic precursor V is a compound of formula Vax, macrolactam VI is a compound of formula VIax, macrolactam I is a compound of formula Ia and the epoxide containing azaepothilone VII is ixabepilone (Scheme 16 and 15). In other embodiments, the acyclic precursor IV is a compound of formula XXVIIax or XXVIIax' (Scheme 18), and the fully unprotected acyclic precursor IX is a compound of formula IXa (Scheme 17).

Preferably, when $R^4$ is BOC and when the Z group is sultam ST or sultam ST', the Z group of intermediate XXVI is converted to OH prior to deprotection of $R^4$ ($R^{4'}$).

The sultam-containing compounds IVax or IVax' provided herein can be converted to Vax via two different routes. In the preferred route, the sultam group of compounds IVax or IVax' is removed by hydrolysis to provide XXVIax using a mixture of a hydroxide and an organic solvents or mixtures of solvents. Preferably hydrogen peroxide ($H_2O_2$) is added to the mixture. The $H_2O_2$ can be aqueous $H_2O_2$. Hydroxides include alkali metal hydroxides such as, but not limited to, LiOH, NaOH, KOH, CsOH, alkaline earth metal hydroxides such as, but not limited to, $Mg(OH)_2$, $Ba(OH)_2$, and ammonium hydroxides such as, but not limited to, tetrabutylammonium hydroxide (TBAH). Organic solvents including, but not limited to, ethers such as 2-Me-THF (2-methyltetrahydrofuran), THF (tetrahydrofuran), dimethoxyethane (DME) and alcohols such as methanol (MeOH), ethanol (EtOH), propanols such as n-propanol (n-PrOH) and isopropanol (i-PrOH), and butanols such as n-butanol (n-BuOH), and mixtures thereof. $H_2O_2$ is preferably an aqueous solution. When using NaOH as the hydroxide, 2-Me-THF or THF and MeOH are preferred solvent mixtures and yields of XXVIax of greater than 70%. When using tetrabutylammonium hydroxide, dimethoxyethane (DME) is preferred as the reaction solvent. Following this reaction step, the BOC protecting group of XXVIax is removed using a Brønsted acid, such as HCl or $H_2SO_4$, or a Lewis acid such as TMSOTf in a solvent such as DCM (dichloromethane). When the Lewis acid TMSOTf is used to effect removal of the BOC protecting group to provide amino acid compound Vax, preferably the reaction is conducted in the presence of 2,6-lutidine (2,6-dimethylpyridine). When TFA is used instead of TMSOTf, both the BOC group and the TBS groups of XXVIax are simultaneously removed to provide the fully unprotected amino acid compound IXa (Scheme 17). Compounds IVax or IVax' can be converted to Vax using an alternative reaction sequence. This alternative reaction sequence comprises the treatment of compound IVax or compound IVax' with a reagent system that can deprotect the BOC protecting group, such as TMSOTf in DCM in the presence of 2,6-lutidine to provide compound XXVIbx or compound XXVIbx', respectively, that can then be converted to amino acid compound Vax upon treatment with a mixture of a hydroxide, $H_2O_2$ and an organic solvent or in a mixture of organic solvents. For example, compound XXVIbx or XXVIbx' can be converted to amino acid compound Vax upon treatment with LiOH or NaOH, aqueous $H_2O_2$ in 2-Me-THF or THF and MeOH or mixtures thereof, or upon treatment with tetrabutylammonium hydroxide (TBAH) and aqueous $H_2O_2$ in DME. This alternative route to amino acid compound Vax (i.e., via compound XXVIbx or XXVIbx') is less preferred than the route proceeding via XXVIax because the lack of protection of the C15 amino group allows some, or greater levels of, N-oxidation to occur. That is, the conversion of compound IVax or IVax' to compound XXVIax and then the conversion of compound XXVIax to amino acid compound Vax is preferred to the corresponding conversion of compound IVax or IVax' to compound XXVIbx or XXVIbx' and then the conversion of compound XXVIbx or XXVIbx' to amino acid compound Vax. Most preferably for the manufacture of ixabepilone using the invention described herein, the intermediate of formula IVax' is converted to the compound of formula XXVIax which is then converted to the compound of formula Vax.

Amino acid Vax of this invention is converted to macrolactam VIax using known conditions for macrolactamization. Conditions that can be used for the macrolactamization include those used for peptide coupling reactions known in the arts, which include the use of phosphonium coupling reagents, such as PyBOP (benzotriazol-1-yloxytri(pyrrolidino)-phosphonium hexafluorophosphate), uronium coupling reagents, such as HATU (O-(7-azabenzotriazol-1-yl)-1,1,3,3-tetramethyluronium hexafluorophosphate), immonium coupling reagents, such as BOMI (benzotriazol-1-yloxy-N,N-dimethyl-methaniminium hexachloroantimonate), carbodiimide coupling reagents, such as DCC (N,N'-dicyclohexylcarbodiimide), imidazolium coupling reagents, such as CDI (1,1'-carbonyldiimidazole) or BOI (2-(benzotriazol-1-yl)oxy-1,3-dimethyl-imidazolidinium hexafluorophosphate), organophosphorous coupling reagents, such as BOP-Cl (N,N'-bis(2-oxo-3-oxazolidinyl)-phosphinic chloride), acid halogenating coupling reagents, such as cyanuric chloride or TFFH (fluoro-N,N,N',N'-tetramethylformamidinium hexafluorophosphate), or others, such as chloroformates, BMPI (2-bromo-1-methylpyridinium iodide) or DMTMM (4-(4,6-dimethoxy[1,3,5]triazin-2-yl)-4-methylmorpholinium chloride) in solvents such as but not limited to THF, in the presence of bases, such as but not limited to DIPEA (N,N-diisopropylethylamine). For example, macrolactamization conditions of the amino acid D4 (see Scheme 5) was reported in *J. Org. Chem.* 2001, 66, 4369-4378.

Deprotection of the TBS protecting group of macrolactam compound VIax using reagents known to cleave silyl ethers to furnish alcohols provides azaepothilone Ia. For example, the treatment of macrolactam compound VIax with TFA in DCM provides azaepothilone Ia. Similarly, direct treatment of fully unprotected amino acid IXa with conditions suitable for effecting macrolactamization provides Ia directly (Scheme 17). Conditions that can be used for the macrolactamization of fully unprotected amino acid IXa to provide azaepothilone Ia include those used for peptide coupling reactions known in the arts, which include the use of peptide coupling agents, such as, but not limited to, HATU, in solvents such as but not limited to THF in the presence of bases, such but not limited to DIPEA. Thus, the synthesis of Ia from IXa saves ones synthetic step as compared to when Vax is used to make Ia (via VIax).

When the epoxide-containing azaepothilone known as ixabepilone is required, epoxidation of azaepothilone Ia using conditions known in the arts for epoxidation of carbon-carbon double bonds is conducted (for example, see *J. Am. Chem. Soc.* 1999, 121, 7050-7062; *J. Org. Chem.* 2001, 66, 4369-4378 and *J. Org. Chem.* 2004, 69, 9269-9284).

In another embodiment, partially protected intermediates XXII or XXII' (Scheme 18) can be used to prepare common intermediate I using similar or the same reaction conditions as used for the conversion of compound IIa or IIa'.

E. Advantages of this Invention:

As compared to the synthesis route for the preparation of ixabepilone disclosed in U.S. Pat. No. 6,867,305 and *J. Org. Chem.* 2001, 66, 4369-4378, the methods described herein do not require the use of azide-containing reagents or intermediates (compare to D1b and D3c in Scheme 5). Azide compounds present challenges to industrial manufacturing due to their inherent toxicity and their potentially explosive nature and therefore it is preferred that the use of such compounds is avoided.

In contrast to the other know routes that can be used for the preparation of ixabepilone, the Suzuki reaction step of II and III to provide the product IV, the methods described herein do not require the presence of triphenylarsine ($AsPh_3$). Triphenylarsine is an organic arsenic compound and arsenic is known to be toxic. Surprisingly, in the embodiments described herein, a rapid and efficient Suzuki reaction occurs without the use of an arsenic-based Suzuki reaction catalyst. This result is particularly advantageous in terms of the safety of the manufacturing staff and to avoid the associated waste management required for arsenic-based toxic chemicals.

Still further, the Suzuki reaction step described herein to couple compound II and compound III to provide product IV proceeds in higher yields than the method described in *J. Org. Chem.* 2001, 66, 4369-4378. For example, when the N—BOC protected amine IIIa' is coupled with IIax', >90% yield can typically be obtained. By contrast, the yield reported in *J. Org. Chem.* 2001, 66, 4369-4378 for the coupling of N—BOC protected amine IIIa' with compound D2a was only 10%.

In contrast to the synthesis route ixabepilone disclosed in *J. Org. Chem.* 2001, 66, 4369-4378, counting from the Suzuki reaction step, three less synthetic steps are required in the methods of the present invention. This is an advantageous on industrial scales because the downstream steps during the manufacturing of pharmaceutical substances are most costly because of the high level of regulation to be applied to ensure that the final active pharmaceutical substance is of high quality fit for human consumption. Therefore it is most cost efficient to minimize the number of downstream synthetic steps from the point at which the high level of regulation is required.

Chiral amine derivative XII is a novel compound that can be prepared with high chiral purity using an aspect of this invention (e.g., the allyl Grignard reagent addition to compound XI). This chiral amine is useful for the synthesis of a whole series of N-protected analogues, III, which have been shown herein to be useful in the synthesis of ixabepilone.

Ixabepilone can be prepared from three building blocks, and in some embodiments these three building blocks can be prepared using known methods, and in other embodiments these can be prepared using methods described herein.

In accordance with the embodiments described above and the Examples provided below, the present invention provides a process for preparing an azaepothilone of formula I

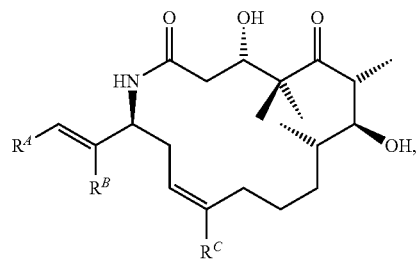

wherein
$R^A$ is selected from substituted or unsubstituted aryl and substituted or unsubstituted heteroaryl;
$R^B$ is selected from H, alkyl and substituted or unsubstituted aryl; and
$R^C$ is selected from H, alkyl, fluoroalkyl, substituted or unsubstituted aryl and substituted or unsubstituted heteroaryl;
the process including:
a) contacting a borane derivative of a compound of formula II

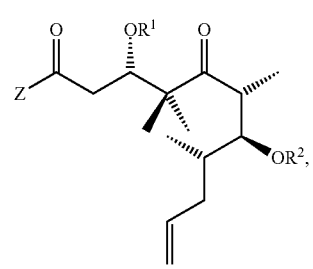

wherein
Z is selected from the group consisting of

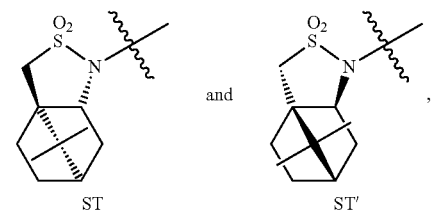

and
$R^1$ and $R^2$ are independently selected from hydrogen, triethylsilyl (TES), triisopropylsilyl (TIPS), tert-butyldimethylsilyl (TBS) and tert-butyldiphenylsilyl (TBDPS),
with a vinyl halide of formula III,

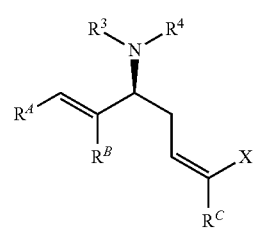

wherein $R^3$ and $R^4$ are independently selected from H, tert-butyloxycarbonyl (BOC), or tert-butylsulfonyl ($SO_2$t-Bu), or together $R^3$ and $R^4$ are $CPh_2$, in the presence of a transition metal catalyst to provide a compound of the formula IV

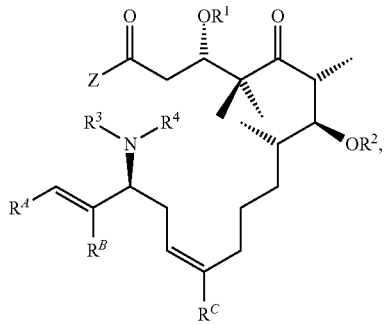

IV b) converting the compound of formula IV to a compound of formula V

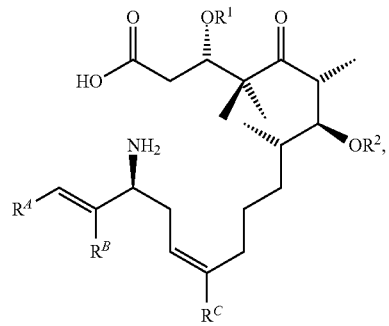

V by converting Z to OH and converting $R^3$ and $R^4$ to H when one or both of $R^3$ and $R^4$ are other than H;

c) cyclizing the compound of formula V to provide a compound of formula VI

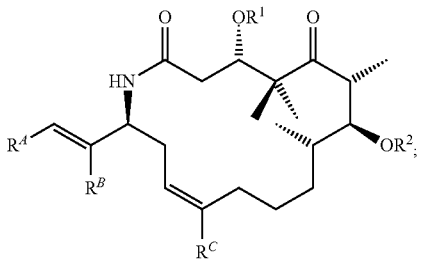

VI and d) deprotecting the compound of formula VI to provide the azaepothilone of formula I.

In some embodiments, the invention provides a process for preparing an epoxide-containing azaepothilone of formula VII

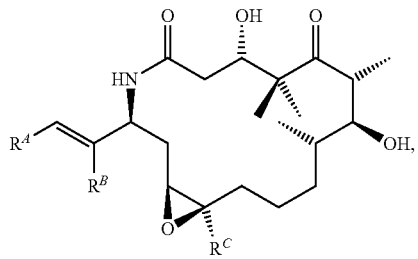

VII wherein
$R^A$ is selected from substituted or unsubstituted aryl and substituted or unsubstituted heteroaryl;
$R^B$ is selected from H, alkyl, and substituted or unsubstituted aryl; and
$R^C$ is selected from H, alkyl, substituted or unsubstituted aryl, substituted or unsubstituted heteroaryl, and fluoroalkyl;

the process including:

a) treating a compound of formula VI

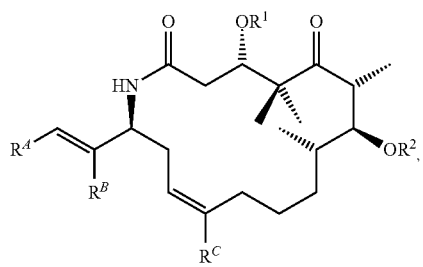

VI wherein $R^1$ and $R^2$ are independently selected from hydrogen, silylalkyl, TES, TIPS, TBS and TBDPS, with an epoxidizing agent to form a compound of formula VIII

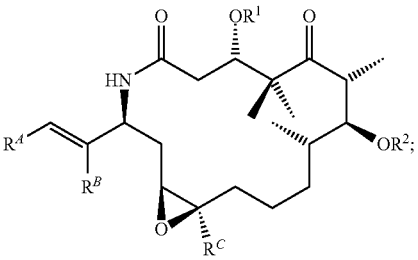

VIII and b) deprotecting the compound of formula VIII to provide the epoxide containing azaepothilone VII.

In some embodiments, the compound of formula VI is prepared according to a method including:

a) contacting a borane derivative of a compound of formula II

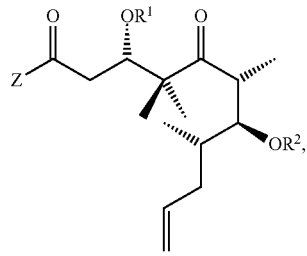

wherein

Z is selected from the group consisting of

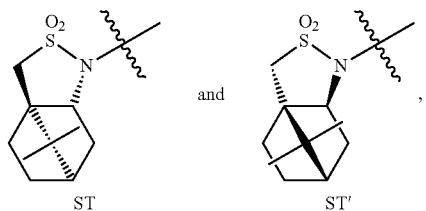

and $R^1$ and $R^2$ are independently selected from hydrogen, triethylsilyl (TES), triisopropylsilyl (TIPS), tert-butyldimethylsilyl (TBS) and tert-butyldiphenylsilyl (TBDPS), with a vinyl halide of formula III

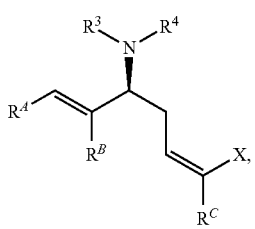

wherein $R^3$ and $R^4$ are independently selected from H, tert-butyloxycarbonyl (BOC), and tert-butylsulfonyl ($SO_2$t-Bu), or together $R^3$ and $R^4$ are $CPh_2$, in the presence of a transition metal catalyst to provide a compound of the formula IV

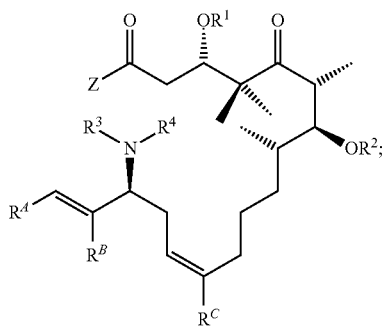

and b) converting the compound of formula IV to a compound of formula V

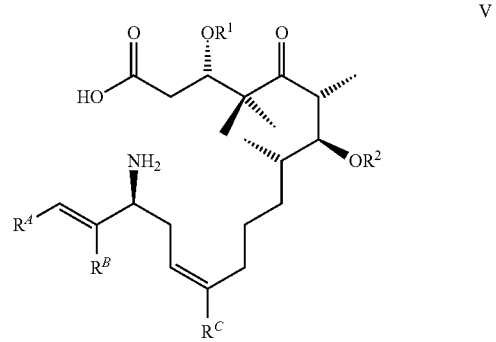

by converting Z to OH and converting $R^3$ and $R^4$ to H when one or both of $R^3$ and $R^4$ are other than H, wherein the converting steps are conducted in any order; and c) cyclizing the compound of formula V to the compound of formula VI.

In some embodiments, the invention provides a process for the preparation of a compound of formula I

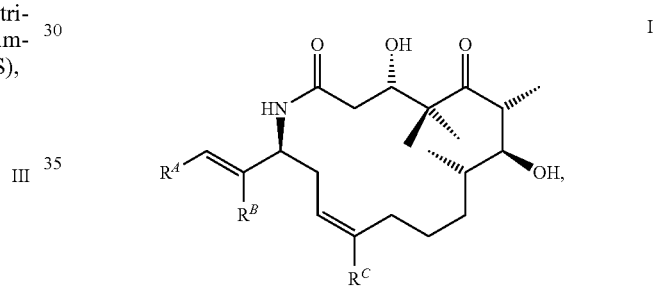

wherein $R^A$ is selected from substituted or unsubstituted aryl and substituted or unsubstituted heteroaryl, $R^B$ is selected from H, alkyl and substituted or unsubstituted aryl, $R^C$ is selected from H, alkyl, fluoroalkyl, substituted or unsubstituted aryl and substituted or unsubstituted heteroaryl (including thiazole, isooxazole), the process including:

a) contacting a borane derivative of a compound of formula II

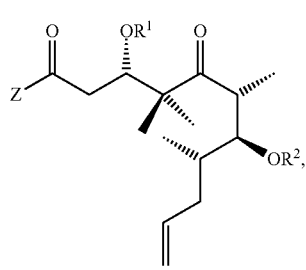

wherein
Z is selected from the group consisting of

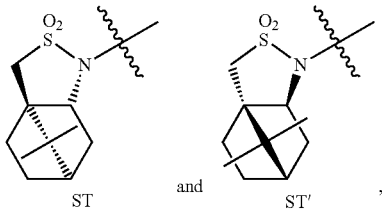

ST and ST', and
R$^1$ and R$^2$ are independently selected from hydrogen, triethylsilyl (TES), triisopropylsilyl (TIPS), tert-butyldimethylsilyl (TBS) and tert-butyldiphenylsilyl (TBDPS),
with a vinyl halide of formula III,

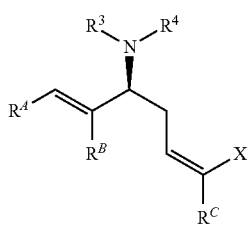

III wherein R$^3$ and R$^4$ are independently selected from H, tert-butyloxycarbonyl (BOC), or tert-butylsulfonyl (SO$_2$t-Bu), or together R$^3$ and R$^4$ are CPh$_2$,
in the presence of a transition metal catalyst to provide a compound of the formula IV

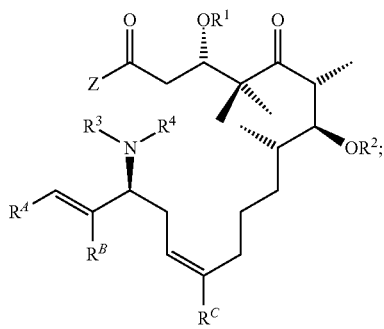

IV b) converting the compound of formula IV to a compound of formula IX

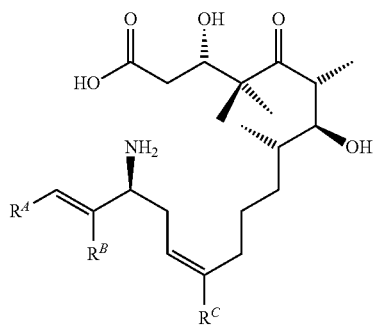

IX by converting Z to OH and converting R$^1$, R$^2$, R$^3$ and R$^4$ to H when any or all of R$^1$, R$^2$, R$^3$ and R$^4$ are other than H, wherein the converting steps are conducted in any order; and c) cyclizing the compound of formula IX to provide the compound of formula I.

In some embodiments, the borane derivative is prepared from the compound of formula II by reaction with a borane selected from the group consisting of 9-borabicyclo-[3.3.1]nonane (9-BBN), 9-borabicyclo[3.3.1]nonane dimer (9-BBN dimer), disiamylborane, and dicyclohexylborane. In some embodiments, the borane is selected from 9-borabicyclo-[3.3.1]nonane (9-BBN) and 9-borabicyclo[3.3.1]nonane dimer (9-BBN dimer).

In some embodiments of the invention, the transition metal catalyst includes a metal selected from Ni and Pd.

In some embodiments, Z is converted to OH by treatment of the compound of formula IV with a mixture including aqueous H$_2$O$_2$, a hydroxide, and a solvent. In some embodiments, the hydroxide is selected from the group consisting of sodium hydroxide and lithium hydroxide and the solvent comprises a mixture of 2-methyltetrahydrofuran or tetrahydrofuran and methanol.

In some embodiments, the processes further includes converting the compound of formula I to an epoxide-containing azaepothilone of formula VII

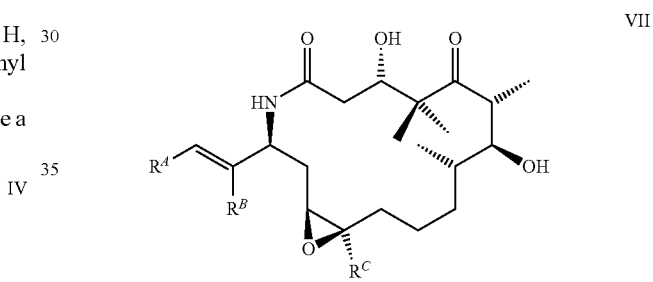

VII by epoxidising the compound of formula I.

In some embodiments, R$^A$ is a 2-methyl-thiazol-4-yl group

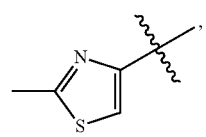

and
R$^B$ and R$^C$ are methyl.

In some embodiments, the invention provides a process for preparing a compound of formula III'

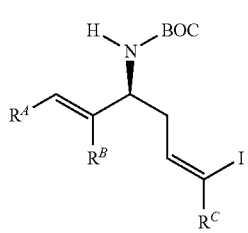

III' wherein R^A is aryl or heteroaryl, and R^B and R^C is selected from the group consisting of H, alkyl, fluoroalkyl, an unsubstituted or substituted aryl group, and an unsubstituted or substituted heteroaryl group,
the process including:
a) contacting a compound of formula X

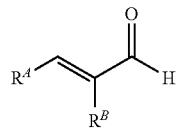
X in an organic solvent with tert-butanesulfinamide in the presence of an activating agent to provide a compound of formula XI

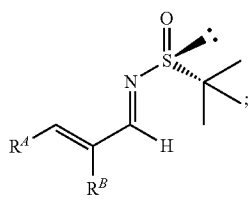
XI b) contacting the compound for formula XI in an organic solvent with an allylating reagent AL

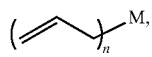

wherein the value n is between 1 to 4, to provide a compound of formula XII

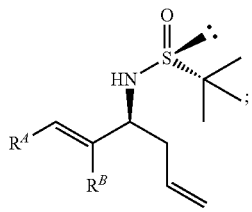
XII c) converting the compound of formula XII in an organic solvent to a compound of formula XIII by treatment with an acid

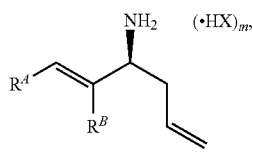
XIII wherein X is a halogen and subscript m is 0, 1 or 2;
d) protecting the compound of formula XIII by its reaction with di-tert-butyl dicarbonate in an organic solvent to give a compound of formula XIVa

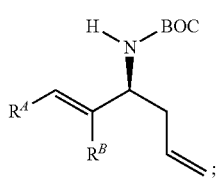
XIVa and
e) converting the compound of formula XIVa to the compound of formula III'.

In some embodiments, the organic solvent of step a) is toluene and the activating reagent is $KHSO_4$.

In some embodiments, M is selected from Mg, Zn, and In.
In some embodiments, step b) provides a mixture of the compound of formula XII and a diastereomer of the formula

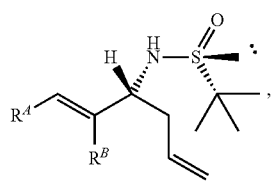

in a diastereomeric ratio of greater than about 10:1.

In some embodiments, the allylating reagent of step b) is allyl magnesium bromide and the organic solvent is a mixture of 2-methyltetrahydrofuran and dichloromethane.

In some embodiments, the compound of formula IIIa is further converted to a compound of formula IIIb

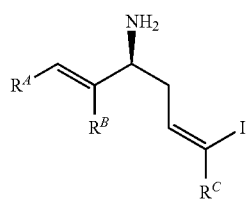
IIIb by a deprotection step.

In some embodiments, the compound of formula IIIb is further converted to a compound of formula IIIc

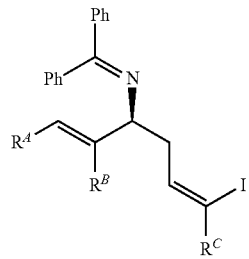
IIIc by protection with a member selected from benzophenone, a benzophenone imine, and a benzophenone dialkyl acetal.

In some embodiments, IIIa is further converted to a compound of formula IIId

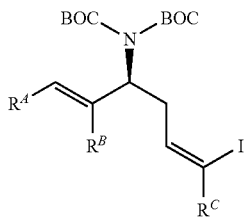
IIId by protection with di-tert-butyl dicarbonate.

In some embodiments, the invention provides a process for the preparation of IIIe

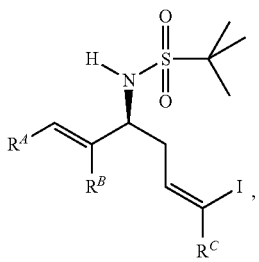
IIIe wherein $R^A$ is selected from aryl and heteroaryl, and $R^B$ and $R^C$ is selected from H, alkyl and aryl, the method including:

a) oxidizing the compound of formula XII

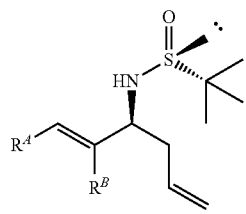
XII to provide a compound of formula XVb

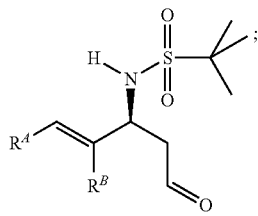
XVb and b) converting the compound of formula XVb into the compound of formula IIIe.

In some embodiments, the compound of formula XII is prepared by a process including:

a) converting a compound of formula X

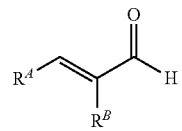
X to a compound of formula XI

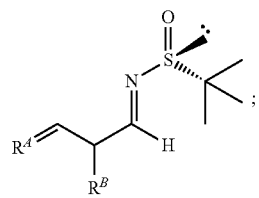
XI and b) adding an allylating reagent of formula AL

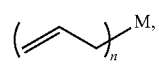

AL wherein n is a value between 1 and 4, to the compound of formula XI to provide the compound of formula XII.

In some embodiments, $R^A$ is a 2-methyl-thiazol-4-yl group

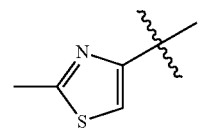 [SMILES: *c1csc(C)n1]

and $R^B$ is methyl.

In some embodiments, the invention provides a process for the preparation of a compound of formula II

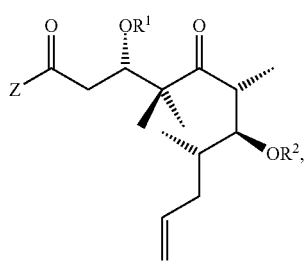
II wherein Z is sultam ST'

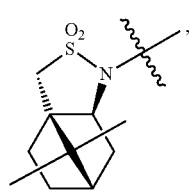

and

R¹ and R² are independently selected from hydrogen, triethylsilyl (TES), triisopropylsilyl (TIPS), tert-butyldimethylsilyl (TBS) and tert-butyldiphenylsilyl (TBDPS);

the process including:

a) activating a compound of formula XVI'

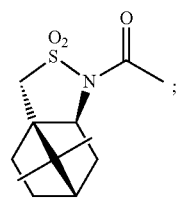

b) treating the activated compound of formula XVI' with a compound of formula XVII

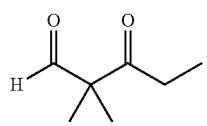

in the presence of a Lewis acid to provide a compound of formula XVIII'

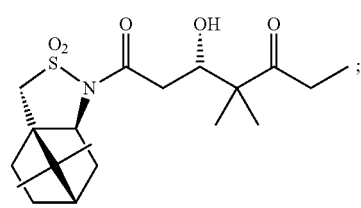

c) optionally protecting the hydroxyl group of the compound of formula XVIII' with a protecting group selected from triethylsilyl (TES), triisopropylsilyl (TIPS), tert-butyldimethylsilyl (TBS) and tert-butyldiphenylsilyl (TBDPS) to provide a compound of formula XIX'

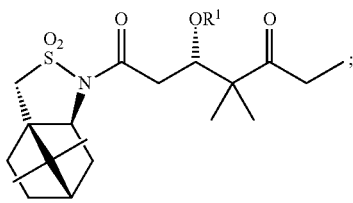

and d) activating the compound of formula XVIII' or the compound of formula XIX' and then reacting the activated compound with a compound of formula XX

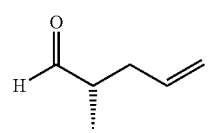

to provide the compound of formula II wherein R² is H;

e) optionally protecting the hydroxyl group of the compound of formula II with a protecting group selected from the group consisting of triethylsilyl (TES), triisopropylsilyl (TIPS), tert-butyldimethylsilyl (TBS) and tert-butyldiphenylsilyl (TBDPS) to provide a compound of formula II wherein R¹ and R² are both hydroxy protecting groups independently selected from the group consisting of triethylsilyl (TES), triisopropylsilyl (TIPS), tert-butyldimethylsilyl (TBS) and tert-butyldiphenylsilyl (TBDPS).

In some embodiments, activating the compound of formula XVI' in step a) includes contacting the compound of formula XVI' with a silyl triflate reagent and a base. In some embodiments, wherein the silyl triflate reagent is tert-butyldimethylsilyl triflate (TBSOTf) and the base is triethylamine.

In some embodiments, the Lewis acid of step b) is a metal halide. In some embodiments, the metal halide is titanium tetrachloride (TiCl₄).

In some embodiments, the activating step of step d) is conducted by treating the compound of formula XVIII' or the compound of formula XIX' with a Lewis acid in the presence of an amine base at a low temperature. In some embodiments, the amine base is N,N-diisopropylethylamine and the low temperature is equal to or colder than −50° C.

In some embodiments, R¹ and R² are both tert-butyldimethylsilyl (TBS).

In some embodiments, the epoxide-containing aza-epothilone VII is ixabepilone

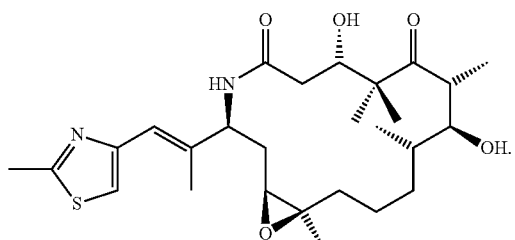

IV. Examples

The following examples are provided to further illustrate, but not to limit this invention.

The symbols, conventions and abbreviations used in the above specification and in the following examples are consistent with those used in the contemporary scientific literature, for example, *Journal of the American Chemical Society* and *The ACS Style Guide: effective communication of scientific information*, 3rd ed.; Coghill, A. M. and Garson, L. R. ed.; Washington, D.C., Oxford University Press, New York Oxford, 2006.

Abbreviations: atm—atmosphere; AcOH—acetic acid; aq.—aqueous; brine—saturated aqueous sodium chloride solution; Bu—butyl; BuOH—butanol; t-Bu—tert-butyl; n-BuLi—n-butyllithium; 9-BBN—9-borabicyclo[3.3.1]nonane; 9-BBN-dimer—9-borabicyclo[3.3.1]nonane dimer; BOC—tert-butyloxycarbonyl; (BOC)$_2$O—di-tert-butyl dicarbonate (BOC anhydride); B.P.—boiling point; d.e.—diastereomeric excess; d.r.—diastereomeric ratio; DIPEA—N,N-diisopropylethylamine (Hünig's base); DMDO—dimethyldioxirane; DMSO—dimethylsulfoxide; DCM—dichloromethane; DCE—dichloroethane; DIBAL—diisobutylaluminium hydride; DMAP—4-dimethylaminopyridine; DME—dimethoxyethane; DMF—N,N-dimethylformamide; dppf—diphenylphosphinoferrocene; e.e.—enantiomeric excess; Et—ethyl; Et$_2$O—diethyl ether; EtOAc—ethyl acetate; g—gram(s); h—hour(s); HATU—(O-(7-azabenzotriazol-1-yl)-N,N,N',N'-tetramethyluronium hexafluorophosphate; HMDS—hexamethyldisilazane; HPLC—High performance liquid chromatography; mg—milligram(s); L—liter(s); LiHMDS—lithium bis(trimethylsilyl)amide; lutidine/2,6-lutidine—2,6-dimethylpyridine; mCPBA—meta-chloroperoxybenzoic acid; mL—milliliter(s); M—molarity; MeOH—methanol; mol—mole(s); mmol—millimole(s); min—minute(s); Me—methyl; M.P.—melting point; MS—mass spectrometry (LCMS is liquid chromatography mass spectrometry); MTBE—methyl tert-butyl ether; N—normality; NaHMDS—sodium bis(trimethylsilyl)amide; NMP—N-methylpyrrolidinone; NMR—nuclear magnetic resonance (spectroscopy); NMO—N-methylmorpholine-N-oxide; MHz—megahertz; Pr—propyl; Ph—phenyl (C$_6$H$_5$); i-PrOH—isopropanol; n-PrOH—n-propanol; PhMe—toluene; PhCl—chlorobenzene; R$_f$—retention factor; sat.—saturated; SEM—2-(trimethylsilyl)ethoxymethyl; SEMCl—2-(trimethylsilyl)ethoxymethyl chloride; TLC—thin layer chromatography; TBAF—tetra-n-butylammonium fluoride; TBAH—tetra-n-butylammonium hydroxide; TBS—tert-butyldimethylsilyl; TBSCl—tert-butyldimethylsilyl chloride; TBDPS—tert-butyldiphenylsilyl; TBDPSCl—tert-butyldiphenylsilyl chloride; TBSOTf—tert-butyldimethylsilyltriflate; TES—triethylsilyl; TESCl—triethylsilyl chloride; Tf—trifluoromethanesulfonyl; TFA—trifluoroacetic acid; THF—tetrahydrofuran; TIPS—triisopropylsilyl; TIPSCl—triisopropylsilyl chloride; TMSOTf—trimethylsilyl triflate; UV—ultraviolet Example 1

Figure 19:
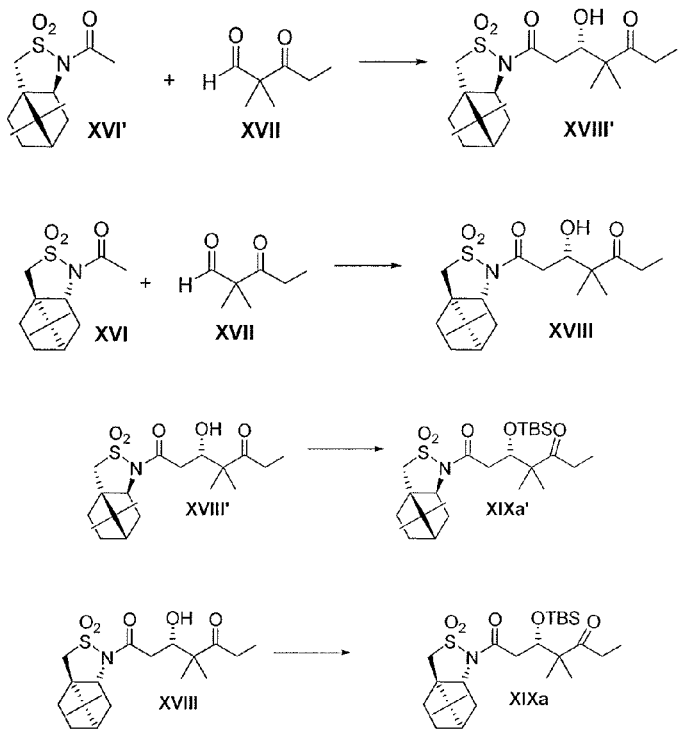
FIG. 19 provides Schemes from Example 1.

Preparation of XIXa and XIXa' (see Schemes in FIG. 19)

Preparation of Compound XVIII'

To a solution of compound XVI' (100 g, 389 mmol) in dry DCM (800 mL) was added Et$_3$N (73 mL, 506 mmol) and TBSOTf (113 g, 428 mmol) dropwise at room temperature under an atmosphere of N$_2$. The resulting reaction mixture was stirred at room temperature overnight (solution A). In a separate flask, to a solution of XVII (80 g, 622 mmol) in dry DCM (500 mL) was added TiCl$_4$ (1 N in DCM, 650 mL, 650 mmol) at −78° C. under an atmosphere of N$_2$. After stirred at −78° C. for 10 minutes, solution A was added dropwise into the XVII solution over 1 hour, then the resulting mixture was warmed to room temperature and stirred overnight. After completion by TLC, the reaction mixture was quenched with sat. aq. NH$_4$Cl. The aqueous layer was extracted with DCM (400 mL×2). The combined organic layers were dried over Na$_2$SO$_4$, filtered and evaporated. The residue was diluted with hexane (500 mL) and stirred overnight for precipitation. The solid was filtered and washed with hexane to give 109 g of XVIII' (d.r. >20:1, R$_f$=0.3, EtOAc/petroleum ether=1:5, KMnO$_4$) as white solid in 73% yield. M.P.=100-102° C.; $^1$H NMR (400 MHz, CDCl$_3$) δ 4.31 (brs, 1H), 3.878 (t, J=6 Hz, 1H), 3.475 (q, J=13.6 Hz, 2H), 2.812 (d, J=6 Hz, 2H), 2.594-2.511 (m, 2H), 2.171-2.042 (m, 2H), 1.924-1.877 (m, 3H), 1.433-1.355 (m, 2H), 1.172 (s, 3H), 1.158 (s, 3H), 1.128 (s, 3H), 1.031 (t, J=6.8 Hz, 3H), 0.968 (s, 3H); $^{13}$C NMR (100 MHz, CDCl$_3$) δ 215.7, 171.3, 73.1, 65.3, 53.0, 51.2, 48.6, 47.9, 44.7, 38.4, 37.8, 39.2, 31.6, 26.5, 21.8, 20.9, 20.0, 19.2, 8.0.

Preparation of Compound XVIII'

Under N$_2$ atmosphere, to a solution of XVI' (200 g, 777 mmol) in dry DCM (800 mL) was added triethylamine (146 mL, 1047 mmol) and TBSOTf (231 g, 874 mmol) dropwise at 22° C. The mixture was stirred at room temperature for 3 hours and was added dropwise over 2 hours to a solution of XVII (160 g, 1248 mmol) and TiCl$_4$ (1 M in DCM, 1300 mL, 1300 mmol) in dry DCM (1000 mL) at −70 to −78° C. The resulting mixture was slowly warmed to 22° C. in a rate of 15° C. per hour. The reaction mixture was stirred at 22° C. for another hour and was quenched by adding sat. aq. NH$_4$Cl (1000 mL) and H$_2$O (800 mL). After layer separation, the organic layer was washed with H$_2$O (1000 mL×3), dried over Na$_2$SO$_4$ for 4 hours, filtered, concentrated at 40-65° C. and co-evaporated with n-heptane (600 mL×2). The desired product was then precipitated by stirring in n-heptane (1000 mL) overnight, filtered and washed with n-heptane (400 mL×2) to give XVIII' as an oily solid (262 g, yield: 87%, 92.5% HPLC purity, d.r.=24.7:1).

Preparation of XVIII

To a solution of compound XVI (21.45 g, 83.33 mmol) in dry DCM (215 mL) was added Bu$_2$BOTf (100 mL, 1 M) at 0° C. under an atmosphere of N$_2$, the reaction mixture was stirred for 30 minutes, then DIPEA (17.3 mL, 104.16 mmol) was added, and the reacting mixture was stirred for another 30 minutes. After the resulting mixture was cooled to −78° C., XVII (14.95 g, 116.67 mmol) was added dropwise. The reaction temperature was allowed to warm to room temperature and stirred overnight. The reaction mixture was quenched with sat. aq. NH$_4$Cl, then extracted with EtOAc. The combined organic layer were dried over Na$_2$SO$_4$, filtered and evaporated. The residue was purified by column, eluting with petroleum ether/EtOAc=20:1 to 5:1) to give XVIII (23 g, yield: 71.9%) as a white solid. $^1$H NMR (400 MHz, CDCl$_3$) δ 4.30 (m, 1H), 3.87(m, 1H), 3.45 (m, 2H), 3.25 (m, 1H), 2.80 (m, 2H), 2.55 (m, 2H), 2.08 (m, 2H), 1.89 (m, 3H), 1.37 (m, 2H), 1.17 (s, 3H), 1.15 (s, 3H), 1.12 (s, 3H), 1.02(t, J=7.2 Hz, 3H), 0.97 (s, 3H); $^{13}$C NMR (100 MHz, CDCl$_3$) δ 216.1, 171.5, 73.0, 65.4, 53.1, 51.2, 48.7, 48.0, 44.9, 38.6, 38.0, 33.1, 31.4, 26.6, 21.8, 21.06, 20.1, 19.4, 8.1.

Preparation of Compound XIXa'

To a solution of XVIII' (69 g, 179 mmol) in dry DCM (600 mL) at −45° C. was added 2,6-lutidine (57.6 g, 537 mmol) and TBSOTf (104 g, 394 mmol) dropwise under an atmosphere of $N_2$. The reaction mixture was stirred at this temperature for 2 hours and continued to stir at room temperature overnight. The reaction mixture was quenched with MeOH (50 mL), washed with sat. aq. citric acid, dried over $Na_2SO_4$, filtered and evaporated. The residue was diluted with petroleum ether (100 mL, B.P.=60-90° C.) and stirred overnight. The precipitation were filtrated and washed with petroleum ether (30 mL×3) to give XIXa' ($R_f$=0.6, EtOAc/petroleum ether=1:5, $KMnO_4$) (62.6 g, yield: 70%) as a white solid. M.P.=91-93° C.; $^1H$ NMR(400 MHz, $CDCl_3$) δ 4.729 (t, J=4.8 Hz, 1H), 3.84 (dd, J=7.6 Hz, 2.8 Hz, 1H), 3.446 (q, J=14 Hz, 2H), 2.811 (d, J=4.4 Hz, 2H), 2.568-2.459 (m, 2H), 2.191-2.145 (m, 1H), 2.086-2.032 (m, 1H), 1.905-1.865 (m, 3H), 1.394-1.343 (m, 2H), 1.161 (s, 3H), 1.065 (s, 3H), 0.991 (t, J=6.8 Hz, 3H), 0.963 (s, 3H), 0.824 (s, 9H), 0.065 (s, 3H), 0.013 (s, 3H); $^{13}C$ NMR (100 MHz, $CDCl_3$) δ 214.9, 170.1, 71.8, 65.6, 53.0, 52.7, 48.5, 47.8, 44.8, 40.5, 38.6, 33.1, 31.5, 26.6, 26.0, 20.9, 20.8, 20.6, 20.0, 18.2, 7.8, −4.1, −5.0.

Preparation of Compound XIXa'

Under $N_2$ atmosphere, to a solution of XVIII' (282 g, 731 mmol, 93% HPLC purity) in dry DCM (2260 mL) was added 2,6-lutidine (219 g, 2.04 mol) and TBSOTf (396 g, 1.50 mol) dropwise at −45 to −50° C. The reaction mixture was stirred at −45 to −50° C. for 2 hours and at 22° C. for another hour. After the reaction was complete, as judged by HPLC, the reaction was quenched by adding MeOH (225 mL) and the mixture was washed with sat. aq. citric acid (1410 mL×2), dried over $Na_2SO_4$ (423 g) for 4 hours and concentrated. The desired product was precipitated by stirring in n-heptane (846 mL) for 4 hours, filtered, washed with n-heptane (564 mL×2) to give XIXa' as a white solid (235 g, yield: 64%, 98.1% HPLC purity).

Preparation of XIXa

To a solution of XVIII (23 g, 59.66 mmol) in dry DCM (160 mL) at −45° C., was added 2,6-lutidine (10.4 mL, 89.49 mmol) and TBSOTf (16.8 mL, 71.59 mmol) dropwise under an atmosphere of $N_2$. The reaction mixture was stirred at this temperature for 2 hours and continued to stir at room temperature overnight. The reaction mixture was quenched by MeOH and evaporated. The residue was re-dissolved in EtOAc, washed twice with critic acid solution, dried over $Na_2SO_4$, filtered and evaporated. The residue was purified by column chromatograph on silica gel (eluents: petroleum ether/EtOAc=10:1) to give XIXa as a white solid (19.2 g, yield: 64.4%). $^1H$ NMR (400 MHz, $CDCl_3$) δ 4.65 (m, 1H), 3.83 (m, 1H), 3.45 (m, 2H), 2.93 (m, 1H), 2.65 (m, 1H), 2.50 (m, 2H), 2.10 (m, 2H), 1.86 (m, 3H), 1.36 (m, 2H), 1.14 (s, 3H), 1.13 (s, 3H), 1.05 (s, 3H), 0.95 (m, 6H), 0.83 (s, 9H), 0.06 (s, 3H), 0.04 (s, 3H).

Example 2

Figure 20:
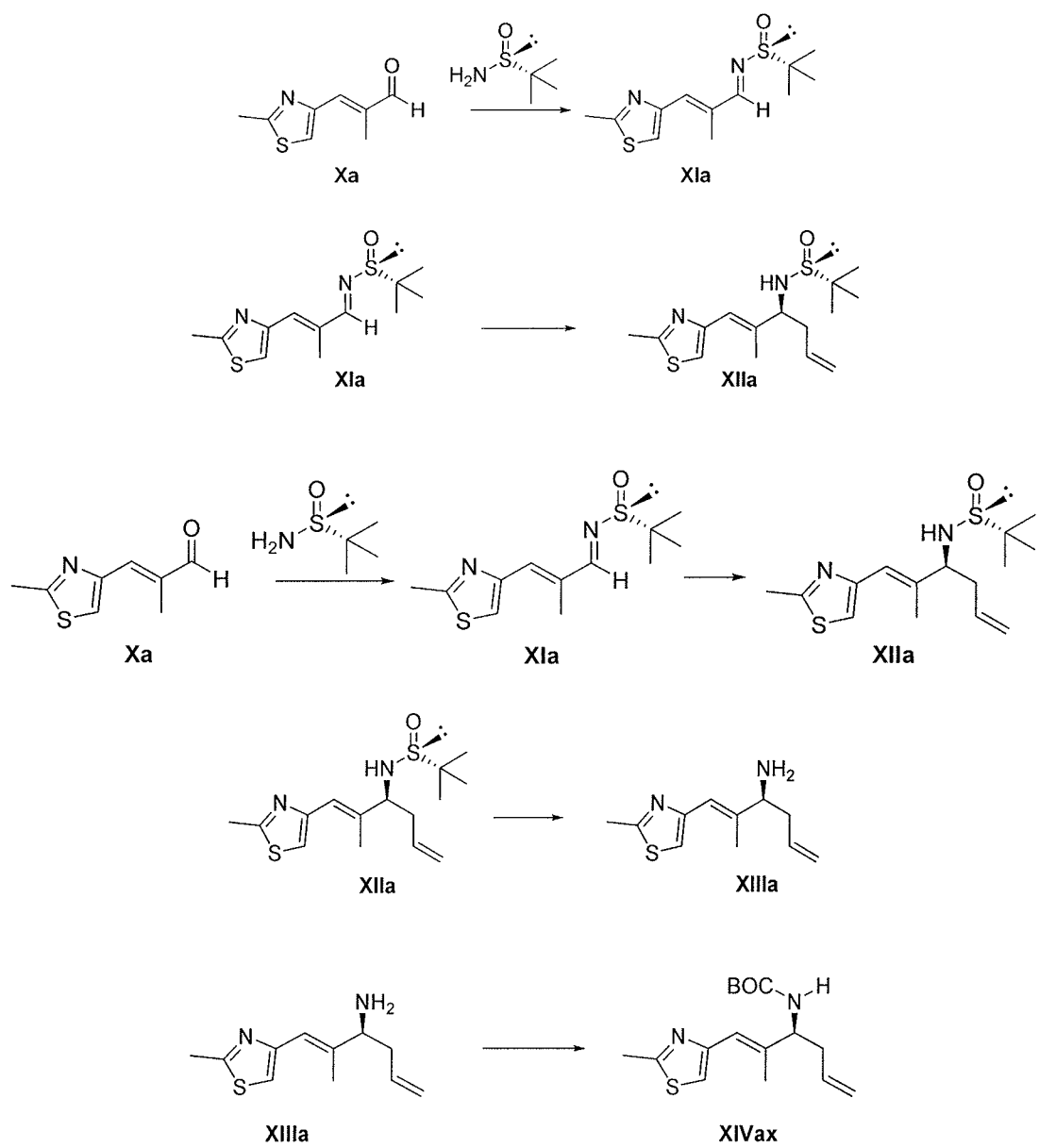
FIG. 20 provides Schemes from Example 2.

Preparation of XIVax (see Schemes in FIG. 20)

Preparation of Xia

To a solution of Xa (35 g, 200 mmol, $R_f$=0.5, EtOAc/petroleum ether=1:3, UV) in dry THF (414 mL) was added (R)-tert-butyl-sulfinamide (29 g, 400 mmol) and Ti(i-PrO)$_4$ (118 mL, 400 mmol) at room temperature under an atmosphere of $N_2$, then the reaction mixture was stirred overnight. The mixture was cooled to 5° C. with ice bath and brine (150 mL) was added cautiously. The resulting suspension was diluted with EtOAc (100 mL) and filtered through a pad of diatomaceous earth and the filter cake was washed with EtOAc (150 mL×2). The filtrate was washed with brine (260 mL×3), dried over $Na_2SO_4$, filtered and concentrated under reduced pressure. The residue was purified by column chromatography on silica gel (EtOAc/petroleum ether=1:5) to give XIa (42 g, yield: 77%, $R_f$=0.4, EtOAc/petroleum ether=1:3, UV) as a yellow solid. $^1H$ NMR (400 MHz, $CDCl_3$) δ 8.25 (s, 1H), 7.31 (s, 1H), 7.04 (s, 1H), 2.74 (s, 3H), 2.37 (s, 3H), 1.22 (s, 9H); $^{13}C$ NMR (100 MHz, $CDCl_3$) δ 166.8, 165.6, 152.1, 135.6, 121.4, 57.5, 22.5, 19.4, 13.3.

Preparation of XIIa

Under an atmosphere of $N_2$, to a solution of XIa (30 g, 111 mmol, $R_f$=0.7, EtOAc/petroleum ether=1:1, UV) in dry DCM (750 mL) was added allylmagnesium bromide (185 mL, 555 mmol, 3N in $Et_2O$) at −50° C. After addition, the reaction mixture was stirred at this temperature for another 1.5 h. Sat. aq. $NH_4Cl$ (580 mL) was added to quench the reaction at −50° C. and the mixture was warmed to room temperature. The organic layer was separated and the aqueous was extracted with DCM (300 mL×3). The combined organic phase was washed with brine (500 mL×3), dried over $Na_2SO_4$, filtered and concentrated under reduced pressure. The crude was analysed by HPLC showing a d.e. of 98.0%. The crude was purified by column chromatography on silica gel (EtOAc/petroleum ether=1:1) to give XIIa as a yellow oil (29 g, yield: 83.8%, HPLC showing a d.e. of 99.4%). $^1H$ NMR (400 MHz, $CDCl_3$) δ 6.85 (s, 1H), 6.45 (s, 1H), 5.70-5.60 (m, 1H), 5.08-5.02 (m, 2H), 3.87 (t, J=6.4 Hz, 1H), 3.35 (s, 1H), 2.58 (s, 3H), 2.40-2.22 (m, 2H), 1.92 (s, 3H), 1.10 (s, 9H); $^{13}C$ NMR (100 MHz, $CDCl_3$) δ 164.5, 152.4, 139.3, 134.0, 121.5, 117.7, 116.2, 62.8, 56.0, 38.0, 22.6, 19.2, 14.9.

Under an atmosphere of $N_2$, to a suspension of indium powder (170 mg, 1.48 mmol) and XIa (100 mg, 0.37 mmol) in sat. NaBr (3.7 mL) was added allyl bromide (0.13 mL, 1.48 mmol) at room temperature. Then the reaction mixture was stirred for 20 h at room temperature. The mixture was then quenched by addition of brine (7.4 mL) and EtOAc (7.4 mL), filtered through a pad of silica gel and eluted with EtOAc. The organic phase was separated and the aqueous layer was extracted with EtOAc. The combined organic phase was dried over $MgSO_4$, filtered and concentrated under reduced pressure. The crude was determined by HPLC (conversion: 44%, d.e.=100%).

Under an atmosphere of $N_2$, to a suspension of activated zinc powder (72 mg, 1.1 mmol) and XIa (100 mg, 0.37 mmol) in dry THF (7.0 mL) was added allyl bromide (0.10 mL, 1.1 mmol) at room temperature. Then the reaction mixture was stirred for 1 h at room temperature. The mixture was then quenched by addition of sat. aq. $NH_4Cl$ (8.0 mL) and EtOAc (8.0 mL). The organic layer was collected and the aqueous layer was extracted with EtOAc. The combined organic phase was dried over $MgSO_4$, filtered and concentrated under reduced pressure. The crude was determined by HPLC (conversion: 100%, d.e.=71.9%).

Under an atmosphere of $N_2$, to a suspension of activated zinc powder (78 mg, 1.2 mmol), In(OTf)$_3$ (340 mg, 0.6 mmol) and XIa (110 mg, 0.4 mmol) in dry THF (7.6 mL) was added allyl bromide (0.10 mL, 1.2 mmol) at room temperature. Then the reaction mixture was stirred for 2 h at room temperature.

The mixture was then quenched by addition of sat. aq. NH$_4$Cl (8.0 mL) and EtOAc (8.0 mL). The organic layer was collected and the aqueous layer was extracted with EtOAc. The combined organic phase was dried over MgSO$_4$, filtered and concentrated under reduced pressure. The crude was determined by HPLC (conversion: >97%, d.e.=93.8%).

Under an atmosphere of N$_2$, to a suspension of activated zinc powder (75 mg, 1.16 mmol), InCl$_3$ (128 mg, 0.58 mmol) and XIa (104 mg, 0.38 mmol) in THF (7.7 mL) was added allyl bromide (0.10 mL, 1.2 mmol) at room temperature. Then the reaction mixture was stirred for 12 h at room temperature. The mixture was then quenched by addition of sat. aq. NH$_4$Cl (8.0 mL) and EtOAc (8.0 mL), the organic layers was collected and the aqueous layer was extracted with EtOAc. The combined organic phase was dried over MgSO$_4$, filtered and concentrated under reduced pressure. The crude was detected by HPLC (conversion: 83.6%, d.e.=70.2%).

Under an atmosphere of N$_2$, a suspension of activated zinc powder (150 mg, 2.32 mmol) and allyl bromide (0.20 mL, 2.4 mmol) in dry THF (7.8 mL) was stirred for 1.5 h at room temperature, then the mixture was cooled to −78° C. and XIa (104 mg, 0.38 mmol) in dry THF (1 mL) was added. The reaction mixture was stirred for 6 h at −78° C. The mixture was then quenched by addition of sat. aq. NH$_4$Cl (16.0 mL) and EtOAc (16.0 mL), the organic layer was collected and the aqueous layer was extracted with EtOAc. The combined organic phase was dried over MgSO$_4$, filtered and concentrated under reduced pressure. The crude was purified by column chromatography to give XIIa as a white solid (84 mg, yield: 70%, d.e.=70%).

Preparation of XIIa

To a solution of Xa (100 g, 0.60 mol, 93% HPLC purity) in dry toluene (800 mL, KF<200 ppm) was added (R)-tert-butyl-sulfinamide (94.2 g, 0.78 mol) and KHSO$_4$ (163 g, 1.20 mol) at room temperature under N$_2$ atmosphere. After stirring at 25-35° C. for 2 hours, the reaction mixture was filtered through a pad of silica gel and the filter was washed with toluene (100 mL×3). The combined filtrates were washed with sat. aq. NaHCO$_3$ (500 mL) and H$_2$O (500 mL), and concentrated under vacuum to give XIa (170 g, 93.7% HPLC purity) as a yellow solid, which was used directly for the next step.

Under N$_2$ atmosphere, to a suspension of Mg (100 g, 4.11 mol, 100-200 mesh) in dry 2-Me-THF (1.5 L, KF<200 ppm) was added I$_2$ (2.00 g, 7.88 mmol) at 35-45° C. over 2 hours. After cooling to −25° C., a solution of allyl bromide (484 g, 4.00 mol) in dry 2-Me-THF (0.5 L, KF<200 ppm) was added dropwise slowly while controlling the temperature at −25 to −15° C. (in about 2.5 hours). After stirring for 1 hour, the mixture was slowly warmed to 25° C. and stirred for another 2 hours. The resulting suspension was settled and the desired allylmagnesium bromide reagent was obtained by decanting the upper clear layer from the reactor.

Under N$_2$ atmosphere, to a solution of crude XIa (170 g, from 0.60 mol of Xa) in dry DCM (800 mL) was added dropwise a solution of prepared allylmagnesium bromide in 2-Me-THF (480 mL) at <−40° C. After stirring at <−40° C. for 0.5 hour, sat. aq. NH$_4$Cl (500 mL) was slowly added dropwise into the reaction mixture while maintaining the internal temperature <−20° C. After the resulting mixture was warmed to 10-20° C., the layers were separated. The aqueous layer was extracted by MTBE (400 mL) and the combined organic layers were washed with H$_2$O (800 mL) and concentrated to 200 mL. The solvents were co-evaporated by n-heptane (500 mL×3) to 300 mL. The resulted suspension was slowly cooled to 0° C., stirred for 2 hours and filtered. The solids were washed with n-heptane (170 mL) and dried under vacuum at 40° C. for 16 hours to give XIIa (172 g, yield: 92% from Xa in 2 steps, 93% HPLC purity, >99% d.e.) as an off-white solid.

Preparation of XIIIa

To a solution of XIIa (29 g, 93 mmol, R$_f$=0.6, EtOAc, UV) in dioxane (280 mL) was added aq. HCl in dioxane (150 mL, 4 N) dropwise at 5° C. After addition, the reaction mixture was stirred at room temperature overnight. Then the solvent was evaporated off under reduced pressure and the residue was diluted with water (500 mL). The aqueous was extracted with EtOAc (150 mL×2). The aqueous was basified until the pH=9 using aq. NaOH (1 N) and extracted with EtOAc (150 mL×3). The organic layers were combined, washed with brine (100 mL×3), dried and concentrated under reduced pressure to give XIIIa (14 g, yield: 73%, R$_f$=0.5, MeOH/DCM=1:10, UV) as a brown oil which was used directly without any purification. $^1$H NMR (400 MHz, CDCl$_3$) δ 6.83 (s, 1H), 6.42 (s, 1H), 5.74-5.64 (m, 1H), 5.06-4.98 (m, 2H), 3.42-3.39 (m, 1H), 2.62 (s, 3H), 2.31-2.26 (m, 2H), 1.96 (s, 3H), 1.42 (brs, 2H); $^{13}$C NMR (100 MHz, CDCl$_3$) δ 164.2, 153.0, 143.3, 135.4, 118.5, 115.1, 58.9, 40.2, 29.8, 19.1, 14.8.

Preparation of XIVax

To a solution of compound XIIIa (3 g, 14.4 mmol, R$_f$=0.5, MeOH/DCM=1:10, UV) in THF (30 mL) was added Et$_3$N (3 g, 28.8 mmol) at room temperature, followed by addition of (Boc)$_2$O (3.5 g, 15.8 mmol) in THF (30 mL). The reaction was stirred overnight. After TLC analysis (petroleum ether/EtOAc=5:1) showed the reaction was complete, the mixture was diluted with sat. aq. NH$_4$Cl solution (50 mL) and EtOAc (50 mL). The organic layer was separated and the aqueous layer was extracted with EtOAc (30 mL×3). The combined organic layers were washed with brine (30 mL×3), dried over Na$_2$SO$_4$ and concentrated under vacuum to give the crude product, which was purified by column chromatography on silica gel to give the mono-protected amine XIVax (4 g, yield: 90.0%, R$_f$=0.9, EtOAc/petroleum ether=1:3, UV) as a white solid. $^1$H NMR (400 MHz, CDCl$_3$) δ 6.91 (s, 1 H); 6.44 (s, 1 H), 5.79-5.69 (m, 1 H), 5.14-5.07 (m, 1H), 4.68 (brs, 1 H), 4.22 (brs, 1H), 2.70 (s, 3H), 2.39-2.36 (m, 2H), 2.05 (s, 3H), 1.43 (s, 9 H); $^{13}$C NMR (100 MHz, CDCl$_3$) δ 164.4, 155.2, 152.9, 139.6, 134.1, 118.9, 118.0, 115.5, 76.7, 56.8, 38.1, 33.3, 28.4, 19.2, 16.0.

Example 3

Figure 21:
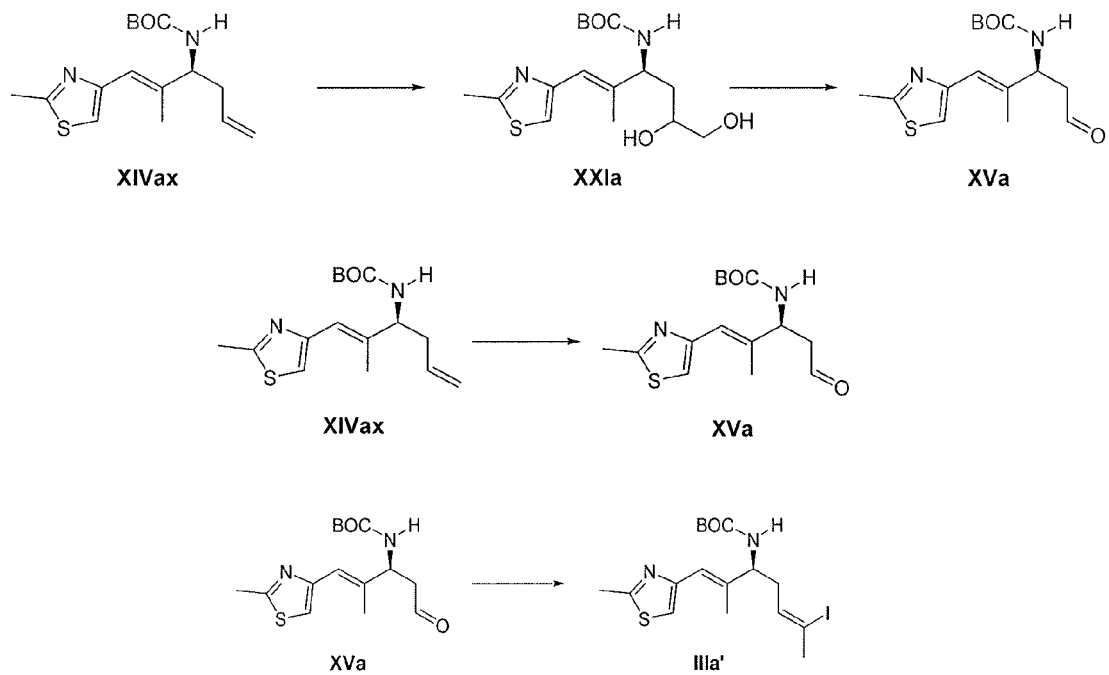
FIG. 21 provides Schemes from Example 3.

Preparation of IIIa' (see Schemes in FIG. 21)

The Preparation of Compound XVa

To a solution of XIVax (10 g, 32.5 mmol, R$_f$=0.9, EtOAc/petroleum ether=1:3, UV) in THF/t-BuOH/H$_2$O (1:1:0.1, 210 mL) was added NMO (9.13 g, 50% aq. solution, 39 mmol) and OsO$_4$ (8.3 mL, 0.65 mmol, 1 g in 50 mL t-BuOH) at 0° C., followed by stirring at 23° C. for 18 h. After TLC analysis (Petroleum/EtOAc=1:1) showed that the reaction was complete, the reaction mixture was quenched by adding sat. aq. NaHSO$_3$ (80 mL) and H$_2$O (200 mL) at 0° C., stirred for 30 min and extracted with MTBE (100 mL×4). The collected organic layers were washed with brine (100 mL×2), dried over Na$_2$SO$_4$ and concentrated under vacuum to give the crude product XXIa (22 g, R$_f$=0.2, EtOAc/petroleum ether=1:3, UV) as a yellow oil.

To a solution of XXIa (22 g, crude from 32.5 mmol of XIVax, $R_f$=0.2, EtOAc/petroleum ether=1:3, UV) in THF/H$_2$O (1:1, 200 mL) was added NaIO$_4$ (16.7 g, 78.0 mmol) at 0° C. and stirred for 40 min. After TLC analysis (Petroleum/EtOAc=1:1) showed that the reaction was complete, the mixture was quenched with H$_2$O (500 mL) and extracted with EtOAc (100 mL×4). The collected organic layers were washed with brine (100 mL×3), dried over Na$_2$SO$_4$, concentrated and purified by column chromatography on a short pad of silica gel (Petroleum/EtOAc=2:1) to give the product XVa (6.72 g, yield: 66.7%, $R_f$=0.8, EtOAc/petroleum ether=1:3, UV) as a yellow oil. $^1$H NMR (400 MHz, CDCl$_3$) δ 9.757 (s, 1H), 6.941 (s, 1H), 6.460 (s, 1H), 4.889 (s, 1H), 4.708 (s, 1H), 2.764-2.725 (m, 2H), 2.694 (s, 3H), 2.087 (s, 3H), 1.428 (s, 9H).

Preparation of XVa

To a stirred solution of XIVax (1.57 g, 5.09 mmol) in acetone (35 mL) and water (25 mL) was added sequentially at 30° C. NMO monohydrate (1.18 g, 8.73 mmol) and K$_2$OsO$_4$.2H$_2$O (33.1 mg, 90 μmol). The resulting mixture was stirred at 30° C. for 3 hours. After the reaction was complete as judged by HPLC, the osmate was deactivated by adding DMAP (275 mg, 2.25 mmol) at 30° C. and the mixture was stirred for another 30 minutes, followed by adding NaIO$_4$ (1.61 g, 7.53 mmol) to proceed the oxidative cleavage. After stirring for 1 hour at 30° C., the resulting suspension was filtered and the filtrate was concentrated under reduced pressure to remove acetone. The residual aqueous solution was extracted with 2-Me-THF (30 mL×2) and the combined organic layers were washed with 10% aq. citric acid (30 mL) and brine (30 mL), dried over Na$_2$SO$_4$ (11.7 g), filtered and concentrated to afford the crude XVa, which was purified by column chromatography on silica gel (eluent EtOAc/n-heptane=40:60) to give the pure XVa (907 mg, yield: 57%, $R_f$=0.22 for EtOAc/n-heptane=40:60) as a light brown solid.

The Preparation of Compound IIIa'

To a suspension of ethyltriphenylphosphonium iodide (18.2 g, 43.4 mmol) in THF (270 mL) was added n-BuLi (17.4 mL, 2.5 M, 43.4 mmol) at 17° C. under N$_2$ to form a red solution. After disappearance of the solid, the mixture was added to a solution of I$_2$ (11 g, 43.4 mmol) in THF (250 mL) dropwise at −75 to −80° C. to form a yellow suspension. The mixture was stirred at −75° C. for 5 min and then warmed up to −20° C. NaHMDS (20.3 mL, 2 M, 40.6 mmol) was added dropwise in 20 min to afford a red solution and the mixture was stirred for 5 min. To this mixture was added a solution of XVa (6.72 g, 21.7 mmol, $R_f$=0.3, EtOAc/petroleum ether=1: 5, UV) in THF (15 mL) dropwise in 20 min and stirred at −20 to 10° C. for 1 h. After TLC analysis (Petroleum:EtOAc=2:1) showed that the reaction was complete, the reaction mixture was filtered through a pad of diatomaceous earth, concentrated and purified by column chromatography on silica gel (Petroleum/EtOAc=5:1) to give a yellow oil of IIIa' (3.7 g, yield: 38%, M.P.=65-67° C., R=0.6, EtOAc/petroleum ether=1:5, UV) as a single isomer. $^1$H NMR (400 MHz, CDCl$_3$) δ 6.93 (s, 1H), 6.46 (s, 1H), 5.44 (t, J=6.4, 1H), 4.69 (d, J=7.2, 1H), 4.3 (m, 1H), 2.70 (s, 3H), 2.50 (s, 3H), 2.35 (m, 2H), 2.06 (s, 3H), 1.43 (s, 9H); $^{13}$C NMR (100 MHz, CDCl$_3$) δ 164.5, 155.2, 152.8, 139.4, 131.3, 119.1, 115.7, 103.7, 79.5, 76.7, 56.8, 41.0, 33.7, 28.4, 19.2, 16.1, 14.2.

Example 4

Figure 22:
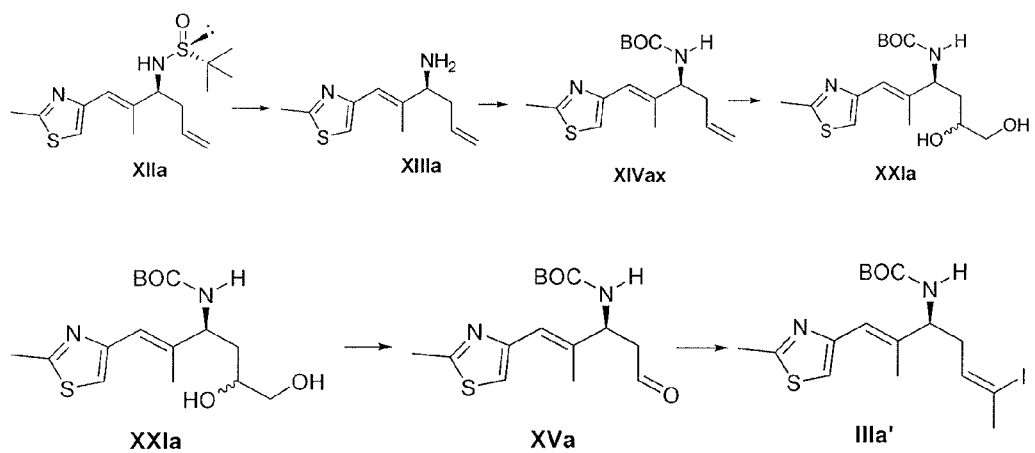
FIG. 22 provides Schemes from Example 4.

Preparation of IIIa' (see Schemes in FIG. 22)

Preparation of XXIa

To cooled MeOH (2.0 L, 0-10° C.) was added 37% wt. aq. HCl (200 mL), while keeping the temperature <30° C. for safety concern, and solid XIIa (276 g, 0.88 mol, 95% HPLC purity). After the reaction was complete as judged by HPLC for 1 hour at 10-30° C., the solvent was evaporated off under reduced pressure. The residue was diluted by water (1.3 L) and MTBE (1.3 L), and the layers were separated. The aqueous layer was collected, added MTBE (1.3 L) and basified to pH=10-11 using 10% aq. NaOH (ca. 550 mL). The organic layer was collected and the aqueous layer was extracted by MTBE (1.3 L). The combined organic layers were washed with brine (1.3 L) and H$_2$O (1.3 L) and concentrated to give XIIIa as an oil (186 g, 94% HPLC purity), which was used directly for the next step.

To a solution of crude XIIIa (186 g, from 0.88 mol of XIIa) in DCM (1.1 L) was added a solution of Boc$_2$O (202 g, 0.93 mmol) in DCM (276 mL) at 0-15° C. After the reaction was complete as judged by HPLC for 1 hour at 0-25° C., the reaction was quenched by adding H$_2$O (15.8 g) and the mixture was stirred at 0-25° C. for another 0.5 hour and concentrated (to ca. 300 mL). Standard solvent swaps to n-heptane (1.4 L×2) of the residue gave XIVax (280 g, 96% HPLC purity), which can was used directly for the next step.

To a solution of XIVax (209 g, from 0.54 mol of XIIa) and (DHQ)$_2$PHAL (21 g, 0.027 mol) in THF (1.7 L) was added a suspension of 4-methylmorpholine N-oxide (63 g, 0.54 mol) and K$_2$OsO$_4$.2H$_2$O (10 g, 0.027 mol) in H$_2$O (170 mL) at 0-10° C. The reaction mixture was stirred at 15-25° C. for 1 hour and after the reaction was complete as judged by HPLC, it was cooled to 0-10° C. and added sat. aq. NaHSO$_3$ (850 mL). After stirring for 0.5 hour, the mixture was filtered through a pad of diatomaceous earth and the filter was washed with MTBE (850 mL). The organic layer of the filtrate was collected and the aqueous layer was extracted by MTBE (850 mL). The combined organic layers were washed with brine (1.7 L×2) and concentrated under vacuum to give the crude XXIa (237 g) as a yellow oil, which was purified by column chromatography on silica gel (1.4 Kg, eluents: EtOAc/n-heptane=1:3 to EtOAc/MeOH=100:2) to give the pure XXIa as a diastereomeric mixture (107 g, yield: 58% from XIIa in 3 steps, 99% HPLC purity) while recovering XIVax (38 g, yield: 23% from XIIa, 98% HPLC purity).

Preparation of Compound IIIa'

To a solution of XXIa (107 g, 0.31 mol) in THF/H$_2$O (2.0 L, 1:1) at 0-10° C. was added NaIO$_4$ (80 g, 0.37 mol) in 10 portions over 45 minutes. When the reaction was complete as judged by HPLC after 0.5 hour, the mixture was directly extracted with EtOAc (1.0 L×2). The combined organic layers were washed with brine (1.0 L) and concentrated to give XVa as an off-white solid (91 g, 98% HPLC purity), which was used directly for the next step.

Under N$_2$ atmosphere, to a suspension of MeCHIPPh$_3$I (264 g, 0.49 mol) in THF (2.0 L) was added NaHMDS (480 mL, 2.0 M in THF) at −25 to −20° C. to form a red solution, which was stirred at −25 to −20° C. for 0.5 hour before it was further cooled to −60 to −50° C. A solution of XVa (100 g, 0.32 mol) in THF (300 mL) was added to the above mixture at −60 to −50° C. After stirring at −50° C. for 0.5 hour, the reaction was quenched by adding sat. aq. NH$_4$Cl (700 mL) while controlling the temperature between −60 to −30° C. The suspension was later warmed to 10-25° C. and filtered and the filter was washed by MTBE (500 mL). The organic layer of the filtrate was collected and the aqueous layer was extracted with MTBE (500 mL). The combined organic layers were concentrated under vacuum to give the crude IIIa' as a black oil (245 g, 43.6% HPLC purity), which was purified by column chromatography on silica gel (EtOAc/n-heptane=1:8) to give IIIa' (52.5 g, yield: 36%, 96.2% HPLC purity, Z/E ratio=98.3:1.7) as a yellow oil.

Example 5

Figure 23:
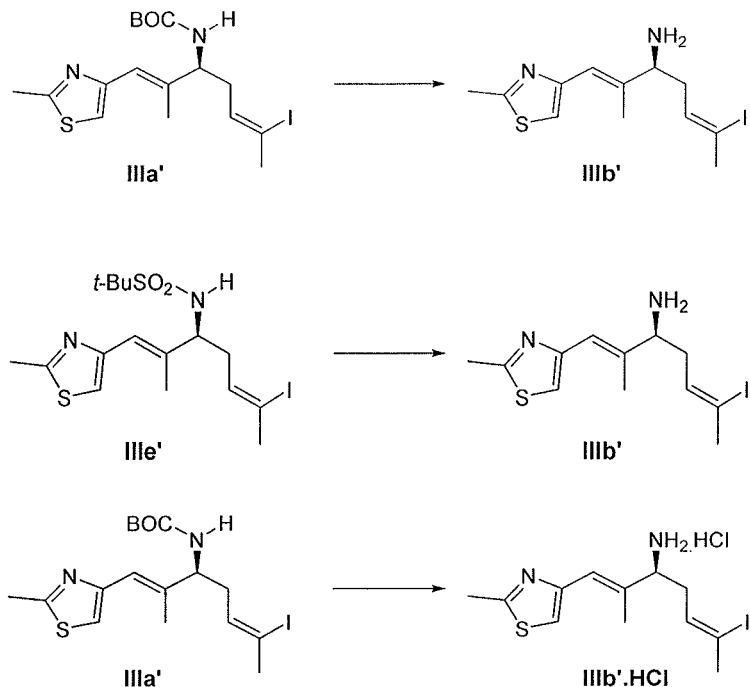
FIG. 23 provides Schemes from Example 5.

Preparation of IIIb' (see Schemes in FIG. 23)

The Preparation of IIIb' from IIIa'

To a solution of IIIa' (1.2 g, 2.7 mmol) in dry DCM (5 mL) was added TFA (5 mL) at 0° C. The resulting brown solution was stirred at this temperature for 1 h and the solvent was removed under reduced pressure. The residue was redissolved in DCM (10 mL), washed with aq. sat. NaHCO$_3$, dried over Na$_2$SO$_4$, filtered and concentrated under vacuum to get IIIb' (860 mg, yield: 92%) as a brown oil, which was used directly without any purification. $^1$H NMR (400 MHz, CDCl$_3$) δ 6.92 (s, 1H), 6.45 (s, 1H), 5.42 (t, J=6.0 Hz, 1H), 3.80 (brs, 2H), 3.58 (t, J=6.8 Hz, 1H), 2.66 (s, 3H), 2.41-2.34 (m, 2H), 2.02 (s, 3H), 1.21 (s, 3H).

The Preparation of IIIb' from IIIe'

To a solution of IIIe' (200 mg, 0.43 mmol) in dry DCM (13 mL) was added anisole (110 mg, 1 mmol) and 0.2 N CF$_3$SO$_3$H (13 mL) at 0° C. The resulting dark brown solution was stirred at this temperature for 1.5 h and aq. sat. Na$_2$CO$_3$ was added slowly to quench the reaction. The organic layer was separated, and the aqueous layer was extracted with DCM (10 ml×2). The combined organic layers were washed with brine, dried over Na$_2$SO$_4$, filtered and concentrated under vacuum. The residue was purified by column chromatography on silica gel using (eluent: DCM/MeOH=20:1) to give IIIb' (150 mg, yield: 85%) as a brow oil. $^1$H NMR (400 MHz, CDCl$_3$) δ 6.94 (s, 1H), 6.49 (s, 1H), 5.45 (t, J=6.0 Hz, 1H), 3.86-3.80 (brs, 2H), 3.60 (t, J=6.8 Hz, 1H), 2.68 (s, 3H), 2.41-2.38 (m, 2H), 2.05 (s, 3H), 1.24 (s, 3H).

The preparation of IIIb'.HCl from IIIa'

IIIa' (100 mg, 0.22 mmol) was dissolved in 6 N HCl in MeOH (5 mL) at 0° C., and the resulting solution was stirred at room temperature for 2 h. After the reaction was complete, the solvent was removed under reduced pressure to give the desired IIIb'.HCl (79 mg, yield 92%) as a brown solid.

Example 6

Figure 24:
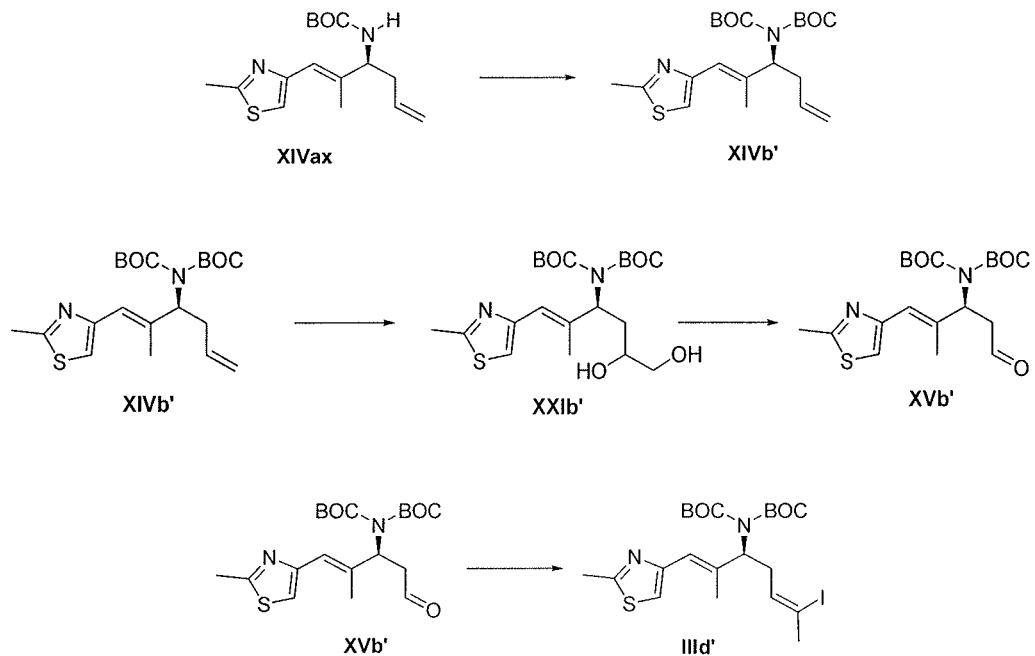
FIG. 24 provides Schemes from Example 6.

Preparation of IIId' (see Schemes in FIG. 24)

Preparation of XIVb'

To a solution of the mono-protected amine XIVax (6 g, 19.5 mmol) in THF (50 mL) was added NaHMDS (25 mL, 25 mmol) at −78° C. The mixture was stirred at this temperature for 30 minutes then (Boc)$_2$O (5 g, 23 mmol) was added. The mixture was warmed to room temperature and stirred overnight. After TLC analysis (petroleum ether/EtOAc=5:1) showed the reaction was complete, water was added to quench the reaction and was diluted with EtOAc and water. The organic layer was separated and the aqueous layer was extracted with EtOAc (50 mL×2). The combined organic layer was washed with brine, dried over Na$_2$SO$_4$ and concentrated in vacuum to give the crude product, which was purified by column chromatography on silica gel to give XIVb' (7 g, yield: 89%, two steps) as a yellow oil.

Preparation of XVb'

To a solution of the compound XIVb' (6.3 g, 15.4 mmol) in THF/t-BuOH/H$_2$O (1/1/0.1, 100 mL) was added NMO (4.34 g, 50% aqueous solution, 18.5 mmol) and OsO$_4$ (3.9 mL, 1 g in 50 mL t-BuOH) at 0° C. The mixture was warmed up to room temperature and stirred for 18 h. After TLC analysis (petroleum ether/EtOAc=1:1) showed the reaction was complete, the reaction was quenched with aq. sat. NaHSO$_3$ (40 mL) and H$_2$O (100 mL) at 0° C. and was stirred for 30 minutes. The mixture was extracted with MTBE (50 mL×4) and the collected organic layer was washed with brine (50 mL×2), dried over Na$_2$SO$_4$ and concentrated to give the crude product XXIb' (15 g).

To a solution of XXIb' (crude from 15.4 mmol of XIVb') in THF/H$_2$O (1/1, 80 mL) was added NaIO$_4$ (7.91 g, 37 mmol) at 0° C. and stirred for 40 minutes. After TLC analysis (petroleum ether/EtOAc=2:1) showed the reaction was complete, the reaction was quenched with water (200 mL). The mixture was extracted with EtOAc (50 mL×4) and the collected organic layers were washed with brine (50 mL×3), dried over Na$_2$SO$_4$ and concentrated under vacuum to give the crude product, which was purified by flash column chromatography (petroleum ether/EtOAc=2:1) to give the aldehyde XVb' (4.06 g, yield: 64% over two steps) as a yellow oil. $^1$H NMR (400 MHz, CDCl$_3$) δ 9.807 (s, 1H), 6.948 (s, 1H), 6.362 (s, 1H), 5.386 (t, J=7.2 Hz, 1H), 3.251-3.089 (m, 2H), 2.709 (s, 3H), 2.084 (s, 3H), 1.482 (s, 18H).

Preparation of IIId'

To a suspension of ethyltriphenylphosphonium iodide (8.36 g, 20 mmol) in THF (170 mL) was added n-BuLi (8 mL, 2.5 M, 20 mmol) at 17° C. under N$_2$ to form a red solution. The mixture was added to a solution of I$_2$ (5.08 g, 20 mmol) in THF (130 mL) dropwise at −75 to −80° C. to form a yellow suspension. The solution was stirred at −75° C. for 5 minutes and was warmed to −20° C. NaHMDS (9.35 mL, 2 M, 18.7 mmol) was added dropwise to form a red solution and the solution was stirred for 5 minutes. To this solution was added a solution of XVb' (4.06 g, 10 mmol) in THF (5 mL) dropwise and stirred at −20 to 10° C. for 1 h. After TLC analysis (Petroleum/EtOAc=2:1) showed that the reaction was complete, the reaction mixture was filtered through a pad of diatomaceous earth, concentrated and purified by column chromatography (Petroleum/EtOAc=5:1) to give the product IIId' (2.2 g, yield: 40%) as a yellow oil. $^1$H NMR (400 MHz, CDCl$_3$) δ 6.93 (s, 1 H), 6.46 (s, 1 H), 5.48 (t, J=6.4, 1H), 4.92 (dd, J=9, 6.2 Hz, 1H), 2.88 (m, 1H), 2.74 (m, 1H), 2.70 (s, 3H), 2.48 (m, 2H), 2.03 (s, 3H), 1.46 (s, 18H).

Example 7

Figure 25:
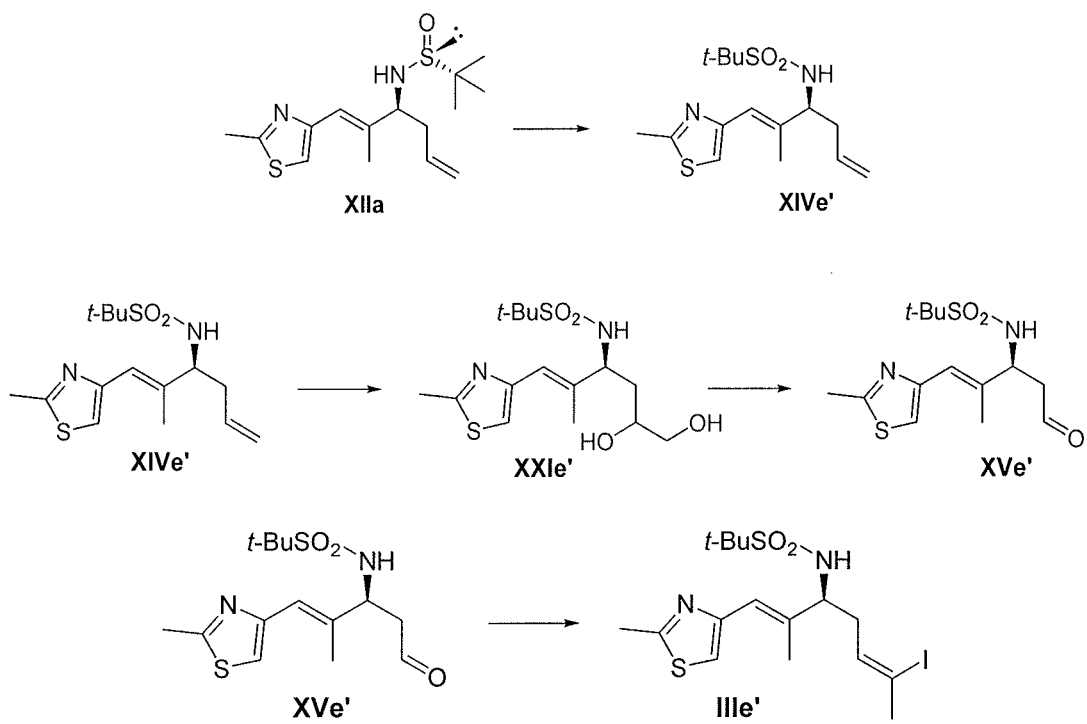
FIG. 25 provides Schemes from Example 7.

Preparation of IIIe' (see Schemes in FIG. 25)

The Preparation of Compound XIVe'

To a solution of XIIa (9.6 g, 30 mmol) in DCM (90 mL) was added m-CPBA (7.4 g, 70%, 30 mmol) at 0° C. in portions.

The resulting mixture was stirred at room temperature overnight before the reaction was quenched with aq. sat. $Na_2SO_3$ (120 mL). The organic layer was separated and the aqueous layer was extracted with DCM (60 ml×2). The combined organic layers were washed with brine, dried over $Na_2SO_4$, filtered and concentrated under vacuum. The residue was purified by column chromatography on silica gel (petroleum ether/EtOAc=20:1) to give XIVe' (8.9 g, yield: 87%) as a yellow oil. $^1$H NMR (400 MHz, $CDCl_3$) δ 6.903 (s, 1H), 6.412 (s, 1H), 5.758-5.654 (m, 1H), 5.099 (t, 2H), 4.578 (d, J=9.2 Hz, 1H), 4.039 (dd, J=15.6, 6.5 Hz, 1H), 2.658 (s, 3H), 2.499-2.379 (m, 2H), 2.050 (s, 3H), 1.327 (s, 9H).

The Preparation of XVe'

To a solution of XIVe' (1.7 g, 5.2 mmol) in THF/t-BuOH/$H_2O$ (1:1:0.1, 50 mL) was added NMO (1.5 g, 50% aq. solution, 6.2 mmol) and $OsO_4$ (1.3 mL, 0.104 mmol, 1 g in 50 mL t-BuOH) at 0° C. and the mixture was stirred at 23° C. for 18 h. After TLC analysis (Petroleum/EtOAc=1:1) showed that the reaction was complete, the reaction was quenched with aq. sat. $NaHSO_3$ (15 mL) and $H_2O$ (40 mL) at 0° C. and the mixture was stirred for 30 minutes before it was extracted with EtOAc (50 mL×4). The collected organic layers were washed with brine (50 mL×2), dried over $Na_2SO_4$ and concentrated to give the crude product XXIe' (6 g).

To a solution of XXIe' (crude, 6 g, 5.2 mmol) in THF/$H_2O$ (1:1, 80 mL) was added $NaIO_4$ (7.91 g, 37 mmol) at 0° C. and the mixture was stirred for 60 min. After TLC analysis (Petroleum/EtOAc=1:1) showed that the reaction was complete, the reaction was quenched with $H_2O$ (60 mL) and the mixture was extracted with EtOAc (50 mL×4). The collected organic layers were washed with brine (50 mL×3), dried over $Na_2SO_4$, concentrated and purified by column chromatography through a short pad of silica gel (Petroleum/EtOAc=1:1) to give the product XVe' (1.3 g, yield: 76%). $^1$H NMR (400 MHz, $CDCl_3$) δ 9.697 (s, 1H), 6.915 (s, 1H), 6.488 (s, 1H), 5.415 (d, J=9.2 Hz, 1H), 4.477 (dd, J=15.6, 6.8 Hz, 1H), 2.872-2.730(m, 2H), 2.625 (s, 3H), 2.061 (s, 3H), 1.300 (s, 9H).

The Preparation of IIIe'

To a suspension of ethyltriphenylphosphonium iodide (3.3 g, 7.88 mmol) in THF (60 mL) was added n-BuLi (3.2 mL, 2.5 M, 7.88 mmol) at 17° C. under $N_2$ to form a red solution. The mixture was added to a solution of $I_2$ (2 g, 7.88 mmol) in THF (45 mL) dropwise at −75 to −80° C. to form a yellow suspension, which was stirred at −75° C. for 5 min. Then the mixture was warmed to −20° C. and NaHMDS (3.7 mL, 2 M, 7.37 mmol) was added dropwise to form a red solution, which was stirred for another 5 min. To this solution was added a solution of XVe' (1.3 g, 3.94 mmol) in THF (5 mL) dropwise and stirred at −20 to 10° C. for 1 h. After TLC analysis (Petroleum ether/EtOAc=2:1) showed that the reaction was complete, the reaction mixture was filtered through a pad of diatomaceous earth, concentrated and purified by column chromatography on silica gel (Petroleum ether/EtOAc=5:1) to give the product IIIe' (730 mg, yield: 35%) as a colorless oil. $^1$H NMR (400 MHz, $CDCl_3$) δ6.96 (s, 1H), 6.47 (s, 1H), 5.48 (t, J=6 Hz, 1H), 4.14 (m, 2H), 2.71 (s, 3H), 2.51 (m, 5H), 2.12 (s, 3H), 1.37 (s, 9H).

Example 8

Figure 26:
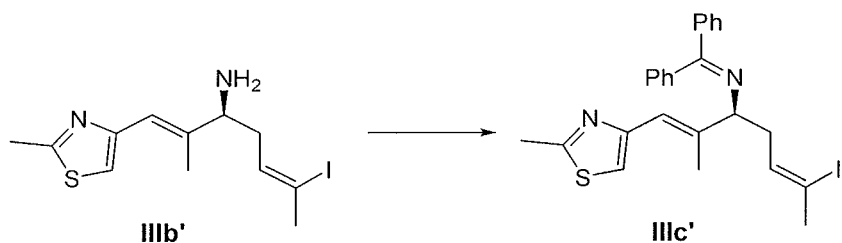
FIG. 26 provides Schemes from Example 8.

Preparation of IIIc' (see Scheme in FIG. 26)

To a solution of benzophenone (1.56 g, 8.6 mmol) in DME (50 mL) was added IIIb' (1.5 g, 8.6 mmol) and $Et_3N$ (3.6 mL, 25.8 mmol) at room temperature. The mixture was cooled to −78° C. and $TiCl_4$ (8.6 mL, 8.6 mmol, 1 N in DCM) was added. The resulting mixture was allowed to warm to room temperature and stirred overnight. After TLC analysis indicated the reaction was complete, $H_2O$ (50 mL) and EtOAc (200 mL) was added and the layers were separated. The aqueous layer was extracted with EtOAc (100 mL×2) and the combined organic layers were washed with aq. sat. $NaHCO_3$ (50 mL×3) and brine (50 mL×3), dried over $Na_2SO_4$, filtered and concentrated under vacuum. The residue was purified by column chromatography on silica gel to give IIIc' (890 mg, yield: 50%) as a yellow oil. $^1$H NMR (400 MHz, $CDCl_3$) δ 7.67-7.65 (m, 2H), 7.43-7.42 (m, 3H), 7.39-7.30 (m, 3H), 7.15-7.13 (m, 2H), 6.91 (s, 1H), 6.42 (s, 1H), 5.34 (t, J=6 Hz, 1H), 4.02 (t, J=6.4 Hz, 1H), 2.70 (s, 3H), 2.53 (m, 2H), 2.44 (s, 3H), 2.16 (s, 3H); $^{13}$C NMR (100 MHz, $CDCl_3$) δ166.9, 164.3, 153.2, 142.0, 139.9, 136.8, 132.3, 130.1, 129.9, 128.7, 128.4, 128.3, 128.0, 127.8, 119.5, 115.2, 102.3, 68.9, 42.3, 33.7, 19.2, 15.8.

Example 9

Figure 27:
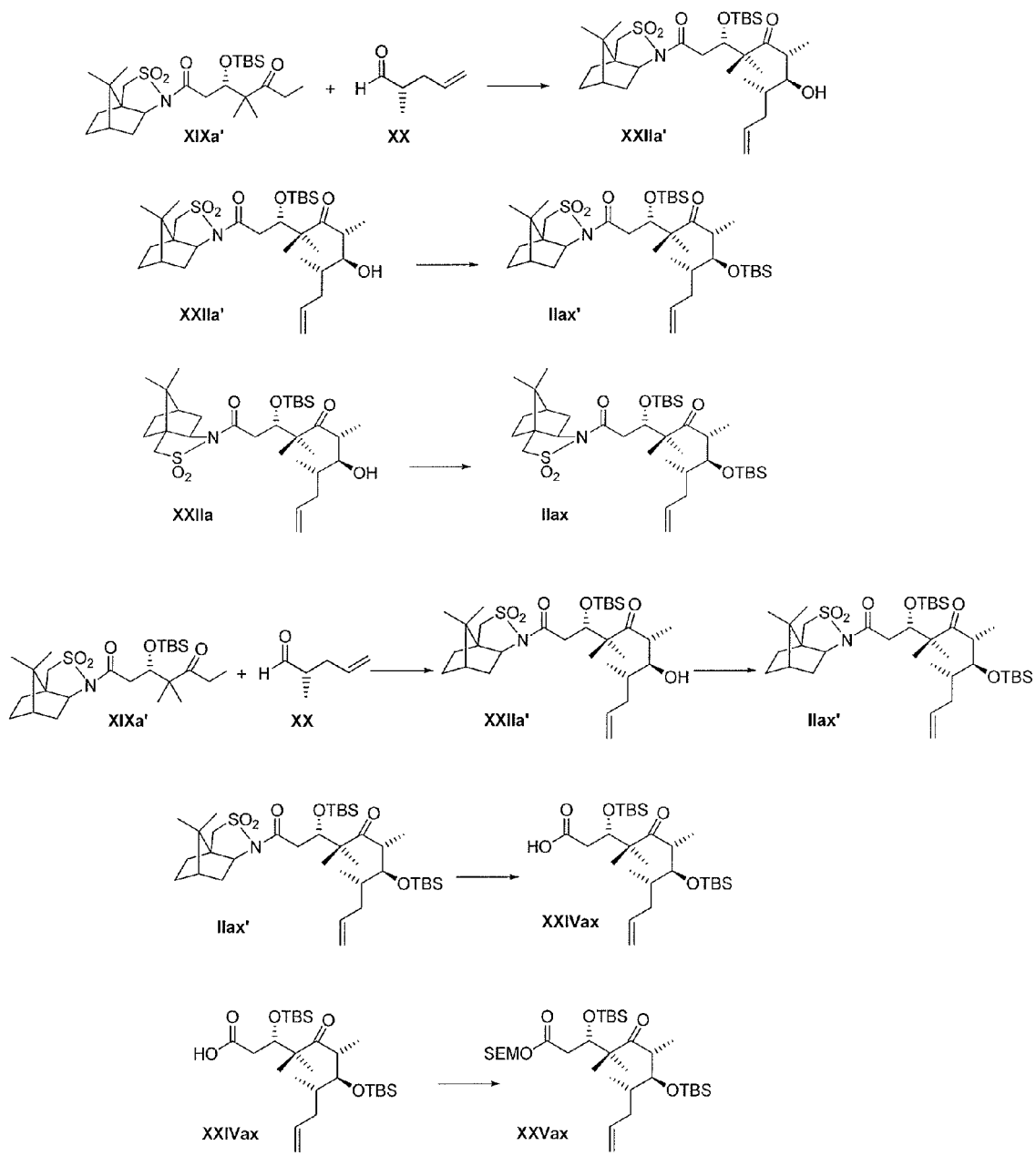
FIG. 27 provides Schemes from Example 9.

Preparation of XXVax (see Schemes in FIG. 27)

Preparation of XXIIa and XXIIa'

To a solution of compound XIXa' (15.0 g, 30 mmol, $R_f$=0.5, EtOAc/petroleum ether=1:3, $KMnO_4$) in dry DCM (87 mL) was added 1 N $TiCl_4$ (6.26 g, 33 mmol) in DCM (33 mL) at −78° C. and after 10 minutes, DIPEA (5.46 mL, 33 mmol) was added. The resulting mixture was stirred at −78° C. for another 1 h, then the solution of XX (4.4 g, 45 mmol) in DCM (13 mL) was added dropwise. The reaction mixture was slowly warmed up to room temperature over 3 h. After TLC analysis indicated the reaction was complete, aqueous phosphate buffer solution (43.6 mL, 2 N, pH=7.0, $NaH_2PO_4$/$Na_2HPO_4$) was added to quench the reaction. The organic layer was separated, and the aqueous was extracted with EtOAc (100 mL×4). The combined organics were dried, filtered and concentrated under vacuum. The residue was purified by column chromatography on silica gel (EtOAc/petroleum ether=1:10, $KMnO_4$) to give XXIIa' (13.5 g, yield: 75%, d.r. up to 5:1, $R_f$=0.4, EtOAc/petroleum ether=1:3, $KMnO_4$) as a colorless oil. $^1$H NMR (400 MHz, $CDCl_3$) δ 5.787-5.683 (m, 1H), 5.040-4.945 (m, 2H), 4.620 (t, J=4.4 Hz, 1H), 3.807 (dd, J=7.6, 4.8 Hz, 1H), 3.499 (s, 1H), 3.42 (q, J=13.6 Hz, 2H), 3.275 (d, J=9.6 Hz, 1H), 3.195 (q, J=7.2 Hz, 1H), 2.764 (d, J=4.4 Hz, 2H), 2.475 (dd, J=13.6, 1.2 Hz, 1H), 2.130-2.102 (m, 1H), 2.023 (dd, J=13.6, 7.6 Hz, 1H), 1.901-1.801 (m, 4H), 1.619-1.550 (m, 1H), 1.384-1.272 (m, 2H), 1.153 (s, 3H), 1.115 (s, 3H), 1.102 (s, 3H), 1.011 (d, J=6.8 Hz, 3H), 0.925 (s, 3H), 0.814 (s, 6H), 0.804 (s, 3H), 0.781 (d, J=6.8 Hz, 3H), 0.063 (s, 3H), 0.014 (s, 3H); $^{13}$C NMR (100 MHz, $CDCl_3$) δ 221.7, 169.6, 137.0, 116.3, 74.3, 71.2, 65.5, 53.8, 52.9, 48.4, 47.7, 44.7, 41.2, 40.9, 38.5, 37.3, 35.1, 33.0, 26.4, 26.0, 22.2, 20.7, 19.9, 19.5, 18.1, 15.0, 9.7, −4.3, −4.9.

The procedure for the preparation of XXIIa is the same as XXIIa'.

Preparation of IIax'

To a solution of XXIIa' (13.5 g, 22.5 mmol, $R_f$=0.4, EtOAc/petroleum ether=1:3, $KMnO_4$) in dry DCM (200 mL) was added 2,6-lutidine (7.2 g, 67.5 mmol) at −60° C. After stirring for 20 min, TBSOTF (12 g, 45 mmol) was added at this temperature and the resulting mixture was stirred at room temperature overnight. After TLC analysis indicated the reaction was complete, aq. sat. NH$_4$Cl (300 mL) was added to quench the reaction. The organic layer was separated and the aqueous was extracted with DCM (200 mL×2). The combined organic layers were dried over Na$_2$SO$_4$, filtered and concentrated under reduced pressure. The residue was purified by column chromatography on silica gel to give IIax' (16 g, yield: 100%, d.r. up to 5:1, R$_f$=0.8, EtOAc/petroleum ether=1:3, KMnO$_4$) as a white solid. M.P.=116-118° C.; $^1$H NMR (400 MHz, CDCl$_3$) δ 5.768-5.667 (m, 1H), 5.007-4.949 (m, 2H), 4.682 (brs, 1H), 3.869-3.817 (m, 2H), 3.724-3.709 (m, 1H), 3.428 (q, J=14 Hz, 2H), 3.172-3.096 (m, 1H), 2.773 (d, J=5.2 Hz, 2H), 2.252-2.148 (m, 2H), 2.072 (dd, J=13.6, 8 Hz, 1H), 1.932-1.802 (m, 4H), 1.404-1.315 (m, 3H), 1.235 (s, 3H), 1.148 (s, 3H), 1.083 (s, 3H), 0.955 (s, 3H), 0.901 (s, 12H), 0.853 (s, 6H), 0.833 (s, 3H), 0.098 (s, 3H), 0.061 (s, 6H), 0.004 (s, 3H); $^{13}$C NMR (100 MHz, CDCl$_3$) δ 217.9, 169.7, 137.9, 115.6, 78.0, 71.0, 70.4, 65.5, 53.7, 52.9, 48.4, 47.7, 45.7, 44.8, 41.8, 41.0, 39.6, 38.6, 37.6, 34.9, 26.3, 26.1, 23.6, 20.8, 19.9, 19.6, 18.7, 18.6, 18.3, 18.2, 16.5, 16.1, 13.0, −3.4, −3.6, −4.2, −4.8.

Preparation of IIax

To a solution of XXIIa (2.08 g, 3.5 mmol) in dry DCM (30 mL) was added 2,6-lutidine (1.13 g, 10.5 mmol) at −60° C. and then TBSOTf (1.8 g, 7 mmol) after 20 min. The resulting mixture was stirred at room temperature overnight. After TLC analysis indicated the consumption of XXIIa, aq. sat. NH$_4$Cl solution (30 mL) was added to quench the reaction. The organic phase was separated and the aqueous was extracted with DCM (20 mL×2). The combined organic layers were dried over Na$_2$SO$_4$, filtered and concentrated to afford a residue which was purified by column chromatography on silica gel (petroleum ether/EtOAc=10/1) to give IIax (2.38 g, yield 96%) as a yellow oil.

Preparation of IIax'

A solution of 1 M TiCl$_4$ in DCM (123.5 mL, 123.5 mmol) was added dropwise to a stirred solution of XIXa' (41.15 g, 82.3 mmol) in DCM (823 mL) over 0.5 hour under N$_2$ atmosphere while maintaining the solution temperature at −75° C. The reaction mixture was stirred for 0.5 hour before DIPEA (20.4 mL, 123.4 mmol) was slowly added. After the resulted dark red solution was stirred for another hour, a solution of XX (32.32 g, 329.3 mmol) in n-heptane (600 mL) was added over 1 hour at −75° C. The resulting mixture was stirred at that temperature for 2 hours and was warmed to 0° C., followed by stirring for another 0.5 hour. When the reaction was complete as judged by TLC (EtOAc/n-heptane=1:4), the reaction was quenched by adding an aqueous phosphate buffer solution (pH=7.0, 496 mL, 2 N prepared from NaH$_2$PO$_4$ and Na$_2$HPO$_4$) at 10° C. and stirred for 0.5 hour. The organic layer was collected and the aqueous layer was extracted with EtOAc (450 mL×2). The combined organic extracts were washed with sat. aq. NaHCO$_3$ (450 mL) and 20% aq. NaCl (450 mL), dried over MgSO$_4$ (20 g), filtered and concentrated in vacuo to give the crude XXIIa' (d.r.=86:14), which was used directly for the next step without purification.

The crude XXIIa' from the above was dissolved in DCM (1029 mL) and sequentially treated with 2,6-lutidine (38.3 mL, 328.8 mmol) and TBSOTf (47.3 mL, 206.0 mmol) under N$_2$ atmosphere while maintaining the solution temperature at <−73° C. The reaction mixture was stirred at 25° C. for 2 hours and then quenched by adding 10% aq. citric acid (1275 mL) after the reaction was complete as judged by TLC (EtOAc/n-heptane=1:8). The organic layer was collected and the aqueous layer was extracted with DCM (600 mL). The combined organic extracts were washed with 20% aq. NaCl (900 mL), dried over MgSO$_4$ (20 g), filtered and concentrated to ca. 620 mL. The solvent was swapped by MeOH (600 mL×3) to obtain the crude IIax' suspended in MeOH (ca. 600 mL), which was heated to 65-70° C. for dissolution. The clear solution was gently cooled and kept at 57° C. for 0.5 hour before it was further cooled to 25° C. After 2 hours at 25° C., the resulted suspension was filtered and the solids were washed with MeOH (205 mL) to give the pure IIax' as a pure white solid (35.55 g, yield: 61%, d.r.=99.2:0.79, M.P.=141-142° C.).

Preparation of XXIVax

To a solution of IIax' (16 g, 22.5 mmol, R$_f$=0.6, EtOAc/petroleum ether=1:5, KMnO$_4$) in THF/MeOH/H$_2$O (104 mL/17.2 mL/25.9 mL) was added LiOH/H$_2$O (3.8 g, 89.9 mmol) and 30% H$_2$O$_2$ (25.5 g, 225 mmol) at 0° C. The resulting mixture was stirred at room temperature overnight. The reaction was quenched with sat. aq. NaHSO$_3$ (195 mL) and the aqueous was extracted with EtOAc (100 mL×3). The combined organic layers were dried, filtered and concentrated under reduced pressure. The residue (XXIVax, R$_f$=0.3, EtOAc/petroleum ether=1:5, KMnO$_4$) was used directly in the next step without further purification.

Preparation of XXVax

To a solution of compound XXIVax (16 g, 31.1 mmol, crude, R$_f$=0.3, EtOAc/petroleum ether=1:5, KMnO$_4$) in DMF (59 mL) was added SEMCl (5.9 mL, 34.2 mmol) and DMAP (0.40 g, 3.11 mmol) at room temperature. The mixture was cooled to 0° C. and Et$_3$N (5.9 mL, 46.6 mmol) was added. The mixture was warmed up to room temperature and stirred overnight. After TLC analysis (petroleum ether/EtOAc=5:1) showed the reaction was complete, the mixture was diluted with EtOAc (100 mL) and water (50 mL). The organic layer was separated and the aqueous layer was extracted with EtOAc (50 mL×2). The combined organic layer was washed with brine, dried over Na$_2$SO$_4$ and concentrated under reduced pressure to give the product, which was purified by column chromatography on silica gel (petroleum ether/EtOAc=80:1) to give compound XXVax (9.4 g, yield: 64.7% for two steps, R$_f$=0.9, EtOAc/petroleum ether=1:5, KMnO$_4$) as a colorless oil. $^1$H NMR (400 MHz, CDCl$_3$) δ 5.77-5.66 (m, 1H), 5.26 (q, J=10.4, 6.4 Hz, 2H), 5.00-4.95 (m, 2H), 4.58-4.39 (m, 1H), 3.85-3.78 (dd, J=18.4, 7.6 Hz, 1H), 3.69 (t, J=8.8 Hz, 2H), 3.20-3.08 (m, 1H), 2.51-2.41 (m, 1H), 2.36-2.21 (m, 1H), 1.88-1.79 (m, 1H), 1.24 (s, 3H), 1.07-1.04 (m, 6H), 0.97-0.84 (m, 25H), 0.09-0.01 (m, 21H).

Example 10

Figure 28:
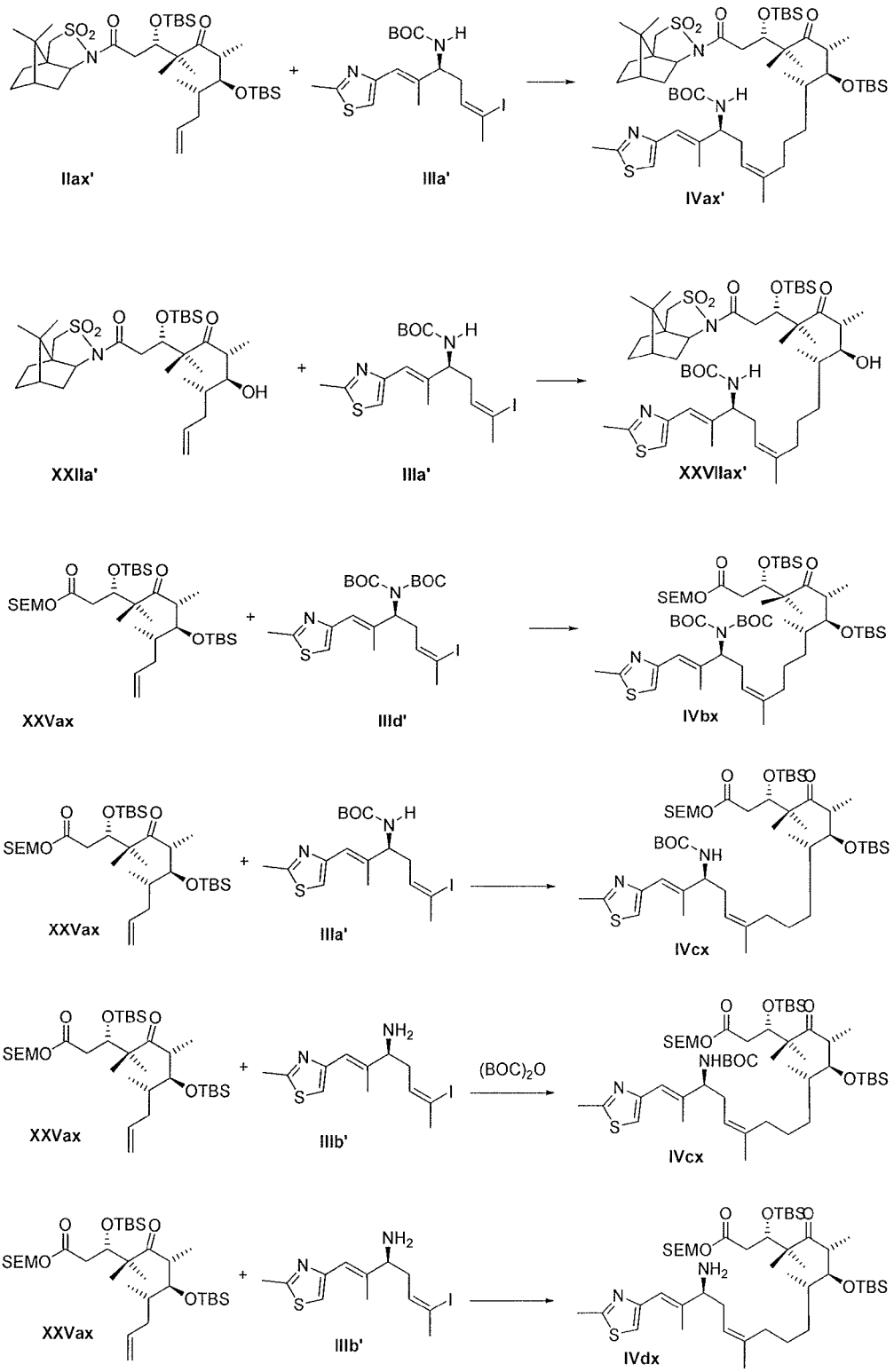
FIG. 28 provides Schemes from Example 10.
Figure 29:
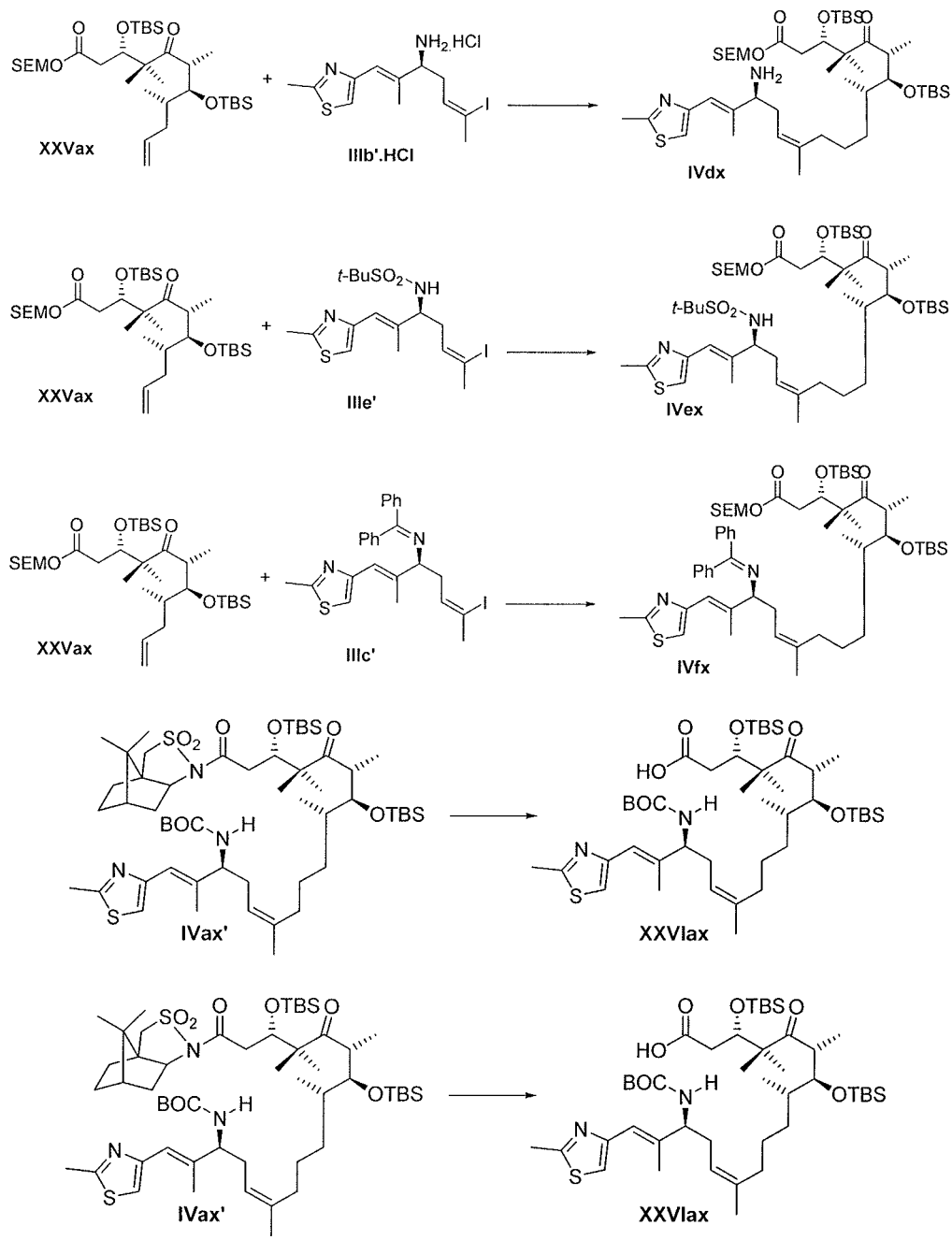
FIG. 29 provides Schemes from Example 10.
Figure 30:
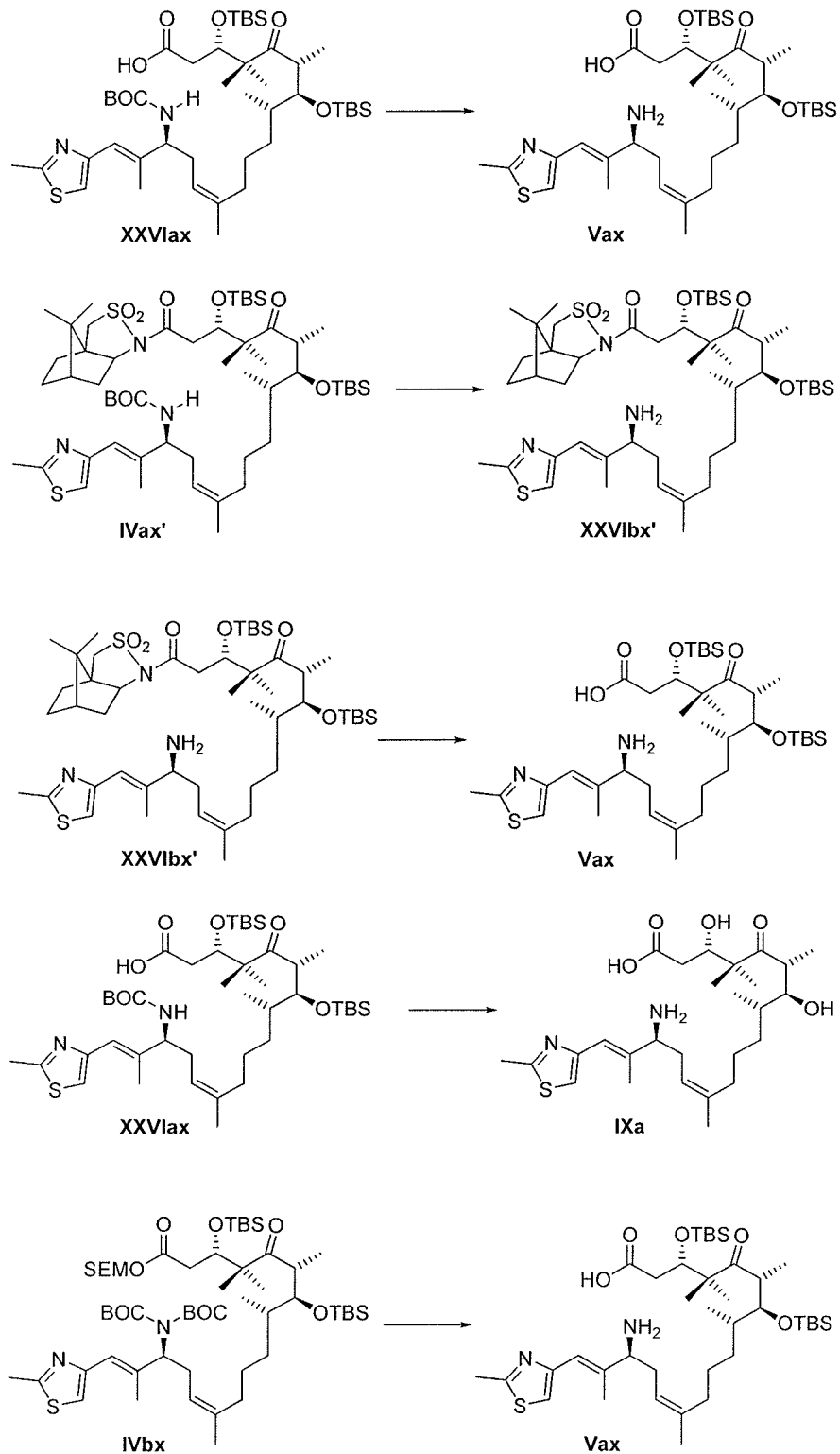
FIG. 30 provides Schemes from Example 10.

Preparation of Block ABC (see Schemes in FIGS. 28-30)

Preparation of IVax'

To a stirred solution of compound IIax' (2.44 g, 3.426 mmol) in THF (17.0 mL) was added 9-borabicyclo[3.3.1] nonane (9-BBN; 13.70 mL, 6.582 mmol, 0.5 M in THF) at room temperature. The reaction mixture was stirred at room temperature for 3 h. After the reaction was complete, as judged by TLC (n-heptane/EtOAc=4:1), water (0.70 mL) was added and the mixture was stirred for another 30 min. The resulting borane solution was transferred to a mixture of compound IIIa' (1.00 g, 2.230 mmol), Pd(dppf)Cl$_2$ (82 mg, 0.112 mmol) and Cs$_2$CO$_3$ (2.23 g, 6.582 mmol) in DMF (13.0 mL). The reaction mixture was stirred at 50° C. overnight. After the reaction was complete, as judged by TLC (n-heptane/EtOAc=4:1), the reaction mixture was diluted with EtOAc (60 mL) and water (60 mL). The organic layer was separated and the aqueous layer was extracted with EtOAc (60 mL×2). The combined organic layer was washed with brine, dried over MgSO$_4$ and concentrated in vacuo. The residue was purified by column chromatography on silica gel (eluent: n-heptane/EtOAc=6:1) to give IVax' (2.14 g, yield: 93%, R$_f$=0.24 for n-heptane/EtOAc=4:1) as a white foam. $^1$H NMR (400 MHz, CDCl$_3$) δ 6.90 (s, 1H), 6.43 (s, 1H), 5.27 (q, 2H), 5.09 (t, J=8.0 Hz, 1H), 4.64-4.55 (m, 1H), 4.38 (brs, 1H), 4.14-4.11 (m, 1H), 3.83-3.74 (dd, J=28.4, 6.8 Hz, 1H), 3.69 (t, J=8.0 Hz, 2H), 3.16-3.07 (m, 1H), 2.7 (s, 3H), 2.52-2.26 (m, 4H), 2.17 (s, 1H), 2.04 (s, 3H), 1.99-1.97 (m, 2H), 1.67 (s, 3H), 1.42 (s, 9H), 1.24 (s, 3H), 1.05-1.03 (m, 6H), 0.97-0.85 (m, 25H), 0.09-0.01 (m, 21H); LCMS 1034.6 [M+H]$^+$, 1034.4 [M+H]$^+$.

To a mixture of IIax' (9.25 g, 12.988 mmol) and 9-borabicyclo[3.3.1]nonane dimer (2.19 g, 8.974 mmol) was added THF (90.0 mL) at room temperature. The reaction mixture was stirred at room temperature for 3 h and after the reaction was complete, as judged by TLC (n-heptane/EtOAc=4:1), the mixture was added water (1.16 mL) and was stirred for another 30 min. The resulting borane solution was transferred to a mixture of compound IIIa' (4.48 g, 9.992 mmol), Pd(dppf)Cl$_2$ (365 mg, 0.499 mmol) and Cs$_2$CO$_3$ (9.77 g, 29.986 mmol) in DMF (58.0 mL). The reaction mixture was stirred at 50° C. for 1 h. After the reaction was complete, as judged by TLC (n-heptane/EtOAc=4:1), the reaction mixture was poured into a mixture of ethyl acetate (200 mL) and water (200 mL). The organic layer was separated and the aqueous layer was extracted with EtOAc (200 mL×2). The combined organic layers were washed with brine, dried over MgSO$_4$ and concentrated in vacuo. The residue was purified by column chromatography on silica gel (n-heptane/EtOAc=6:1) to give IVax' (9.58 g, yield: 93%, R$_f$=0.24, n-heptane/EtOAc=4:1) as a white foam.

Preparation of XXVIIax'

To a solution of compound XXIIa' (280 mg, 0.47 mmol) in THF (2.4 mL) was added 9-borabicyclo[3.3.1]nonane (1.89 mL, 0.94 mmol, 0.5 M in THF) at room temperature under an atmosphere of N$_2$. The mixture was stirred at room temperature for 2 h. After TLC analysis (petroleum ether/EtOAc=3:1) showed the reaction was complete, water (0.1 mL) was added to quench the reaction and the mixture was stirred for another 30 min. The resulting borane solution was transferred to a mixture containing compound IIIa' (100 mg, 0.22 mmol), Pd(dppf)Cl$_2$ (8 mg, 0.011 mmol) and Cs$_2$CO$_3$ (215 mg, 0.66 mmol) in DMF (1.3 mL) at 50° C. The reaction mixture changed from orange red to dark brown solution. The mixture was stirred at 50° C. for 5 h. After TLC analysis (petroleum ether/EtOAc=3:1) showed the reaction was complete, the mixture was diluted with EtOAc (5 mL) and water (5 mL). The organic layer was separated and the aqueous layer was extracted with EtOAc (5 mL×2). The combined organic layer was washed with brine (5 mL×3), dried over Na$_2$SO$_4$ and concentrated in vacuo to give the crude product, which was purified by column chromatography on silica gel to give compound XXVIIax' (120 mg, yield: 58.5%) as a colorless oil. $^1$H NMR (400 MHz, CDCl$_3$) δ 6.88 (s, 1H), 6.40 (s, 1H), 5.05 (t, J=8.0 Hz, 1H), 4.68 (brs, 1H), 4.63 (s, 1H), 3.81 (t, J=5.2 Hz, 3H), 3.52-3.37 (m, 3H), 3.28-3.20 (m, 2H), 2.77 (d, J=2.8 Hz, 2H), 2.67 (s, 3H), 2.31-2.05 (m, 4H), 2.01 (s, 9H), 1.86-1.83 (m, 4H), 1.64 (s, 3H), 1.39 (s, 9H), 1.30-1.28 (m, 2H), 1.17 (s, 3H), 1.12 (s, 3H), 1.11 (s, 3H), 1.01 (d, J=6.4 Hz, 3H), 0.94 (brs, 1H), 0.93 (s, 3H), 0.824 (s, 9H), 0.79 (d, J=4.0 Hz, 3H), 0.073 (s, 3H), 0.004 (s, 3H); $^{13}$C NMR (100 MHz, CDCl$_3$) δ 221.8, 171.2, 169.8, 164.3, 155.4, 153.2, 140.2, 138.8, 120.1, 118.7, 115.3, 79.3, 74.9, 71.3, 65.6, 60.4, 53.9, 53.0, 48.5, 47.8, 45.3, 44.8, 41.4, 41.1, 38.6, 38.4, 35.5, 32.6, 33.1, 32.1, 32.8, 32.5, 32.1, 28.5, 26.5, 26.1, 25.1, 23.6, 22.4, 21.1, 20.8, 20.0, 19.5, 19.3, 18.2, 15.5, 14.3, 9.8, −4.2, −4.8.

Preparation of IVbx

To a solution of compound XXVax (1.06 g, 1.65 mmol) in THF (14 mL) was added 9-borabicyclo[3.3.1]nonane (6.6 mL, 3.3 mmol) at room temperature. The mixture was stirred at room temperature for 1 h, and after TLC analysis (petroleum ether/EtOAc=5:1) showed the reaction was complete, the reaction mixture was added water (0.9 mL) and stirred for another 30 minutes. The resulting borane solution was transferred to a mixture containing compound IIId' (0.6 g, 1.1 mmol), (dppf) PdCl$_2$ (0.16 g, 0.22 mmol), AsPh$_3$ (0.067 g, 0.22 mmol) and Cs$_2$CO$_3$ (1.1 g, 3.3 mmol) in DMF (10 mL). The reaction mixture changed from orange red to dark brown solution. The mixture was stirred at room temperature for 30 minutes. After TLC analysis (petroleum ether/EtOAc=5:1) showed the reaction was complete, the mixture was diluted with EtOAc (50 mL) and water (50 mL). The organic layer was separated and the aqueous layer was extracted with EtOAc (30 mL×2). The combined organic layer was washed with brine, dried over Na$_2$SO$_4$ and concentrated in vacuum to give the product, which was purified by column chromatography on silica gel to give compound IVbx (1.04 g, yield: 88.9%) as a colorless oil. $^1$H NMR (400 MHz, CDCl$_3$) δ 6.90 (s, 1H), 6.48 (s, 1H), 5.26 (q, 2H), 5.12 (t, J=8.0 Hz, 1H), 4.79-4.76 (m, 1H), 4.38 (brs, 1H), 3.84-3.74 (m, 1H), 3.69 (t, J=8.4 Hz, 2H), 3.17-3.11 (m, 1H), 2.87-2.79 (m, 1H), 2.7 (s, 3H), 2.54-2.48 (m, 2H), 2.28 (dd, J=16.8, 6.8 Hz, 1H), 2.19-2.09 (m, 2H), 2.02 (s, 3H), 1.91-1.86 (m, 1H), 1.66 (s, 3H), 1.61 (d, J=4.4 Hz, 1H), 1.45 (s, 18H), 1.25 (s, 3H), 1.07-1.02 (m, 6H), 0.97-0.85 (m, 25H), 0.09-0.01 (m, 21H).

Preparation of IVcx

To a solution of compound XXVax (1.28 g, 2.6 mmol) in THF (17 mL) was added 9-borabicyclo[3.3.1]nonane (8 mL, 4 mmol) at room temperature. The mixture was stirred at room temperature for 1 h. After TLC analysis (petroleum ether/EtOAc=5:1) showed the reaction was complete, the mixture was added water (1.1 mL) and stirred for another 30 min. The resulting borane solution was transferred to a mixture containing compound IIIa' (0.6 g, 1.34 mmol), (dppf) PdCl$_2$ (0.2 g, 0.27 mmol), AsPh$_3$ (0.083 g, 0.27 mmol) and Cs$_2$CO$_3$ (1.3 g, 4.0 mmol) in DMF (10 mL). The reaction mixture changed from orange red to dark brown solution. The mixture was stirred at room temperature for 30 min. After TLC analysis (petroleum ether/EtOAc=5:1) showed the reaction was complete, the mixture was diluted with EtOAc (50 mL) and water (50 mL). The organic layer was separated and the aqueous layer was extracted with EtOAc (30 mL×2). The combined organic layers were washed with brine, dried over Na$_2$SO$_4$ and concentrated under vacuum to give the crude product, which was purified by column chromatography on silica gel to give compound IVcx (1.1 g, yield: 85.3%) as a pale yellow oil. $^1$H NMR (400 MHz, CDCl$_3$) δ 6.90 (s, 1H), 6.43 (s, 1H), 5.27 (q, 2H), 5.09 (t, J=8.0 Hz, 1H), 4.64-4.55 (m, 1H), 4.38 (brs, 1H), 4.14-4.11 (m, 1H), 3.83-3.74 (dd, J=28.4, 6.8 Hz, 1H), 3.69 (t, J=8.0 Hz, 2H), 3.16-3.07 (m, 1H), 2.7 (s, 3H), 2.52-2.26 (m, 4H), 2.17 (s, 1H), 2.04 (s, 3H), 1.99-1.97 (m, 2H), 1.67 (s, 3H), 1.42 (s, 9H), 1.24 (s, 3H), 1.05-1.03 (m, 6H), 0.97-0.85 (m, 25H), 0.09-0.01 (m, 21H).

Preparation of IVcx

To a solution of compound XXVax (165 mg, 0.255 mmol) in THF (2 mL) was added 9-borabicyclo[3.3.1]nonane (1.1 mL, 0.55 mmol) at room temperature. The mixture was stirred at room temperature for 1 h and after TLC analysis (petroleum ether/EtOAc=5:1) showed the reaction was complete, the mixture was added water (0.2 mL) and stirred for another 30 min. The resulting borane solution was transferred to a mixture containing compound IIIb' (60 mg, 0.17 mmol), (dppf) PdCl$_2$ (1.25 mg, 0.0017 mmol), (Boc)$_2$O (45 mg, 0.2 mmol) and Cs$_2$CO$_3$ (170 mg, 0.52 mmol) in DMF (2 mL) at 50° C. The reaction mixture changed from orange red to dark brown solution. The mixture was stirred at 50° C. for 2 h. After TLC analysis (petroleum ether/EtOAc=5:1) showed the reaction was complete, the mixture was diluted with EtOAc (5 mL) and water (5 mL). The organic layer was separated and the aqueous layer was extracted with EtOAc (5 mL×2). The combined organic layers were washed with brine, dried over Na$_2$SO$_4$ and concentrated under vacuum to give the crude product, which was purified by preparative-TLC to give compound IVcx (130 mg, yield: 79%) as a colorless oil.

Preparation of IVdx

To a solution of compound XXVax (2.0 g, 4.06 mmol) in THF (26.5 mL) was added 9-borabicyclo[3.3.1]nonane (12.5 mL, 6.24 mmol) at room temperature. The mixture was stirred at room temperature for 1 h. After TLC analysis (petroleum ether/EtOAc=5:1) showed the reaction was complete, the mixture was added water (1.7 mL) and stirred for another 30 min. The resulting borane solution was transferred to a mixture containing compound IIIb' (0.6 g, 1.73 mmol), (dppf) PdCl$_2$ (0.256 g, 0.35 mmol), AsPh$_3$ (0.107 g, 0.35 mmol) and Cs$_2$CO$_3$ (1.7 g, 5.19 mmol) in DMF (10 mL). The reaction mixture changed from orange red to dark brown solution. The mixture was stirred at room temperature for 30 min. After TLC analysis (petroleum ether/EtOAc=5:1) showed the reaction was complete, the mixture was diluted with EtOAc (50 mL) and water (50 mL). The organic layer was separated and the aqueous layer was extracted with EtOAc (30 mL×2). The combined organic layer was washed with brine, dried over Na$_2$SO$_4$ and concentrated under vacuum to give the crude product, which was purified by column chromatography on silica gel to give compound IVdx (0.9 g, yield: 60%) as a dark brown oil. $^1$H NMR (400 MHz, CDCl$_3$) δ 6.91 (s, 1H), 6.50 (s, 1H), 5.27 (q, 2H), 5.13 (t, J=6.8 Hz, 1H), 4.38 (brs, 1H), 3.84-3.74 (dd, J=28.8, 7.2 Hz, 1H), 3.69 (t, 8.4 Hz, 2H), 3.41 (t, J=6.0 Hz, 1H), 3.16-3.08 (m, 1H), 2.70 (s, 3H), 2.50-2.48 (m, 1H), 2.41-2.16 (m, 5 H), 2.03 (s, 3H), 1.99-1.97 (m, 2H), 1.68 (s, 3H), 1.65-1.61 (m, 2H), 1.48-1.38 (m, 3H), 1.24 (s, 3H), 1.07-1.03 (m, 6H), 0.97-0.85 (m, 25H), 0.09-0.01 (m, 21H).

To a solution of compound XXVax (150 mg, 0.23 mmol) in THF (1.5 mL) was added 9-borabicyclo[3.3.1]nonane (0.93 mL, 0.46 mmol) at room temperature. The mixture was stirred at room temperature for 1 h. After TLC analysis (petroleum ether/EtOAc=5:1) showed the reaction was complete, the mixture was added water (0.1 mL) and stirred for another 30 min. The resulting borane solution was transferred to a mixture containing compound IIIb'.HCl (60 mg, 0.156 mmol), (dppf) PdCl$_2$ (5.7 mg, 0.0078 mmol), and Cs$_2$CO$_3$ (305 mg, 0.936 mmol) in DMF (1.5 mL) at 50° C. The reaction mixture changed from orange red to dark brown solution. The mixture was stirred at 50° C. overnight and was then diluted with EtOAc (5 mL) and water (5 mL). The organic layer was separated and the aqueous layer was extracted with EtOAc (5 mL×2). The combined organic layers were washed with brine, dried over Na$_2$SO$_4$ and concentrated under vacuum to afford the crude product, which was purified by preparative-TLC to give compound IVdx (64 mg, yield: 50%) as a yellow oil.

Preparation of IVex

To a solution of compound XXVax (1.24 g, 1.92 mmol) in THF (16 mL) was added 9-borabicyclo[3.3.1]nonane (7.7 mL, 3.86 mmol) at room temperature. The mixture was stirred at room temperature for 1 h and after TLC analysis (petroleum ether/EtOAc=5:1) showed the reaction was complete, the mixture was added water (1.1 mL) and stirred for another 30 min. The resulting borane solution was transferred to a mixture containing compound IIIe' (0.6 g, 1.28 mmol), (dppf) PdCl$_2$ (0.19 g, 0.256 mmol), AsPh$_3$ (0.078 g, 0.256 mmol) and Cs$_2$CO$_3$ (1.25 g, 3.84 mmol) in DMF (10 mL). The reaction mixture changed from orange red to dark brown solution. The mixture was stirred at room temperature for 30 min and after TLC analysis (petroleum ether/EtOAc=5:1) showed the reaction was complete, the mixture was diluted with EtOAc (50 mL) and water (50 mL). The organic layer was separated and the aqueous layer was extracted with EtOAc (30 mL×2). The combined organic layer was washed with brine, dried over Na$_2$SO$_4$ and concentrated under vacuum to give the crude product, which was purified by column chromatography on silica gel to give compound IVex (1.1 g, yield: 87.3%) as a yellow oil. $^1$H NMR (400 MHz, CDCl$_3$) δ 6.93 (s, 1H), 6.44 (s, 1H), 5.27 (q, 2H), 5.09 (t, J=6.8 Hz, 1H), 4.38 (brs, 1H), 4.03-3.99 (m, 2H), 3.83-3.75 (dd, J=18.4, 7.6 Hz, 1H), 3.69 (t, J=8.4 Hz, 2H), 3.17-3.08 (m, 1H), 2.71 (s, 3H), 2.51-2.38 (m, 3H), 2.32-2.26 (dd, J=17.2, 6.8 Hz, 1H), 2.17 (s, 1H), 2.09 (s, 3H), 2.04-1.99 (m, 2H), 1.68 (s, 3H), 1.36 (s, 9H), 1.24 (s, 3H), 1.07-1.01 (m, 6H), 0.97-0.85 (m, 25H), 0.10-0.01 (m, 21H).

Preparation of IVfx

To a solution of compound XXVax (1.13 g, 1.76 mmol) in THF (14.8 mL) was added 9-borabicyclo[3.3.1]nonane (7.1 mL, 3.5 mmol) at room temperature. The mixture was stirred at room temperature for 1 h and after TLC analysis (petroleum ether/EtOAc=5:1) showed the reaction was complete, the mixture was added water (1 mL) and stirred for another 30 min. The resulting borane solution was transferred to a mixture containing compound IIIc' (0.6 g, 1.17 mmol), (dppf) PdCl$_2$ (0.17 g, 0.23 mmol), AsPh$_3$ (0.072 g, 0.23 mmol) and Cs$_2$CO$_3$ (1.14 g, 3.51 mmol) in DMF (10 mL). The reaction mixture changed from orange red to dark brown solution. The mixture was stirred at room temperature for 30 min. After TLC analysis (petroleum ether/EtOAc=5:1) showed the reaction was complete, the mixture was diluted with EtOAc (50 mL) and water (50 mL). The organic layer was separated and the aqueous layer was extracted with EtOAc (30 mL×2). The combined organic layer was washed with brine, dried over Na$_2$SO$_4$ and concentrated under vacuum to give the crude product, which was purified by column chromatography on silica gel to give compound IVfx (0.97 g, yield: 80.8%) as a yellow oil. $^1$H NMR (400 MHz, CDCl$_3$) δ 7.63 (d, J=7.6 Hz, 2H), 7.41-7.29 (m, 6H), 7.12 (d, J=6.8 Hz, 2H), 6.89 (s, 1H), 6.32 (s, 1H), 5.27 (q, 2H), 4.95 (t, J=6.8 Hz, 1H), 4.37 (brs, 1H), 3.88 (t, J=6.4 Hz, 1H), 3.82-3.73 (dd, J=27.6, 7.2 Hz, 1H), 3.70 (t, J=8.4 Hz, 2H), 3.16-3.11 (m, 1H), 2.69 (s, 3H), 2.53-2.36 (m, 3H), 2.32-2.26 (dd, J=16.4, 6.4 Hz, 1H), 2.16 (s, 1H), 1.99-1.84 (m, 2H), 1.60 (s, 3H), 1.36 (s, 9H), 1.24 (s, 3H), 1.08-1.01 (m, 6H), 0.98-0.85 (m, 25H), 0.09-0.02 (m, 21H).

Preparation of XXVIax'

To a stirred solution of IVax' (9.14 g, 8.834 mmol) in a mixture of THF (60.0 mL) and MeOH (15.0 mL) was added 10% aq. LiOH (8.46 mL, 35.336 mmol) at 0° C., followed by addition of 30% aq. $H_2O_2$ solution (5.01 mL, 44.170 mmol). The resulting mixture was warmed up to room temperature slowly and stirred at room temperature overnight. The reaction was quenched by adding sat. aq. $NaHSO_3$ (10.94 mL, 44.170 mmol) at 0° C. and the mixture was stirred for another 30 min. The resulting mixture was concentrated in vacuo and the residue was extracted with EtOAc (40 mL) and sat. aq. $NH_4Cl$. (40 mL). The organic layer was separated and the aqueous layer was extracted with EtOAc (40 mL×2). The combined organic layers were washed with brine, dried over $MgSO_4$, filtered and concentrated in vacuo. The residue was purified by column chromatography on silica gel (eluent: 2% MeOH/DCM to 5% MeOH/DCM) to give XXVIax (4.44 g, yield: 60%, $R_f$=0.33, 2% MeOH/DCM) as a white foam. $^1$H NMR (400 MHz, CDCl$_3$) δ 10.92 (brs, 1H), 6.85 (s, 1H), 6.42 (s, 1H), 5.05 (t, J=8.0 Hz, 1H), 4.71-4.70 (m, 1H), 4.35 (m, 1H), 4.09-4.04 (m, 1H), 3.81-3.72 (m, 1H), 3.11-3.07 (m, 1H), 2.64 (s, 3H), 2.42-2.39 (m, 2H), 2.27-2.22 (m, 3H), 1.97 (s, 3H), 1.96-1.90 (m, 3H), 1.63 (s, 3H), 1.37 (s, 9H), 1.20-1.01 (m, 12H), 0.87-0.85 (d, J=4.0 Hz, 3H), 0.85 (s, 9H), 0.82 (s, 9H), 0.05-0.01 (3s, 12H); $^{13}$C NMR (100 MHz, CDCl$_3$) δ 217.7, 176.0, 164.7, 152.8, 140.4, 138.4, 120.3, 115.0, 53.7, 53.6, 44.9, 40.0, 39.1, 39.0, 38.9, 32.5, 32.1, 31.0, 28.4, 26.3, 26.2, 26.1, 25.9, 23.6, (3×) 23.5 (3×), 23.4 (3×), 19.4, 18.9, 18.6, 18.4, 18.2, 17.4, 16.3, 15.8, −3.7, −3.9, −4.2, −4.7; LCMS 837.5 [M+H]$^+$, 837.3 [M+H]$^+$.

Preparation of XXVIax

To a stirred solution of IVax' (2.38 g, 2.30 mmol) in a mixed solvent of 2-Me-THF (24 mL) and MeOH (6 mL) was added 10% aq. NaOH (3.68 mL, 10.21 mmol) and 30% aq. $H_2O_2$ solution (1.30 mL, 13.07 mmol) at 0° C. The resulting mixture was warmed to 25° C. and stirred overnight. The reaction was quenched by adding sat. aq. $NaHSO_3$ (2.85 mL, 14.79 mmol) at 25° C. and the mixture was stirred for another 30 minutes before it was added 10% aq. citric acid (20 mL) and extracted with EtOAc (20 mL). The organic layer was collected and the aqueous layer was extracted with EtOAc (10 mL×2). The combined organic layers were washed with brine (20 mL), dried over MgSO$_4$ (5 g), filtered and concentrated in vacuo to afford the crude XXVIax, which was purified by column chromatography on silica gel (eluent: 2% MeOH/ DCM to 5% MeOH/DCM) to give the pure XXVIax (1.46 g, yield: 76%, $R_f$=0.33 for 2% MeOH/DCM) as a white foam.

Preparation of Vax from XXVIax

To a stirred solution of XXVIax (7.25 g, 8.658 mmol) in DCM (180.0 mL) was added 2,6-lutidine (10.08 mL, 86.582 mmol) and TMSOTf (12.54 mL, 69.266 mmol) at 0° C. The resulting mixture was warmed to room temperature and stirred for 1 h. The reaction mixture was poured into sat. aq. NH$_4$Cl (100 mL). The organic layer was separated and the aqueous layer was extracted with DCM (100 mL×2), and the combined organic layer was washed with brine, dried over Na$_2$SO$_4$, filtered and concentrated in vacuo. The residue was purified by column chromatography on silica gel (eluent: from 5% MeOH/DCM to 10% MeOH/DCM) to give Vax (5.90 g, yield: 92%, $R_f$=0.5, MeOH/DCM=1:10, UV) as a pale yellow foam. $^1$H NMR (400 MHz, CDCl$_3$) δ 6.98 (s, 1H), 6.55 (s, 1H), 6.45-6.36 (brs, 2H), 4.99 (t, J=2.8 Hz, 1H), 4.44 (brs, 1H), 3.89-3.82 (m, 1H), 3.66 (brs, 1H), 3.12-3. 09 (m, 1H), 2.67 (s, 3H), 2.54-2.33 (m, 3H), 2.26-2.13 (m, 2H), 2.10 (s, 1H), 1.81-1.79 (brs, 1H), 1.65 (s, 3H), 1.48 (brs, 2H), 1.14-1.03 (m, 12H), 0.89 (s, 9H), 0.84 (s, 9H), 0.82-0.81 (d, J=4.0 Hz, 3H), 0.07 (s, 3H), 0.06 (s, 6H), 0.04 (s, 3H); $^{13}$C NMR (100 MHz, CDCl$_3$) δ 218.1, 177.6, 164.7, 152.1, 139.7, 136.4, 122.5, 118.7, 117.2, 116.9, 74.6, 59.4, 53.9, 44.5, 42.3, 39.2, 32.6, 31.6, 31.0, 29.7, 26.4, 26.3, 26.2, 26.1, 23.5, 23.0, 19.1, 18.6, 18.4, 18.2, 18.1, 16.9, 16.5, 14.6, −3.8, −4.0, −4.8; LCMS 737.4 [M+H]$^+$, 737.3 [M+H]$^+$.

Preparation of XXVIbx'

Under an atmosphere of N$_2$ atmosphere, IVax' (95 mg, 0.09 mmol) was dissolved in dry DCM (2.5 mL), then 2,6-lutidine (0.103 mL, 0.92 mmol) and TMSOTf (0.165 mL, 0.92 mmol) were added at 0° C. The resulting mixture was warmed up to room temperature and stirred at room temperature for 2 h. When TLC indicated that all starting material was consumed, MeOH (0.165 mL) was added to quench the reaction. The mixture was stirred at room temperature for 10 min, and then the solvent was removed under reduced pressure. The residue was purified by column chromatography on silica gel (eluent: 2% MeOH/DCM to 10% MeOH/DCM) to give XXVIbx' (77 mg, yield: 90%, $R_f$=0.55, MeOH/DCM=1:10, UV) as a colorless oil. $^1$H NMR (400 MHz, CDCl$_3$) δ 6.90 (s, 1H), 6.49 (s, 1H), 5.12 (t, J=8.0 Hz, 1H), 4.76 (br, 214, NH), 4.66-4.65 (m, 1H), 3.84 (t, J=6.0 Hz, 1H), 3.78 (d, J=8.0 Hz, 1H), 3.42 (dd, J=16.0, 6.0 Hz, 2H), 3.13-3.09 (m, 1H), 2.76 (d, J=3.6 Hz, 1H), 2.69 (s, 3H), 2.51-2.20 (m, 6H), 2.16 (s, 3H), 2.14-2.02 (m, 3H) 1.87-1.84 (m, 3H), 1.67 (s, 3H), 1.65 (s, 3H), 1.25-1.22 (m, 9H), 1.14 (s, 3H), 1.07 (s, 6H), 0.95 (s, 3H), 0.88 (s, 9H), 0.84 (s, 9H), 0.09-0.00 (3s, 12H); $^{13}$C HNMR (100 MHz, CDCl$_3$) δ 217.7, 169.6, 164.2, 153.1, 143.7, 137.9, 121.4, 118.3, 114.9, 78.0, 71.1, 65.4, 59.8, 53.5, 52.8, 48.3, 47.6, 45.2, 44.7, 41.6, 38.5, 38.3, 34.1, 32.9, 32.5, 31.8, 30.3, 28.9, 26.3, 26.2 (×3), 26.1 (×3), 23.4, 22.6, 20.7, 19.8, 19.1, 18.8, 18.4, 18.1, 18.0, 15.9, −3.8, −4.0, −4.3, −4.8; LCMS 934.5 [M+H]$^+$, 934.4 [M+H]$^+$.

Preparation of Vax from XXVIbx'

To a stirred solution of XXVIbx' (75 mg, 0.08 mmol) in a mixture of THF (0.365 mL), MeOH (0.073 mL) was added 10% aq. LiOH (0.176 mL, 0.64 mmol) at 0° C., followed by addition of 30% aq. $H_2O_2$ solution (0.18 μL, 1.60 mmol). The resulting mixture was warmed up to room temperature slowly and stirred at room temperature overnight. The reaction was quenched by adding sat. aq. NaHSO$_3$ (0.396 mL) at 0° C. and the mixture was stirred for another 30 min. The resulting mixture was concentrated in vacuo and the residue was diluted with EtOAc (10 mL) and sat. aq. NH$_4$Cl (10 mL). The organic layer was separated and the aqueous layer was extracted with EtOAc (10 mL×2). The combined organic layer was washed with brine, dries over Na$_2$SO$_4$, filtered and concentrated in vacuo. The residue was purified by column chromatography on silica gel (MeOH/DCM=1:9) to give Vax (13 mg, yield: 22%, $R_f$=0.5, MeOH/DCM=1:10, UV) as a pale yellow foam. $^1$H NMR (400 MHz, CDCl$_3$) δ 6.98 (s, 1H), 6.55 (s, 1H), 6.45-6.36 (brs, 2H), 4.99 (t, J=2.8 Hz, 1H), 4.44

(brs, 1H), 3.89-3.82 (m, 1H), 3.66 (brs, 1H), 3.12-3. 09 (m, 1H), 2.67 (s, 3H), 2.54-2.33 (m, 3H), 2.26-2.13 (m, 2H), 2.10 (s, 1H), 1.81-1.79 (brs, 1H), 1.65 (s, 3H), 1.48 (brs, 2H), 1.14-1.03 (m, 12H), 0.89 (s, 9H), 0.84 (s, 9H), 0.82-0.81 (d, J=4.0 Hz 3H), 0.07 (s, 3H), 0.06 (s, 6H), 0.04 (s, 3H); $^{13}$C NMR (100 MHz, CDCl$_3$) δ 218.1, 177.6, 164.7, 152.1, 139.7, 136.4, 122.5, 118.7, 117.2, 116.9, 74.6, 59.4, 53.9, 44.5, 42.3, 39.2, 32.6, 31.6, 31.0, 29.7, 26.4, 26.3, 26.2, 26.1, 23.5, 23.0, 19.1, 18.6, 18.4, 18.2, 18.1, 16.9, 16.5, 14.6, −3.8, −4.0, −4.8; LCMS 737.4 [M+H]$^+$, 737.3 [M+H]$^+$.

Preparation of IXa from XXVIax

XXVIax (470 mg, 0.56 mmol) dissolved in dry DCM (20.0 mL) was cooled to 0° C. and added TFA (10.0 mL) slowly. The resulting mixture was stirred for 6 h at 0° C. After the reaction was complete as judged by TLC, the resulting mixture was concentrated in vacuo and the residue was added DCM (30 mL) and sat. aq. NaHCO$_3$ (20 mL). The organic layer was separated and the aqueous layer was extracted with DCM (30 mL×2). The combined organic layers were washed with brine, dried over Na$_2$SO$_4$, filtered and concentrated in vacuo. The residue was purified by column chromatography on silica gel (eluent: 2% MeOH/DCM to 15% MeOH/DCM) to give IXa (275 mg, yield: 96%, R$_f$=0.35, MeOH/DCM=1: 10, UV) as a pale yellow foam. $^1$H NMR (400 MHz, CD$_3$OD) δ 7.34 (s, 1H), 6.56 (s, 1H), 5.11 (t, J=7.2 Hz, 1H), 4.32 (d, J=9.6 Hz, 1H), 3.82 (t, J=7.2 Hz, 1H), 3.50 (t, J=5.6 Hz, 1H), 3.37 (s, 1H), 2.72 (s, 3H), 2.57 (t, J=7.2 Hz, 1H), 2.45 (d, J=15.2 Hz, 1H), 2.36-2.29 (m, 1H), 2.12-2.08 (m, 4H), 2.05 (s, 3H), 1.72 (s, 3H), 1.68-1.55 (m, 3H) 1.48-1.25 (m, 3H), 1.19 (s, 3H), 1.15 (s, 3H), 1.08 (d, J=6.4 Hz, 3H), 0.92 (d, J=6.4 Hz, 3H); $^{13}$C NMR (100 MHz, CD$_3$OD) δ 220.6, 179.3, 165.8, 151.3, 140.1, 134.6, 123.2, 117.8, 117.7, 76.1, 73.2, 59.1, 52.1, 43.1, 38.0, 35.8, 32.2, 30.6, 30.0, 25.4, 22.4, 20.9, 17.7, 17.4, 15.7, 13.1, 12.4; LCMS 509.3 [M+H]$^+$, 509.1 [M+H]$^+$.

Preparation of Vax from IVbx

IVbx (55 mg, 0.05 mmol) was dissolved in dry DCM (1 mL), then methyl(phenyl)sulfane (13 mg, 0.1 mmol), 2,6-lutidine (110 mg, 1 mmol) and TMSOTf (180 mg, 0.8 mmol) were added at 0° C. under an atmosphere of N$_2$. The resulting mixture was stirred at room temperature for 2 h, and after TLC analysis indicated that all starting material was consumed, MeOH (0.1 mL) was added to quench the reaction. The mixture was stirred at room temperature for 10 min, added DIPEA (260 mg, 2 mmol) and concentrated under reduced pressure to give crude Vax (360 mg) as a white solid, which was used for the next step without any further purification.

Example 11

Figure 31:
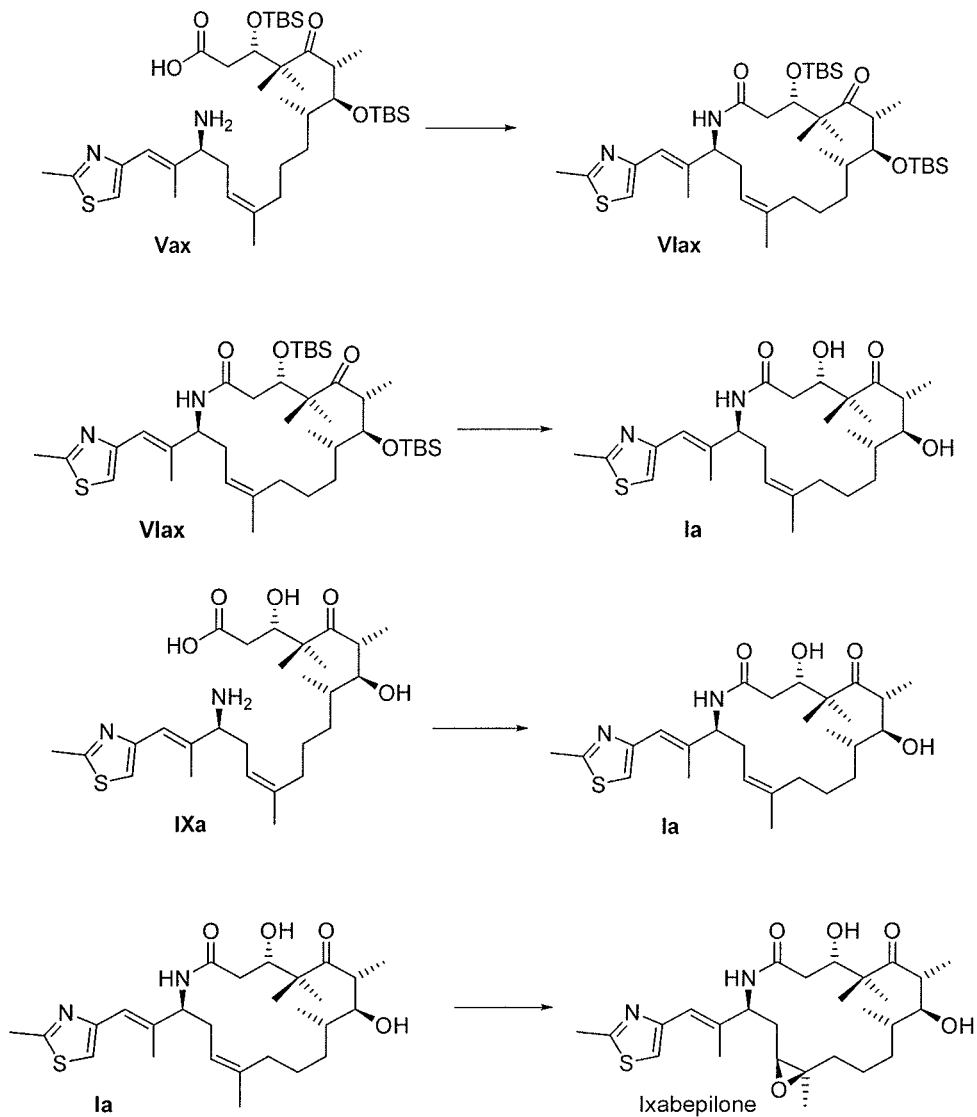
FIG. 31 provides Schemes from Example 11.

Preparation of Ixabepilone (see Schemes in FIG. 31)

Preparation of VIax from Vax

To a stirred solution of HATU (4.56 g, 12.004 mmol) and DIPEA (4.18 mL, 24.008 mmol) in THF (60.0 mL) was added a solution of Vax (2.95 g, 4.001 mmol) in THF (400.0 mL) over 5 hours via a syringe pump at 30° C. After the addition was complete, the resulting mixture was stirred at 30° C. for another 30 min and then filtered through a pad of diatomaceous earth followed by concentration in vacuo. The residue was diluted by EtOAc (100 mL) and 10% aq. citric acid (100 mL) and the organic layer was separated. The aqueous layer was extracted with EtOAc (100 mL×2) and the combined organic layers were washed with sat. aq. NaHCO$_3$ and brine, dried over MgSO$_4$, filtered and concentrated in vacuo. The residue was purified by column chromatography on silica gel (n-heptane/EtOAc=6:1) to give VIax (1.67 g, yield: 58%, R$_f$=0.28, n-heptane/EtOAc=4:1) as a white foam. $^1$H NMR (400 MHz, CDCl$_3$) δ 6.96 (s, 1H), 6.47 (s, 1H), 5.66 (brs, 1H), 5.19 (t, J=8.4 Hz, 1H), 4.23 (brs, 1H), 4.11 (d, J=9.2 Hz, 1H), 3.91 (dd, J=6.6, 1.6 Hz, 1H), 3.00-2.94 (m, 1H), 2.83 (d, J=14.8 Hz, 1H), 2.72 (s, 3H), 2.50 (dd, J=14.4, 10.8 Hz, 1H), 2.33 (t, J=6.8 Hz, 2H), 2.18 (brs, 1H), 2.09 (s, 3H), 1.81 (brs, 1H), 1.74 (s, 3H), 1.63 (m, 1H), 1.50 (t, J=13.2 Hz, 2H), 1.38-1.22 (m, 2H), 1.19 (s, 3H), 1.18 (s, 3H), 1.13 (d, J=6.8 Hz, 3H), 1.01 (d, J=6.8 Hz, 3H), 0.96 (s, 9H), 0.87 (s, 9H), 0.14 (s, 3H), 0.120 (s, 3H), 0.115 (s, 3H), −0.03 (s, 3H); $^{13}$C NMR (100 MHz, CDCl$_3$) δ 221.9, 169.8, 164.3, 153.0, 140.0, 139.1, 119.6, 118.3, 115.3, 75.3, 75.2, 60.4, 54.8, 54.4, 48.2, 40.9, 34.6, 31.5, 31.2, 27.8, 26.3, 26.2, 26.1, 26.0, 25.0, 24.8, 21.0, 19.2, 18.6, 18.4, 17.0, 16.8, 14.5, 14.2, −3.7, −4.1, −4.8; LCMS 719.4 [M+H]$^+$, 719.4 [M+H]$^+$.

Preparation of Ia from VIax

To a stirred solution of VIax (450 mg, 0.626 mmol) in DCM (4.5 mL) at 0° C. was added TFA (1.5 mL), and the resulting mixture was stirred at 0° C. for 6 h. After the reaction was complete as judged by TLC (n-heptane/EtOAc=1:1), the reaction mixture was diluted with DCM (45 mL) and poured into a mixture of ice and sat. aq. NaHCO$_3$. The organic layer was separated and the aqueous layer was extracted with DCM (50 mL×2). The combined organic layers were washed with sat. aq. NaHCO$_3$ and brine, dried over MgSO$_4$, filtered and concentrated in vacuo. The residue was purified by column chromatography on silica gel (n-heptane/EtOAc=1:2) to give Ia (255 mg, yield: 83%, R$_f$=0.22, n-heptane/EtOAc=1:2) as a white foam. $^1$H NMR (400 MHz, CDCl$_3$) δ 6.92 (s, 1H), 6.47 (s, 1H), 6.16 (d, J=8.0 Hz, 1H), 5.12 (t, J=8.0 Hz, 1H), 4.32 (m, 1H), 4.07 (d, J=8.0 Hz, 1H), 3.83-3.73 (m, 2H), 3.15 (m, 1H), 2.68 (s, 3H), 2.48-2.31 (m, 3H), 2.25-2.21 (m, 1H), 2.04 (s, 3H), 2.0-1.99 (m, 1H), 1.77-1.69 (m, 4H), 1.69 (s, 3H), 1.29 (s, 3H), 1.26-1.24 (m, 2H), 1.17 (d, J=4.0 Hz, 3H), 1.08 (s, 3H), 0.99 (d, J=4.0 Hz, 3H); $^{13}$C NMR (100 MHz, CDCl$_3$) δ 221.0, 170.7, 164.9, 152.6, 140.0, 139.5, 120.9, 118.3, 115.4, 74.9, 73.4, 56.4, 53.4, 42.6, 40.4, 38.6, 32.6, 31.6, 31.5, 29.9, 25.9, 23.3, 22.8, 22.5, 19.7, 19.2, 17.1, 15.9, 14.4, 14.1; LCMS 491.29 [M+H]$^+$.

Preparation of Ia from IXa

To a stirred solution of HATU (3.04 g, 8.00 mmol) and DIPEA (2.79 mL, 16.00 mmol) in THF (20.0 mL) was added a solution of IXa (407 mg, 0.80 mmol) in THF (40.0 mL) over 10 hours via a syringe pump at 30° C. The resulting mixture was stirred at 30° C. for another 12 hours and then filtered through a pad of diatomaceous earth followed by concentration in vacuo. The residue was diluted by EtOAc (20 mL) and 10% aq. citric acid (20 mL). The organic layer was separated and the aqueous layer was extracted with EtOAc (20 mL×2). The combined organic layers were washed with sat. aq. NaHCO$_3$ and brine, dried over MgSO$_4$, filtered and concentrated in vacuo. The residue was purified by column chromatography on silica gel (n-heptane/EtOAc=1:2) to give Ia (192 mg, yield: 49%, R$_f$=0.22, n-heptane/EtOAc=1:2) as a white foam.

Preparation of Ixabepilone

To a 250-mL three-neck flask equipped with a stir bar was added 10.0 mL of deionized water, 10.0 mL of acetone and 2.50 g of NaHCO$_3$. The resulting mixture was stirred vigorously in a 24° C. bath for 15 minutes. To this mixture was added 3 portions of potassium peroxymonosulfate (1.67 g) every 10-15 minutes under a reduced pressure (ca. 50-100 mmHg). DMDO was distilled out and obtained as an acetone solution after every addition of potassium peroxymonosulfate. Under a N$_2$ atmosphere, DMDO (10 mL) was transferred to the solution of Ia (61 mg, 0.124 mmol) in dry DCM (2.0 mL) slowly using a cannula while controlling the solution temperature at −78° C. Then the reaction mixture was warmed up to −50° C. and stirred for 1.5 h. When TLC analysis indicated the reaction was complete, excess DMDO was quenched by adding dimethyl sulfide (0.1 mL) at −50° C., and the mixture was warmed to room temperature and concentrated under reduced pressure. The residue was purified by column chromatography on silica gel (EtOAc/n-heptane=2:1) to give ixabepilone (27 mg, yield: 42.8%) as a colorless oil. $^1$H NMR (400 MHz, CDCl$_3$) δ 7.00 (m, 1H), 6.96 (s, 1H), 6.55 (s, 1H), 4.66-4.64 (m, 1H), 4.43 (brs, 1H), 4.06-4.04 (m, 1H), 3.79 (m, 1H), 2.82-2.79 (m, 1H), 2.77 (brs, 1H), 2.69 (s, 3H), 2.52-2.39 (m, 2H), 2.48 (brs, 1H), 2.31-2.26 (dd, J=12.0, 4.0 Hz, 1H), 1.96 (t, J=8.0 Hz, 2H), 1.62-1.53 (m, 4H), 1.37 (m, 3H), 1.33 (s, 3H), 1.27 (s, 3H), 1.16 (d, J=4.0 Hz, 3H), 1.09 (s, 3H), 0.98 (d, J=8.0 Hz, 3H); $^{13}$C NMR (100 MHz, CDCl$_3$) δ 220.8, 170.6, 165.0, 152.5, 138.0, 119.2, 116.0, 75.2, 73.6, 61.5, 61.2, 54.6, 52.7, 43.8, 40.4, 37.9, 31.9, 31.8, 30.7, 23.9, 23.0, 21.8, 21.0, 19.3, 17.3, 17.1, 14.4; LCMS 507.28 [M+H].

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A process for preparing an epoxide-containing aza-epothilone of formula VII

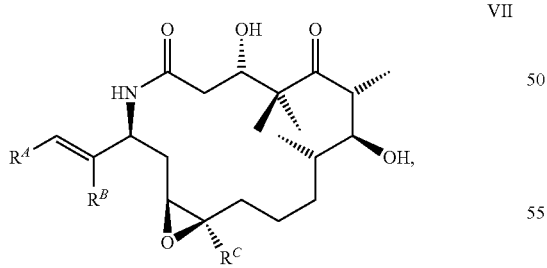

wherein R$^A$ is selected from the group consisting of substituted or unsubstituted aryl and substituted or unsubstituted heteroaryl, R$^B$ is selected from the group consisting of H, alkyl, and substituted or unsubstituted aryl, R$^C$ is selected from the group consisting of H, alkyl, substituted or unsubstituted aryl, substituted or unsubstituted heteroaryl, and fluoroalkyl, the process comprising:

a) contacting a bornane derivative of a compound of formula II

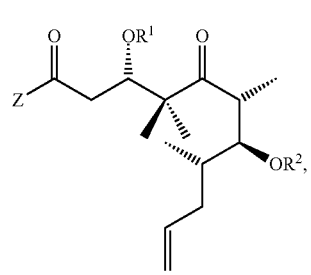

wherein Z is selected from the group consisting of,

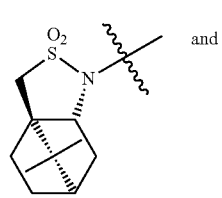

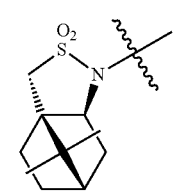

and

R$^1$ and R$^2$ are independently selected from the group consisting of hydrogen, triethylsilyl (TES), triisopropylsilyl (TIPS), tert-butyldimethylsilyl (TBS) and tert-butyldiphenylsilyl (TBDPS), with a vinyl halide of formula III

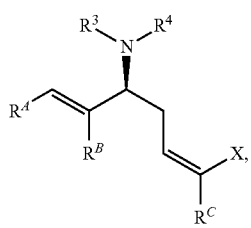

wherein X is a halide, and R$^3$ and R$^4$ are independently selected from the group consisting of H, tert-butyloxycarbonyl (BOC), and tert-butylsulfonyl (SO$_2$t-Bu), or together R$^3$ and R$^4$ are CPh$_2$, in the presence of a transition metal catalyst to provide a compound of the formula IV

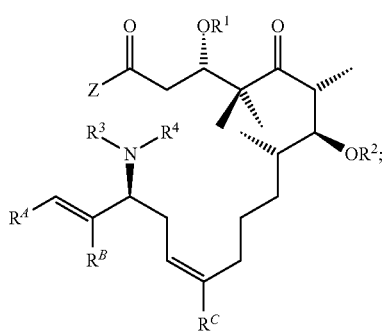

and b) converting the compound of formula IV to a compound of formula V

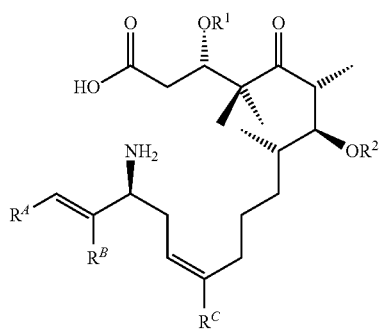

by converting Z to OH and converting $R^3$ and $R^4$ to H when one or both of $R^3$ and $R^4$ are other than H, wherein the converting steps are conducted in any order; and c) cyclizing the compound of formula V to the compound of formula VI

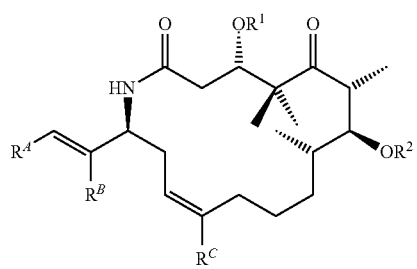

d) treating a compound of formula VI with an epoxidizing agent to form a compound of formula VIII

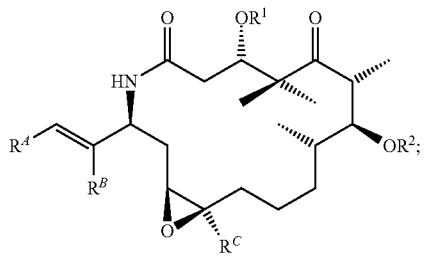

and e) deprotecting the compound of formula VIII to provide the epoxide containing azaepothilone VII.

2. A process according to claim 1, wherein the compound of formula IV is prepared from the compound of formula II by reaction with a borane selected from the group consisting of 9-borabicyclo-[3.3.1]nonane (9-BBN), 9-borabicyclo[3.3.1]nonane dimer (9-BBN dimer), disiamylborane, and dicyclohexylborane.

3. A process according to claim 2, wherein the borane is selected from the group consisting of 9-borabicyclo-[3.3.1]nonane (9-BBN) and 9-borabicyclo[3.3.1]nonane dimer (9-BBN dimer).

4. A process according to claim 1, wherein the transition metal catalyst comprises a metal selected from the group consisting of Ni and Pd.

5. A process according to claim 1, wherein Z is converted to OH by treatment of the compound of formula IV with a mixture comprising $H_2O_2$, a hydroxide, and a solvent.

6. A process according to claim 5, wherein the hydroxide is selected from the group consisting of sodium hydroxide and lithium hydroxide.

7. A process according to claim 6, wherein the hydroxide is sodium hydroxide.

8. A process according to claim 5, wherein the solvent comprises a mixture of 2-methyltetrahydrofuran and methanol.

9. A process according to claim 1, wherein $R^A$ is 2-methylthiazol-4-yl, and $R^B$ and $R^C$ are methyl.

10. A process according to claim 1, wherein the preparation of the compound of formula II comprises:

a) activating a compound of formula XVI'

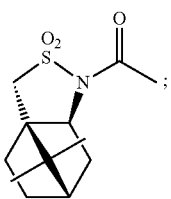

b) treating the activated compound of formula XVI' with a compound of formula XVII

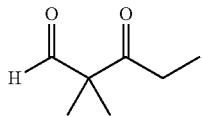

XVII in the presence of a Lewis acid to provide a compound of formula XVIII'

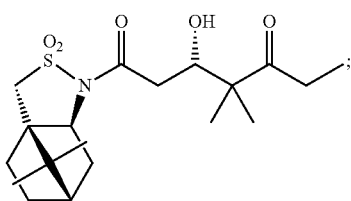

XVIII' c) optionally protecting the hydroxyl group of the compound of formula XVIII' with a protecting group selected from the group consisting of triethylsilyl (TES), triisopropylsilyl (TIPS), tert-butyldimethylsilyl (TBS) and tert-butyldiphenylsilyl (TBDPS) to provide a compound of formula XIX'

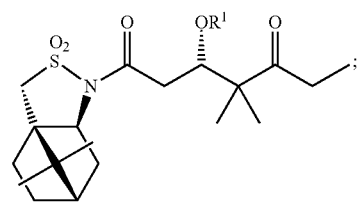

XIX' and d) activating the compound of formula XVIII' or the compound of formula XIX' and then reacting the activated compound with a compound of formula XX

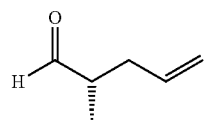

XX to provide the compound of formula II wherein $R^2$ is H; and e) optionally protecting the hydroxyl group of the compound of formula II with a protecting group selected from the group consisting of triethylsilyl (TES), triisopropylsilyl (TIPS), tert-butyldimethylsilyl (TBS) and tert-butyldiphenylsilyl (TBDPS) to provide a compound of formula II wherein $R^1$ and $R^2$ are both hydroxy protecting groups independently selected from the group consisting of triethylsilyl (TES), triisopropylsilyl (TIPS), tert-butyldimethylsilyl (TBS) and tert-butyldiphenylsilyl (TBDPS).

11. A process according to claim 10, wherein activating the compound of formula XVI' in step a) comprises contacting the compound of formula XVI' with a silyl triflate reagent and a base.

12. A process according to claim 11, wherein the silyl triflate reagent is tert-butyldimethylsilyl triflate.

13. A process according to claim 11, wherein the base is triethylamine.

14. A process according to claim 10, wherein the activating step of step d) is conducted by treating the compound of formula XVIII' or the compound of formula XIX' with a Lewis acid in the presence of an amine base at a low temperature.

15. A process according to claim 10, wherein the Lewis acid is a metal halide.

16. A process according to claim 15, wherein the metal halide is titanium tetrachloride ($TiCl_4$).

17. A process according to claim 16, wherein the amine base is N,N-diisopropylethylamine and the low temperature is equal to or colder than −50 °C.

18. A process according to claim 10, wherein $R^1$ and $R^2$ are both tert-butyldimethylsilyl (TBS).

19. A process according to claim 1, wherein the epoxide-containing azaepothilone VII is ixabepilone

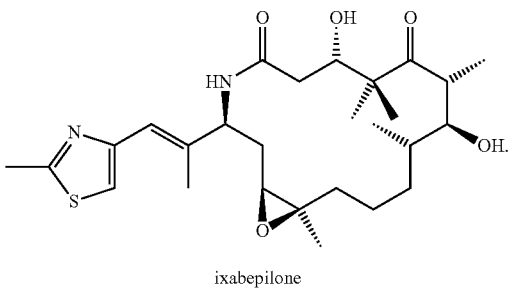

ixabepilone

* * * * *